US010808230B2

(12) United States Patent
Rushworth et al.

(10) Patent No.: US 10,808,230 B2
(45) Date of Patent: Oct. 20, 2020

(54) SELECTION METHODS FOR GENETICALLY-MODIFIED T CELLS

(71) Applicant: BOARD OF REGENTS, THE UNIVERSITY OF TEXAS SYSTEM, Austin, TX (US)

(72) Inventors: David Rushworth, Houston, TX (US); Laurence J. N. Cooper, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/552,821

(22) PCT Filed: Feb. 24, 2016

(86) PCT No.: PCT/US2016/019288
§ 371 (c)(1),
(2) Date: Aug. 23, 2017

(87) PCT Pub. No.: WO2016/138091
PCT Pub. Date: Sep. 1, 2016

(65) Prior Publication Data
US 2018/0298349 A1    Oct. 18, 2018

Related U.S. Application Data

(60) Provisional application No. 62/120,329, filed on Feb. 24, 2015, provisional application No. 62/120,790, filed on Feb. 25, 2015, provisional application No. 62/175,794, filed on Jun. 15, 2015.

(51) Int. Cl.
| C12N 9/06 | (2006.01) |
| C12N 9/10 | (2006.01) |
| A61K 35/17 | (2015.01) |
| C07K 14/54 | (2006.01) |
| C07K 14/575 | (2006.01) |
| C07K 14/725 | (2006.01) |
| C12N 5/0783 | (2010.01) |
| C12N 9/48 | (2006.01) |
| G01N 33/543 | (2006.01) |
| A61K 38/00 | (2006.01) |

(52) U.S. Cl.
CPC .............. *C12N 9/003* (2013.01); *A61K 35/17* (2013.01); *C07K 14/5434* (2013.01); *C07K 14/5443* (2013.01); *C07K 14/575* (2013.01); *C07K 14/7051* (2013.01); *C12N 5/0637* (2013.01); *C12N 5/0638* (2013.01); *C12N 9/1007* (2013.01); *C12N 9/48* (2013.01); *C12Y 105/01003* (2013.01); *C12Y 201/01045* (2013.01); *C12Y 304/22062* (2013.01); *G01N 33/54326* (2013.01); *A61K 38/00* (2013.01); *C12N 2501/04* (2013.01); *C12N 2501/06* (2013.01); *C12N 2501/2312* (2013.01); *C12N 2501/599* (2013.01); *C12N 2510/00* (2013.01)

(58) Field of Classification Search
None
See application file for complete search history.

(56) References Cited

U.S. PATENT DOCUMENTS

| 9,629,877 | B2 | 4/2017 | Cooper et al. | |
| 9,701,758 | B2 | 7/2017 | Cooper et al. | |
| 2011/0268766 | A1* | 11/2011 | Beech | A61K 48/0091 424/277.1 |
| 2012/0258532 | A1* | 10/2012 | Spencer | C12N 5/0636 435/325 |
| 2014/0349402 | A1 | 11/2014 | Cooper | |
| 2016/0096902 | A1 | 4/2016 | Cooper et al. | |
| 2016/0158285 | A1 | 6/2016 | Cooper et al. | |
| 2016/0256487 | A1 | 9/2016 | Cooper | |
| 2017/0044500 | A1 | 2/2017 | Cooper | |
| 2017/0158749 | A1 | 6/2017 | Cooper et al. | |
| 2017/0183407 | A1 | 6/2017 | Cooper et al. | |
| 2017/0333480 | A1 | 11/2017 | Cooper et al. | |
| 2017/0334968 | A1 | 11/2017 | Cooper | |
| 2018/0051265 | A1 | 2/2018 | Cooper | |

FOREIGN PATENT DOCUMENTS

| WO | WO 2013/074916 | 5/2013 |
| WO | WO 2014/186469 | 11/2014 |
| WO | WO 2014/190273 | 11/2014 |
| WO | WO 2015/061694 | 4/2015 |
| WO | WO 2015/075195 | 5/2015 |
| WO | WO 2015/123642 | 8/2015 |
| WO | WO 2015/157386 | 10/2015 |
| WO | WO 2015/164594 | 10/2015 |
| WO | WO 2015/164740 | 10/2015 |
| WO | WO 2016/073629 | 5/2016 |
| WO | WO 2016/073755 | 5/2016 |
| WO | WO 2016/145146 | 9/2016 |
| WO | WO 2017/048902 | 3/2017 |
| WO | WO 2017/075147 | 5/2017 |

OTHER PUBLICATIONS

Landis, et al. Creation and Characterization of 5-Fluorodeoxyuridine-resistant Arg50 Loop Mutants of Human Thymidylate Synthase. Cancer Research, 2001. 61:666-672.*
Bielas at al. Molecularly evolved Thymidine Synthase Inhibits 5-Fluorodeoxyuridine Toxicity in Human Hematopoietic Cells, Human Gene Therapy, 2009. 20:1703-1707.*
Davies, Jeff K., et al. "Combining CD19 redirection and alloanergization to generate tumor-specific human T cells for allogeneic cell therapy of B-cell malignancies." *Cancer research* (2010):0008-5472.

(Continued)

*Primary Examiner* — Christopher M Babic
*Assistant Examiner* — Kimberly A. Aron
(74) *Attorney, Agent, or Firm* — Parker Highlander PLLC

(57) ABSTRACT

In some aspects, isolated transgenic cells (e.g., transgenic T cells) are provided that comprise or express a transgene and $DHFR^{FS}$ and/or $TYMS^{SS}$. Methods for selecting transgenic cells are also provided.

19 Claims, 31 Drawing Sheets

Specification includes a Sequence Listing.

(56) References Cited

OTHER PUBLICATIONS

Jonnalagadda, et al. "Efficient selection of genetically modified human T cells using methotrexate-resistant human dihydrofolate reductase." *Gene therapy* 20.8 (2013): 853.
Jonnalagadda, et al. "Engineeting human T cells for resistance to methotrexate and mycophenolate mofetil as an in vivo cell selection strategy." *PloS one* 8.6 (2013): e65519.
Kacherovsky, et al. "Multiplexed gene transfer to a human T-cell line by combining Sleeping Beauty transposon system methotrexate selection." *Biotechnology and bioengineering* 112.7 (2015): 1429-1436.
PCT International Search Report and Written Opinion issued in International Application No. PCT/US2016/019288, dated Nov. 21, 2016.
PCT Invitation to Pay Additional Fees issued in International Application No. PCT/US2016/019288, dated Sep. 21, 2016.
Rushworth et al. "Antithymidylate resistance enables transgene selection and cell survival for T cells in the presence of 5-fluorouracil and antifolates." *Gene therapy* 23.2 (2016): 119-128.
Rushworth et al. "Antithymidylate resistance enables transgene selection and cell survival for T cells in the presence of 5-fluorouracil and antifolates." *Gene therapy* (2015): 1-10, Advance online publication.
Rushworth et al. "Dihydrofolate reductase and thymidylate synthase transgenes resistant to methotrexate interact to permit novel transgene regulation." *Journal of Biological Chemistry* (2015): jbc-C115.
Rushworth, "Selection Methods for Genetically-Modified T Cells: In Support of Translational Therapy", Dissertation, *The University of Texas Health Science Center at Houston and the University of Texas MD Anderson Cancer Center Graduate School of Biomedical Sciences*, 2015.

* cited by examiner

LEGEND
D$^{FS}$G: DHFR$^{FS}$-2A-eGFP
TS$^{SS}$G: TYMS$^{SS}$-2A-eGFP
TS$^{SS}$R: TYMS$^{SS}$-2A-RFP
NRF: ffLuc-2A-NeoR
RFP: NLS-mCherry

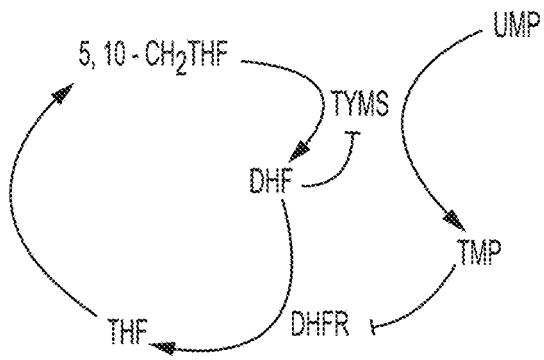
FIG. 9
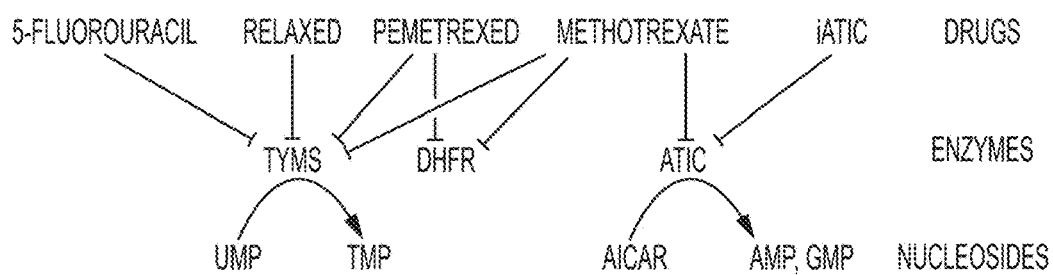
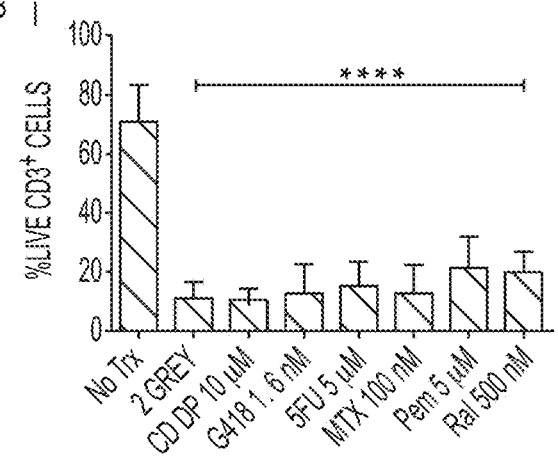
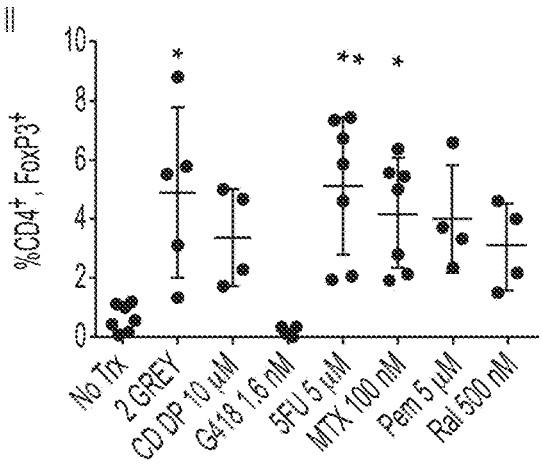
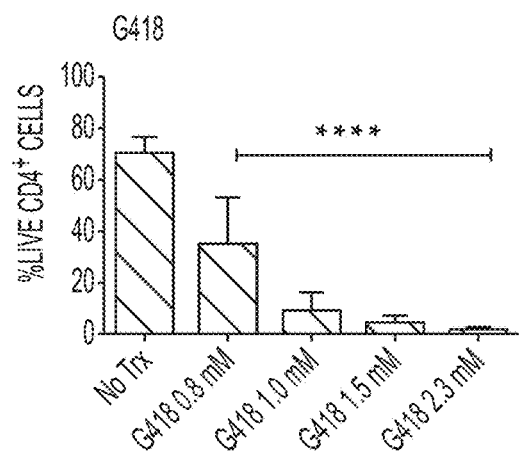
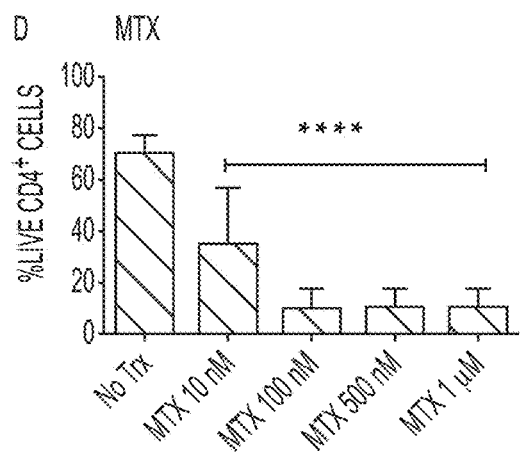
FIG. 10A-10D

SEQUENCE LISTING

<160> NUMBER OF SEQ ID NOS: 12

<210> SEQ ID NO 1
<211> LENGTH: 639
<212> TYPE: DNA
<213> ORGANISM: Artificial sequence
<220> FEATURE:
<223> OTHER INFORMATION: Synthetic oligonucleotide

<400> SEQUENCE: 1

| atggactaca aggacgacga cgacaaggat tacaaggatg atgatgataa ggactataaa | 60 |
| gacgacgatg ataaggacgt cgttggttcg ctaaactgca tcgtcgctgt gtcccagaac | 120 |
| atgggcatcg gcaagaacgg ggacttcccc tggccaccgc tcaggaatga atccagatat | 180 |
| ttccagagaa tgaccacaac ctcttcagta gaaggtaaac agaatctggt gattatgggt | 240 |
| aagaagacct ggttctccat tcctgagaag aatcgacctt aaagggtag aattaattta | 300 |
| gttctcagca gagaactcaa ggaacctcca caaggagctc atttctttc cagaagtcta | 360 |
| gatgatgcct aaaacttac tgaacaacca gaattagcaa ataaagtaga catggtctgg | 420 |
| atagttggtg gcagttctgt ttataaggaa gccatgaatc acccaggcca tcttaaacta | 480 |
| tttgtgacaa ggatcatgca agactttgaa agtgacacgt tttttccaga aattgatttg | 540 |
| gagaaatata aacttctgcc agaatacccca ggtgttctct ctgatgtcca ggaggagaaa | 600 |
| ggcattaagt acaaatttga agtatatgag aagaatgat | 639 |

<210> SEQ ID NO 2
<211> LENGTH: 639
<212> TYPE: DNA
<213> ORGANISM: Artificial sequence
<220> FEATURE:
<223> OTHER INFORMATION: Synthetic oligonucleotide

<400> SEQUENCE: 2

| atggactaca aggacgacga cgacaaggat tacaaggatg atgatgataa ggactataag | 60 |
| gacgatgatg acaaagacgt cgtgggcagc ctgaactgca tcgtggccgt gtcccagaac | 120 |
| atgggcatcg gcaagaacgg cgacttcccc tggccccctc tgcggaacga gagccggtac | 180 |
| ttccagcgga tgaccaccac cagcagcgtg gaaggcaagc agaacctcgt gatcatgggc | 240 |
| aagaaaacct ggttcagcat ccccgagaag aaccggcccc tgaagggccg gatcaacctg | 300 |
| gtgctgagca gagagctgaa agagccccct cagggcgccc acttcctgag cagatctctg | 360 |
| gacgacgccc tgaagctgac cgagcagcca gagctggcca caaggtgga catggtgtgg | 420 |
| atcgtgggcg gcagctccgt gtacaaagaa gccatgaacc accctggcca cctgaaactg | 480 |
| ttcgttaccc gtataatgca ggatttcgag agcgatacct tcttccccga gatcgacctg | 540 |
| gaaaagtaca agctgcttcc cgagtacccc ggcgtgctgt ccgatgtgca ggaagagaag | 600 |
| ggcatcaagt acaagttcga ggtgtacgag aagaatgac | 639 |

<210> SEQ ID NO 3
<211> LENGTH: 999
<212> TYPE: DNA
<213> ORGANISM: Artificial sequence
<220> FEATURE:
<223> OTHER INFORMATION: Synthetic oligonucleotide

<400> SEQUENCE: 3

| atgtatccgt acgacgtacc agactacgca tatccgtacg acgtaccaga ctacgcagac | 60 |
| gtccctgtgg ccggctcgga gctgccgcgc cggcccttgc cccccgccgc acaggagcgg | 120 |

```
gacgccgagc cgcgtccgcc gcacggggag ctgcagtacc tggggcagat ccaacacatc     180
ctccgctgcg gcgtcaggaa ggacgaccgc tcgagcaccg gcaccctgtc ggtattcggc     240
atgcaggcgc gctacagcct gagagatgaa ttccctctgc tgacaaccaa acgtgtgttc     300
tggaagggtg ttttggagga gttgctgtgg tttatcaagg gatccacaaa tgctaaagag     360
ctgtcttcca agggagtgaa aatctgggat gccaatggat cccgagactt tttggacagc     420
ctgggattct ccaccagaga agaagggac ttgggaccag tttatggctt ccagtggagg     480
cattttgggg cagaatacag agatatggaa tcagattatt caggacaggg agttgaccaa     540
ctgcaaagag tgattgacac catcaaaacc aaccctgacg acagaagaat catcatgtgc     600
gcttggaatc caagagatct tcctctgatg gcgctgcctc catgccatgc cctctgccag     660
ttctatgtgg tgaacagtga gctgtcctgc cagctgtacc agagatcggg agacatgggc     720
ctcggtgtgc ctttcaacat cgccagctac gccctgctca cgtacatgat tgcgcacatc     780
acgggcctga agccaggtga ctttatacac actttgggag atgcacatat ttacctgaat     840
cacatcgagc cactgaaaat tcagcttcag cgagaaccca gacctttccc aaagctcagg     900
attcttcgaa aagttgagaa aattgatgac ttcaaagctg aagactttca gattgaaggg     960
tacaatccgc atccaactat taaaatggaa atggctgtt                            999
```

<210> SEQ ID NO 4
<211> LENGTH: 1017
<212> TYPE: DNA
<213> ORGANISM: Artificial sequence
<220> FEATURE:
<223> OTHER INFORMATION: Synthetic oligonucleotide

<400> SEQUENCE: 4

```
atggactaca aggacgacga cgacaaggat tacaaggatg atgatgataa ggactataag      60
gacgatgatg acaaagacgt ccccgtggcc ggcagcgagc tgcctagaag gcctctgcct     120
cctgccgctc aggaaaggga cgccgaacct agacctcctc acggcgagct gcagtacctg     180
ggccagatcc agcacatcct gagatgcggc gtgcggaagg acgacagaag cagcacaggc     240
accctgagcg tgttcggaat gcaggccaga tacagcctgc gggacgagtt ccctctgctg     300
accaccaagc gggtgttctg gaagggcgtg ctggaagaac tgctgtggtt catcaagggc     360
agcaccaacg ccaaagagct gagcagcaag ggcgtgaaga tctgggacgc caacggcagc     420
agagacttcc tggacagcct gggcttcagc accagagagg aaggcgatct gggtcccgtg     480
tacgggtttc aatggcggca cttcggcgcc gagtatcggg acatggagag cgactacagc     540
ggccagggcg tggaccagct gcagagagtg atcgacacca tcaagaccaa ccccgacgac     600
cggcggatca tcatgtgcgc ctggaacccc agagatctgc ccctgatggc cctgcctcca     660
tgtcacgccc tgtgccagtt ctacgtcgtg aactccgagc tgagctgcca gctgtaccag     720
cggagcggcg atatgggact gggcgtgccc ttcaatatcg ccagctacgc cctgctgacc     780
tacatgatcg cccacatcac cggcctgaag cccggcgact tatccacac cctgggcgac     840 gcccatatct acctgaacca catcgagccc ctgaagattc agctgcagcg cgagcccaga     900
cccttcccaa agctgcggat cctgcggaag gtggaaaaga tcgacgactt caaggccgag     960
gacttccaga tcgagggcta caaccccac cccacaatca gatggaaat ggccgtg        1017
```

<210> SEQ ID NO 5
<211> LENGTH: 39
<212> TYPE: DNA
<213> ORGANISM: Artificial sequence -continued

```
<220> FEATURE:
<223> OTHER INFORMATION: Synthetic oligonucleotide

<400> SEQUENCE: 5
cccgggcccg gcgccatgcc acctcctcgc ctcctcttc                              39

<210> SEQ ID NO 6
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 6
ggtacccttg tacagctcgt ccatgccgag agtgatcccg gcggcggtca c              51

<210> SEQ ID NO 7
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 7
gctagcacat gtgccaccat gattgaacaa gatggattgc acgcaggttc tccggccgct    60
tgg                                                                    63

<210> SEQ ID NO 8
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 8
aagcttccgc ggccctctcc gctaccgaag aactcgtcaa gaaggcgata gaaggcgatg    60
cgctgcgaat c                                                          71

<210> SEQ ID NO 9
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 9

Met Ala Pro Lys Lys Lys Arg Lys Val Gly Ile His Arg Gly Val Pro
1               5                   10                  15

<210> SEQ ID NO 10
<211> LENGTH: 251
<212> TYPE: PRT
<213> ORGANISM: Artificial sequence
<220> FEATURE:
<223> OTHER INFORMATION: Synthetic polypeptide

<400> SEQUENCE: 10

Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Val Val
                20                  25                  30

Gly Ser Leu Asn Cys Ile Val Ala Val Ser Gln Asn Met Gly Ile Gly
        35                  40                  45
```

-continued

Lys Asn Gly Asp Phe Pro Trp Pro Leu Arg Asn Glu Ser Arg Tyr
 50                  55                  60

Phe Gln Arg Met Thr Thr Thr Ser Ser Val Glu Gly Lys Gln Asn Leu
 65                  70                  75                  80

Val Ile Met Gly Lys Lys Thr Trp Phe Ser Ile Pro Glu Lys Asn Arg
                 85                  90                  95

Pro Leu Lys Gly Arg Ile Asn Leu Val Leu Ser Arg Glu Leu Lys Glu
            100                 105                 110

Pro Pro Gln Gly Ala His Phe Leu Ser Arg Ser Leu Asp Asp Ala Leu
        115                 120                 125

Lys Leu Thr Glu Gln Pro Glu Leu Ala Asn Lys Val Asp Met Val Trp
130                 135                 140

Ile Val Gly Gly Ser Ser Val Tyr Lys Glu Ala Met Asn His Pro Gly
145                 150                 155                 160

His Leu Lys Leu Phe Val Thr Arg Ile Met Gln Asp Phe Glu Ser Asp
                165                 170                 175

Thr Phe Phe Pro Glu Ile Asp Leu Glu Lys Tyr Lys Leu Leu Pro Glu
            180                 185                 190

Tyr Pro Gly Val Leu Ser Asp Val Gln Glu Glu Lys Gly Ile Lys Tyr
        195                 200                 205

Lys Phe Glu Val Tyr Glu Lys Asn Asp Gly Thr Gly Glu Arg Gly
210                 215                 220

Ser Leu Leu Thr Cys Gly Asp Val Glu Glu Asn Pro Gly Pro Leu Gly
225                 230                 235                 240

Leu Met Gly Leu Pro Phe Thr Ala Arg Phe Pro
                245                 250

<210> SEQ ID NO 11
<211> LENGTH: 316
<212> TYPE: PRT
<213> ORGANISM: Artificial sequence
<220> FEATURE:
<223> OTHER INFORMATION: Synthetic polypeptide

<400> SEQUENCE: 11

Asp Val Pro Val Ala Gly Ser Glu Leu Pro Arg Arg Pro Leu Pro Pro
 1               5                  10                  15

Ala Ala Gln Glu Arg Asp Ala Glu Pro Arg Pro Pro His Gly Glu Leu
             20                  25                  30

Gln Tyr Leu Gly Gln Ile Gln His Ile Leu Arg Cys Gly Val Arg Lys
         35                  40                  45

Asp Asp Arg Ser Ser Thr Gly Thr Leu Ser Val Phe Gly Met Gln Ala
 50                  55                  60

Arg Tyr Ser Leu Arg Asp Glu Phe Pro Leu Leu Thr Thr Lys Arg Val
 65                  70                  75                  80

Phe Trp Lys Gly Val Leu Glu Glu Leu Leu Trp Phe Ile Lys Gly Ser
                 85                  90                  95

Thr Asn Ala Lys Glu Leu Ser Ser Lys Gly Val Lys Ile Trp Asp Ala
            100                 105                 110

Asn Gly Ser Arg Asp Phe Leu Asp Ser Leu Gly Phe Ser Thr Arg Glu
        115                 120                 125

Glu Gly Asp Leu Gly Pro Val Tyr Gly Phe Gln Trp Arg His Phe Gly
    130                 135                 140

Ala Glu Tyr Arg Asp Met Glu Ser Asp Tyr Ser Gly Gln Gly Val Asp
145                 150                 155                 160

```
Gln Leu Gln Arg Val Ile Asp Thr Ile Lys Thr Asn Pro Asp Asp Arg
                165                 170                 175

Arg Ile Ile Met Cys Ala Trp Asn Pro Arg Asp Leu Pro Leu Met Ala
        180                 185                 190

Leu Pro Pro Cys His Ala Leu Cys Gln Phe Tyr Val Val Asn Ser Glu
        195                 200                 205

Leu Ser Cys Gln Leu Tyr Gln Arg Ser Gly Asp Met Gly Leu Gly Val
    210                 215                 220

Pro Phe Asn Ile Ala Ser Tyr Ala Leu Leu Thr Tyr Met Ile Ala His
225                 230                 235                 240

Ile Thr Gly Leu Lys Pro Gly Asp Phe Ile His Thr Leu Gly Asp Ala
                245                 250                 255

His Ile Tyr Leu Asn His Ile Glu Pro Leu Lys Ile Gln Leu Gln Arg
                260                 265                 270

Glu Pro Arg Pro Phe Pro Lys Leu Arg Ile Leu Arg Lys Val Glu Lys
            275                 280                 285

Ile Asp Asp Phe Lys Ala Glu Asp Phe Gln Ile Glu Gly Tyr Asn Pro
        290                 295                 300

His Pro Thr Ile Lys Met Glu Met Ala Val Gly Thr
305                 310                 315

<210> SEQ ID NO 12
<211> LENGTH: 186
<212> TYPE: PRT
<213> ORGANISM: Artificial sequence
<220> FEATURE:
<223> OTHER INFORMATION: Synthetic polypeptide

<400> SEQUENCE: 12

Val Gly Ser Leu Asn Cys Ile Val Ala Val Ser Gln Asn Met Gly Ile
1               5                   10                  15

Gly Lys Asn Gly Asp Phe Pro Trp Pro Pro Leu Arg Asn Glu Ser Arg
                20                  25                  30

Tyr Phe Gln Arg Met Thr Thr Thr Ser Ser Val Glu Gly Lys Gln Asn
            35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Tyr Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

SELECTION METHODS FOR GENETICALLY-MODIFIED T CELLS

This application is a national phase application under 35 U.S.C. § 371 of International Application No. PCT/US2016/019288, filed Feb. 24, 2016, which claims the benefit of U.S. Provisional Patent Application Nos. 62/120,329, filed Feb. 24, 2015, 62/120,790, filed Feb. 25, 2015, and 62/175,794, filed Jun. 15, 2015, the entirety of each of which is incorporated herein by reference.

INCORPORATION OF SEQUENCE LISTING

The sequence listing that is contained in the file named "UTFCP1272WO_ST25.txt", which is 13 KB (as measured in Microsoft Windows®) and was created on Feb. 2, 2016, is filed herewith by electronic submission and is incorporated by reference herein.

BACKGROUND OF THE INVENTION

1. Field of the Invention

The disclosure relates to methods and compositions for preparing transgenic T cells and enriching for regulatory T cells in a population of T cells isolated from a mammal.

2. Description of Related Art

Targeting T cells to human disease has been in progress for more than 25 years. See Yee C., *Immunological reviews* 2014, 257(1):250-263. The initial aim of clinical trials was to direct T cells to target and kill diffuse cancers, for example metastatic melanoma and leukemia. See Yee C., *Immunological reviews* 2014, 257(1):250-263 and Roddie C and Peggs K S, *Expert opinion on biological therapy* 2011, 11(4):473-487.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Antigens on cancers are often times overexpressed or mutated versions of proteins found on non-cancerous cells. Although cancer antigens ideally demarcate only the cancer, in many instances cancer antigens are found on non-cancerous cells with the risk of off-tumor toxicities that cause serious complications that many times have led to morbidity and death. The powerful nature of T cell therapies is one of the reasons that T cells continue to be sought as a therapeutic, but have not yet reached FDA approval in the United States for any form of disease.

While many of the T cell clinical trials are showing strong benefit over standard of care, the cost of producing a T cell therapy and risk to the patient continues to hamper development of these technologies beyond a few specialized centers. Further limitations exist due to the complex immunosuppressive environment of the tumor, and difficulty of identifying appropriate tumor antigens. See Corrigan-Curay J, Kiem H P et al., *Molecular therapy: the Journal of the American Society of Gene Therapy* 2014, 22(9): 1564-1574. It should be noted that T cell therapeutics in cancer were initially developed for the treatment of melanoma and leukemia, and in the intervening quarter century have not significantly deviated from those cancer targets. Further improvements in the technical aspects of T cell therapy as well as continuing research and development of immune-modulatory drugs will continue to promote T cell cancer therapies for cancer and potentially broaden the applicability of these therapeutics.

Diseases of excessive inflammation are currently targeted by immune-modulatory or immune-suppressive medications. These therapies are often effective, but have untoward side effects as discussed in the above section. Better targeted immunosuppression may be possible using regulatory T cells ($T_{regs}$). As $T_{regs}$ are better understood and culturing techniques become more advanced, cell therapies based on reconstituting $T_{regs}$ will likely move toward clinical trials more rapidly. The use of $T_{regs}$ in clinical trials has been limited to preventing GvHD following hematopoetic stem cell transplantation (HSCT) for the most part. It is likely that the number of uses for $T_{reg}$ will expand as many other forms of inflammation have been targeted in preclinical models. Technical challenges related to the isolation and propagation of $T_{reg}$ is currently limiting the advance of this T cell therapy. See Singer B D et al., *Frontiers in immunology* 2014, 5:46.

The development of MHC independent T cell propagation methods has been a great technical advance for T cell therapies. Growing T cells by antigen-specificity-independent selection (ASIS) generates large numbers of T cells for reinfusion to a patient. While it might seem counterintuitive to grow T cells without direct selection for specificity, the large number of T cells can include an activated and propagated subset of T cells that are specific to the antigen targeted. Novel ASIS methods are sought to enhance the selection of transgenic T cells and to select for therapeutically useful T cell phenotypes. While in vitro ASIS using chimeric cytokine receptors is a recently reported method of non-immunogenic selection, it only utilizes the third signal in T cell activation—cytokine signaling. See Wilkie S et al., *The Journal of biological chemistry* 2010, 285(33):25538-25544. A strategy that can utilize the first and second signals of T cell activation (CD3 and costimulatory signaling) of human genes to activate and propagate T cells independent of antigen specificity can be of further benefit.

The adoptive transfer of antigen-specific T cells is a rapidly developing field of cancer immunotherapy with various approaches to their manufacture being tested and new antigens being targeted. T cells can be genetically-modified for immunotherapy to express chimeric antigen receptors (CAR) that recognize tumor-associated antigens (TAAs) independent of HLA (HLA is the human version of MHC) expression. Recent results from early-phase clinical trials demonstrate that CAR+ T-cell (CART) therapies can lead to partial and complete remissions of malignant diseases, including in some recipients with advanced/relapsed B-cell tumors. See Kalos M et al., *Science translational medicine* 2011, 3(95):95ra73 and Kochenderfer J N et al., *Blood* 2012, 119(12):2709-2720.

Therefore, notwithstanding what has previously been reported in the literature, there exists a need for improved methods of preparing transgenic T cells, propagating T cells for therapeutic treatments and selecting for regulatory T cells. Additionally, methods of making and using transgenic T cells and agents regulating the propagation and selection of transgenic T cells will greatly aid in the treatment of cancer, autoimmune diseases, infectious diseases and any number of other medical conditions in which the immune system plays a role.

SUMMARY OF THE INVENTION

In one aspect, an isolated transgenic mammalian T cell comprising or expressing a transgene and one or more of DHFR$^{FS}$ and TYMS$^{SS}$ is provided. In some embodiments, the isolated transgenic mammalian T cell comprises or expresses a transgene, DHFR$^{FS}$ and TYMS$^{SS}$. In some embodiments, the transgene is a suicide gene. In some embodiments, a suicide gene is further included. In some embodiments, codon optimization is performed on DHFR$^{FS}$, TYMS$^{SS}$, or both.

In another aspect is provided a method for inhibiting anti-thymidylate (AThy) toxicity in a mammalian T cell comprising expressing an anti-thymidylate resistance (AThyR) transgene in said mammalian T cell. In some embodiments, the AThyR transgene is DHFR$^{FS}$. In some embodiments, the AThyR transgene is TYMS$^{SS}$. In some embodiments, the transgene is a suicide gene. In some embodiments, a suicide gene is further included. In some embodiments, codon optimization is performed on DHFR$^{FS}$, TYMS$^{SS}$, or both.

In another aspect is provided a method for selecting a T cell expressing a transgene of interest. The method comprises applying a thymidine synthesis inhibitor to a plurality of T cells that comprises a T cell expressing the transgene of interest and DHFR$^{FS}$ and selecting for one or more T cells surviving after seven or more days of application of the thymidine synthesis inhibitor, wherein the one or more T cells expresses a vector comprising the transgene of interest and DHFR$^{FS}$. The thymidine synthesis inhibitor may be selected from the group consisting of methotrexate (MTX), 5-FU, Raltitrexed and Pemetrexed. In some embodiments, the transgene is a suicide gene. In some embodiments, a suicide gene is further included. In some embodiments, codon optimization is performed on DHFR$^{FS}$, TYMS$^{SS}$, or both.

Yet another aspect is a method for selectively propagating peripheral blood mononuclear cells (PBMC) resistant to MTX and 5-FU. The method comprises transfecting peripheral PBMC with a vector comprising an AThyR gene, treating the transfected PBMC with a thymidine synthesis inhibitor and selecting for PBMC that express the AThyR gene. In some embodiments of this aspect, the method further comprises propagating a T cell population from the transfected PBMC. In some embodiments, the thymidine synthesis inhibitor may be selected from the group consisting of methotrexate (MTX), 5-FU, Raltitrexed and Pemetrexed. In some embodiments, the thymidine synthesis inhibitor is MTX. In some embodiments, the AThyR gene is TYMS$^{SS}$. In some embodiments, the AThyR gene is DHFR$^{FS}$. In some embodiments, codon optimization is performed on DHFR$^{FS}$, TYMS$^{SS}$, or both.

Another aspect is an isolated transgenic mammalian T cell comprising a nucleic acid sequence comprising a transgene of interest and a nucleotide sequence encoding DHFR$^{FS}$ or TYMS$^{SS}$. In some embodiments, the isolated transgenic mammalian T cell comprises a nucleic acid comprising a transgene of interest and a nucleotide sequence encoding DHFR$^{FS}$, wherein the transgene of interest and the nucleotide sequence encoding DHFR$^{FS}$ are operably linked. In some embodiments, the isolated transgenic mammalian T cell comprises a nucleic acid comprising a transgene of interest and a nucleotide sequence encoding TYMS$^{SS}$, wherein the transgene of interest and the nucleotide sequence encoding TYMS$^{SS}$ are operably linked. In some embodiments, the transgene is a suicide gene. In some embodiments, a suicide gene is further included. In some embodiments, codon optimization is performed on DHFR$^{FS}$, TYMS$^{SS}$, or both.

In another aspect is provided an isolated transgenic mammalian T cell expressing a transgene and DHFR$^{FS}$, wherein the T cell comprises (1) a polynucleotide comprising sequence that encodes the transgene and (2) a polynucleotide comprising sequence that encodes the DHFR$^{FS}$. In some embodiments, the transgene is a suicide gene. In some embodiments, a suicide gene is further included. In some embodiments, codon optimization is performed on DHFR$^{FS}$.

In another aspect is provided an isolated transgenic mammalian T cell expressing a transgene and TYMS$^{SS}$, wherein said T cell comprises (1) a polynucleotide comprising sequence that encodes the transgene and (2) a polynucleotide comprising sequence that encodes the TYMS$^{SS}$. In some embodiments, the transgene is a suicide gene. In some embodiments, a suicide gene is further included. In some embodiments, codon optimization is performed on TYMS$^{SS}$.

In yet another aspect is provided a method of treating a patient with a cancer comprising administering to a patient a therapeutically effective amount of a T cell of an isolated T cell of any of the above embodiments.

In some embodiments, a combination therapy of AThyR$^+$ T cells with AThy therapies can be used to improve anti-tumor immunity. An isolated T cell with a AThyR-phenotype can be administered with MTX, 5-FU, Raltitrexed and Pemetrexed, or any other thymidine synthesis inhibitor.

In yet another aspect is provided a method for selecting for a T cell expressing a transgene of interest, as shown in any of the FIGS. or as described in the description.

In yet another aspect is provided a T cell, as shown in any of the FIGS. or as described in the description.

In another aspect is a method for selectively propagating human T cells resistant to one or more of MTX, 5-FU, Raltitrexed and Pemetrexed, as shown in any of the FIGS. or as described in the description. In some embodiments, the human T cells are primary human T cells.

Another aspect is a method of enriching for regulatory T cells in a population of T cells isolated from a mammal by contacting said population with a thymidine synthesis inhibitor selected from the group consisting of MTX, 5-FU, Raltitrexed and Pemetrexed, or a combination thereof, to selectively deplete effector T cells in the population. In some embodiments, the population of T cells isolated from a mammal is contacted with both MTX and 5-FU. In some embodiments, the T cells express one or more of DHFR$^{FS}$ and TYMS$^{SS}$. In some embodiments, the T cells express both DHFR$^{FS}$ and TYMS$^{SS}$. In some embodiments, codon optimization is performed on DHFR$^{FS}$, TYMS$^{SS}$, or both.

Another aspect is a method for depleting regulatory T cells in a population of T cells isolated from a mammal by culturing said population in the presence of one or more aminoglycosidases to selectively deplete the regulatory T cells in said culture. In some embodiments, the T cells express one or more of DHFR$^{FS}$ and TYMS$^{SS}$. In some embodiments, the T cells express both DHFR$^{FS}$ and TYMS$^{SS}$. In some embodiments, codon optimization is performed on DHFR$^{FS}$, TYMS$^{SS}$, or both.

Another aspect is a method for selecting for a regulatory T cell isolated from a mammal. The method comprises treating a plurality of T cells expressing one or more of DHFR$^{FS}$ and TYMS$^{SS}$ with a thymidine synthesis inhibitor and selecting a regulatory T cell that expresses a marker for a regulatory T cell. In some embodiments, the T cells express DHFR$^{FS}$. In some embodiments, the selecting step comprises cell isolating with magnetic bead sorting using one or more of an anti-CD4 antibody, an anti-CD25 antibody, an anti-CD3 antibody, an anti-CD8 antibody, an anti-CD25 antibody, an anti-CD39 antibody, an anti-CD45 antibody, an anti-CD152 antibody, an anti-KI-67 antibody, an anti-LAP antibody and an anti-FoxP3 antibody. In some embodiments, the thymidine synthesis inhibitor is selected from the group consisting of methotrexate (MTX), 5-FU, Raltitrexed or Pemetrexed. In some embodiments, the method further comprises treating the regulatory T cell with one or more of folate, leucovarin and FU.

In another aspect is provided a composition comprising a first plurality of T cells isolated from a mammal and a thymidine synthesis inhibitor. The first plurality of T cells is enriched for regulatory T cells as compared to a second plurality of T cells isolated from a mammal that does not comprise a thymidine synthesis inhibitor.

With the foregoing and other objects, advantages and features of the invention that will become hereinafter apparent, the nature of the invention may be more clearly understood by reference to the following detailed description of the preferred embodiments of the invention and to the appended claims.

In another aspect is provided an isolated transgenic mammalian T cell expressing a transgene and $DHFR^{FS}$, wherein the T cell comprises (1) a polynucleotide comprising sequence that encodes the transgene and (2) a polynucleotide comprising sequence that encodes the $DHFR^{FS}$. In some embodiments, codon optimization is performed on $DHFR^{FS}$ and/or the sequence encoding the transgene of interest. In some embodiments, the transgene of interest and the nucleotide sequence encoding $DHFR^{FS}$, upon expression, are encoded on the same mRNA. In further embodiments, the sequence encoding the transgene of interest and the nucleotide sequence encoding $DHFR^{FS}$ are separated by an internal ribosomal entry site (IRES) or a ribosomal slip sequence. In certain embodiments, the transgene of interest may encode a chimeric antigen receptor (CAR) construct, a T-cell Receptor (TCR), a hormone (e.g., glucagon), a cytokine, a chemokine, a suicide gene, a transcription factor or a cell surface polypeptide, such as a receptor (e.g., an integrin, cytokine receptor, chemokine receptor or hormone receptor).

In another aspect is provided an isolated transgenic mammalian T cell expressing a transgene and $TYMS^{SS}$, wherein said T cell comprises (1) a polynucleotide comprising sequence that encodes the transgene and (2) a polynucleotide comprising sequence that encodes the $TYMS^{SS}$. In some embodiments, codon optimization is performed on $TYMS^{SS}$ and/or the sequence encoding the transgene of interest. In certain embodiments, the transgene of interest and the nucleotide sequence encoding $TYMS^{SS}$, upon expression, are encoded on the same mRNA. In some embodiments, the sequence encoding the transgene of interest and nucleotide sequence encoding $TYMS^{SS}$ are separated by an IRES or a ribosomal slip sequence. In specific embodiments, the isolated transgenic mammalian T cell expressing a transgene and $TYMS^{SS}$ further comprises a nucleotide sequence encoding $DHFR^{FS}$(optionally, the nucleotide sequence encoding $DHFR^{FS}$ is operably linked to a second transgene of interest). In some embodiments, the transgene of interest (e.g., operably linked to $TYMS^{SS}$) is a growth factor, a CAR construct, a TCR, a hormone (e.g., glucagon), a cytokine, a chemokine, a suicide gene, a transcription factor (e.g., FoxP3) or a cell surface polypeptide, such as a receptor (e.g., an integrin, cytokine receptor, chemokine receptor or hormone receptor). In particular embodiments, the cytokine may be IL-12 or IL-15.

Yet a further aspect is a method for providing controlled expression of a first transgene comprising providing a transgenic mammalian cell comprising a nucleic acid comprising the first transgene operably linked to a nucleotide sequence encoding $TYMS^{SS}$, said cell further comprising a nucleotide sequence encoding $DHFR^{FS}$. In some embodiments, the first transgene and nucleotide sequence encoding $TYMS^{SS}$, upon expression, are encoded on the same mRNA. In further embodiments, the sequence encoding the first transgene and the nucleotide sequence encoding $TYMS^{SS}$ are separated by an IRES or a ribosomal slip sequence. In certain embodiments, the first transgene of interest is a growth factor, is a growth factor, a CAR construct, a TCR, a hormone (e.g., glucagon), a cytokine, a chemokine, a suicide gene, a transcription factor (e.g., FoxP3) or a cell surface polypeptide, such as a receptor (e.g., an integrin, cytokine receptor, chemokine receptor or hormone receptor). In particular embodiments, the cytokine may be L-12 or IL-15.

In further embodiments, the nucleotide sequence encoding $DHFR^{FS}$ is operably linked to a second transgene. In some embodiments, the second transgene and the nucleotide sequence encoding $DHFR^{FS}$, upon expression, are encoded on the same mRNA. In other embodiments, the sequence encoding the second transgene of interest and nucleotide sequence encoding $DHFR^{FS}$ are separated by an IRES or a ribosomal slip sequence. In certain embodiments, the second transgene is a suicide gene. In specific embodiments, the suicide gene is an inducible suicide gene. In particular embodiments, the suicide gene is an inducible Caspase 9. In some embodiments, the mammalian cell is a T-cell.

In another aspect is provided a recombinant nucleic acid molecule encoding $TYMS^{SS}$ and a first transgene coding sequence. In some embodiments, the sequence encoding $TYMS^{SS}$ and/or the sequence encoding the transgene of interest is codon optimized. In certain embodiments, recombinant nucleic acid is a DNA or a RNA (e.g., a mRNA). In some embodiments, the sequence encoding the transgene of interest and nucleotide sequence encoding $TYMS^{SS}$ are separated by an IRES or a ribosomal slip sequence. In some embodiments, the transgene of interest is a growth factor, is a growth factor, a CAR construct, a TCR, a hormone (e.g., glucagon), a cytokine, a chemokine, a suicide gene, a transcription factor (e.g., FoxP3) or a cell surface polypeptide, such as a receptor (e.g., an integrin, cytokine receptor, chemokine receptor or hormone receptor). In particular embodiments, the cytokine may be IL-12 or IL-15.

BRIEF DESCRIPTION OF THE DRAWINGS

The drawings are exemplary only, and should not be construed as limiting the invention.

FIG. 2A-I depicts experiments relating to viability of Jurkat cells given for DHFR$^{FS}$ (left), TYMS$^{SS}$ (right), and NeoR (center).

FIG. 2A-II depicts experiments relating to alternations of mean fluorescent intensity (MFI) of eGFP given for DHFR$^{FS}$ (left), TYMS$^{SS}$ (right), and NeoR (center).

FIG. 2B depicts a determination whether enhanced survival occurs when Raltitrexed and DHFR$^{FS}$ & TYMS$^{SS}$ were co-electroporated into Jurkat treated with Ral.

FIG. 2C depicts the correlation of expression of DHFR$^{FS}$ and TYMS$^{SS}$ plasmids that were independently expressed. Observations suggested that cells expressing DHFR$^{FS}$ & TYMS$^{SS}$ as independent plasmids have correlated expression of each plasmid. This could have implications in the co-regulation of DHFR$^{FS}$ with TYMS$^{SS}$ Hence, the MFI of eGFP and RFP were correlated for treatments with multiple concentrations of MTX, Pem, and Ral. The linear regression data is included in the FIG. Each experiment was independently repeated at least twice with 4-6 replicates. *=p<0.05, =p<0.01, *=p<0.001, ****=p<0.0001. There was observed improved expression over mock electroporated Jurkat, and a weak survival improvement in 5 μM 5-FU. Without wishing to be bound by theory, the lack of significantly enhanced survival is likely due to an alternative mechanism of 5-FU contributing to toxicity, which is likely the known inhibition of mRNA and rRNA synthesis by 5-FU See Longley D B, et al., *The Journal of biological chemistry* 2010, 285(16):12416-12425.

FIG. 3B-i shows the tracking of T cells for expression of AThyRs DHFR$^{FS}$-DG, TYMS$^{SS}$-TG, both [DG & TSR], and NeoR-NRG in the presence (day 2-14) then absence (day 14-35) of appropriate selection drug. All experiments contain 5-6 biological replicates with each experiment independently repeated two times. *=p<0.05; =p<0.01; *=p<0.001; ****=p<0.0001.

FIG. 3B-ii shows the percentage of T cells shown in FIG. 4B-I that express co-receptor CD4.

FIG. 3C-i shows the tracking of T cells for expression of Myc-ffLuc-2A-NeoR (NRF) combined with each AThyR transgene [DG & NRF], [TSG & NRF], and [DG & TSR & NRF] in order to improve selection for AThyRs selected by 5-FU. Selection occurred under the same condition as FIG. 4B-I, with the exception that 100 IU IL-2/mL was added to promote outgrowth of cells treated with G418 All experiments contain 5-6 biological replicates with each experiment independently repeated two times. *=p<0.05; =p<0.01; *=p<0.001; ****=p<0.0001.

FIG. 3C-ii shows the percentage of T cells shown in FIG. 4C-I that express co-receptor CD4.

FIG. 3D-i shows that to elucidate the influence of 5-FU and TYMS$^{SS}$ on the selection of DHFR$^{FS}$, RFP or TYMS$^{SS}$-RFP (TSR) that were co-electroporated into T cells with DHFR$^{FS}$. All experiments contain 5-6 biological replicates with each experiment independently repeated two times. *=p<0.05; =p<0.01; *=p<0.001; ****=p<0.0001.

FIG. 3D-ii shows the percentage of T cells shown in FIG. 4D-I that express co-receptor CD4.

FIG. 4A, AThyR and NeoR electroporated primary T cells were compared on Day 21 to mock-electroporated T cells treated with the same conditions. Each experiment was independently repeated at least twice with 5-6 replicates. *=p<0.05, **=p<0.01.

FIG. 4B-I depicts the continued propagation of the experiment of FIG. 5A on day 35. Each experiment was independently repeated at least twice with 5-6 replicates. *=p<0.05, **=p<0.01.

FIG. 4B-II depicts the day 35 changes in outgrowth potential for primary T cells when NeoR is combined with DHFR$^{FS}$ and/or TYMS$^{SS}$. Each experiment was independently repeated at least twice with 5-6 replicates. *=p<0.05, **=p<0.01.

FIG. 4C shows the influence of 5-FU on preserving outgrowth potential for primary T cells on day 35. Each experiment was independently repeated at least twice with 5-6 replicates. *=p<0.05, **=p<0.01.

FIG. 5A Jurkat cells were genetically-modified to express FLAG-DHFR$^{FS}$-2A-eGFP pSBSO (D$^{FS}$G) with resistance to MTX (n=4), codon optimized (CoOp) D$^{FS}$G—with known mRNA binding elements D$^{FS}$G removed (n=5), and [D$^{FS}$G & FLAG-TYMS$^{SS}$-2A-RFP pSBSO (TS$^{SS}$R)]— with enhanced resistance to MTX beyond D$^{FS}$G alone through the addition of MTX resistant TYMS$^{SS}$ (n=7). Genetically-modified Jurkat cells were selected for 2 weeks in 1 μM MTX before culturing without MTX for 3-5 weeks. The stable fluorescent protein expression, in the absence of MTX, is depicted by mean fluorescence intensity (MFI).

FIG. 5B-I Jurkat cells were treated for 72 hours with 0.5 μM MTX or no treatment. The MFI difference (Δ=eGFP MFI MTX treated–eGFP MFI untreated) is depicted.

FIG. 5B-II a representative histogram demonstrates the MTX induced change in eGFP MFI for DHFR$^{FS}$ (left peak) and CoOp DHFR$^{FS}$ (right peak) in Jurkat.

FIG. 5C-D in primary T cells, transgenes DHFR$^{FS}$, TYMS$^{SS}$, or the combination were selected for 2 weeks in the presence of cytotoxic drug and then propagated without selection for 3 weeks (see examples). On day 35, T cells were stimulated with anti-CD3, anti-CD28 antibodies, and 50 IU/mL IL-2 in the presence or absence of MTX. The fluorescent protein MFI of untreated cells is shown in FIG. 5C, and FIG. 5D-I depicts the Δ MFI after 72 hours of treatment with 0.5 μM MTX in comparison to no treatment.

FIG. 5D-II, shows a representative histogram, which demonstrates the observed shift in eGFP fluorescence for DHFR$^{FS}$+ T cells in the presence or absence of MTX (n=5). (No DNA=far left peak; D$^{FS}$G & NRF, No Trx=upper center peak; D$^{FS}$G & NRF, MTX=upper right peak; D$^{FS}$G & TS$^{SS}$R, No Trx=lower center and lower right peak, D$^{FS}$G & TS$^{SS}$R. MTX=lowest peak)

FIG. 5E, a trans regulatory pattern of DHFR and TYMS linked fluorescent proteins was observed. A representative flow plot from the 1 μM MTX selected Jurkat left untreated in (5A) demonstrates that unselected mock-electroporated (No DNA—lower left cluster) Jurkat and D$^{FS}$G+ Jurkat (lower right cluster) have a globular appearance in the RFP channel, while co-expression of DHFR$^{FS}$ with TYMS$^{SS}$ in [D$^{FS}$G & TS$^{SS}$R]+ Jurkat leads to a linear clustering (upper right cluster).

FIG. 5F T cells were electroporated with DHFR$^{FS}$ and co-transformed with either RFP control or FLAG-TYMS$^{SS}$-2A-RFP pSBSO (TS$^{SS}$R) before propagation as before (in 5C) with selection in 0.1 μM MTX from days 2-14 before continued propagation in the absence of MTX. A representative flow plot of primary human T cells from the same donor where [D$^{FS}$G & RFP (cluster on the far right)], [D$^{FS}$G & TS$^{SS}$R (upper right cluster)], and untransformed T cells (lower left quadrant) are shown on day 21. A linear clustering of DHFR$^{FS}$ is again noted when co-expressed with TYMS$^{SS}$ that is not noted with RFP alone.

FIG. 5G further studies to identify a trans pattern of linked expression between DHFR$^{FS}$ and TYMS$^{SS}$ were identified in the selection of [D$^{FS}$G & TS$^{SS}$R] electroporated Jurkat in anti-folates MTX [0, 0.01, 0.1, 0.5, 1, 5 μM], pemetrexed [0, 10, 50, 100 μM], and raltitrexed [0, 1, 5, 10 μM]. The MFI of D$^{FS}$G and TS$^{SS}$R for each expression pattern was plotted after day 2-14 in selection. The values are plotted and a linear fitting was performed with the R$^2$ from the Pearson's correlation and the slope of the linear regression provided on the graph. This data is assembled from 4 technical replicates.

FIG. 5H depicts a model of post-transcriptional regulation of DHFR and TYMS. All experiments other than that depicted in FIG. 5G were independently repeated twice. Kruskall-Wallis test was used to determine significant differences with multivariate analyses; *=p<0.05, =p<0.01, *=p<0.001, ****=p<0.0001. TMP—thymidine monophosphate; UMP—uridine monophosphate; DHF—dihydrofolate; THF—tetrahydrofolate; 5, 10-methylenetetrahydrofolate (5, 10 CH2THF).

FIGS. 5I-5L, shows co-expression of DHFR$^{FS}$ with TYMS$^{SS}$ leads to controlled expression of TYMS$^{SS}$ and cis transgenes in the presence of MTX.

FIGS. 5I-5J, T cells from the experiment described in FIG. 5F were propagated to day 35. T cells were stimulated for 72 hours with anti-CD3, anti-CD28 antibodies, 50 IU/mL IL-2, and varying concentrations of MTX. The MTX induced change in eGFP MFI for DHFR$^{FS}$ is shown in (5I), while the influence of MTX on RFP and RFP co-expressed with TYMS$^{SS}$ (TS$^{SS}$R) is shown in (5J) (n=6, repeated independently twice, analyzed by Two-Way ANOVA with Sidak's multiple comparison test).

FIG. 5K, this regulatory pattern was applied to a clinically relevant problem: The cytokine interleukin-12 (IL-12) is a strong promoter of anti-tumor activity in T cells, but is highly toxic. A construct expressing IL-12 following TYMS$^{SS}$, called TS$^{SS}$IL-12, was used to modulate IL-12 expression in conjunction with the construct D$^{FS}$iC9. D$^{FS}$iC9 is capable of selecting T cells with DHFR$^{FS}$ or depleting T cells with inducible caspase 9 (iC9). A representative flow diagram of the same donor depicts intracellular expression of IL-12 and c-Myc-iC9 in [DFSiC9 & TS$^{SS}$IL-12]—expressing T cells. These cells are shown on day 21 after selection from day 2-14 in 0.1 μM MTX and subsequent treatment with 0.5 μM MTX (right cluster) or no treatment (left cluster) from days 14-21. Cellular excretion of IL-12 was blocked for 6 hours before intracellular staining. Gating is based on staining of untransformed, unselected T cells stained in the same way.

FIG. 5L, three donors were treated as in (K) and the change in transgene expression noted after 7 days of treatment with 0.5 μM MTX is shown. Each measure was analyzed by t-tests ns=not significant; *=p<0.05, =p<0.01, *=p<0.001, ****=p<0.0001.

FIG. 6 depicts flow plots of transgene expression for AThyR experiments on day 35. Flow plots of CD4 and GFP expression depict day 35 of a series of experiments designed to characterize the selection and maintenance of transgene expression in donor T cells. T cells grown for 35 days with days 2-14 in the presence of cytotoxic drugs MTX, 5-FU, G418, or a combination, as noted above the flow plot.

FIG. 7 depicts AThyR rescue of AThyR+ and AThyR$^{neg}$ T cells following 72 hours treatment in MTX. T cells from the experiment described for FIG. 3D were stimulated on day 35 with anti-CD3, anti-CD28, and IL-2 along with varying doses of MTX [0, 0.1, 0.5, 1 μM] for 72 hours.

Figure 8A:
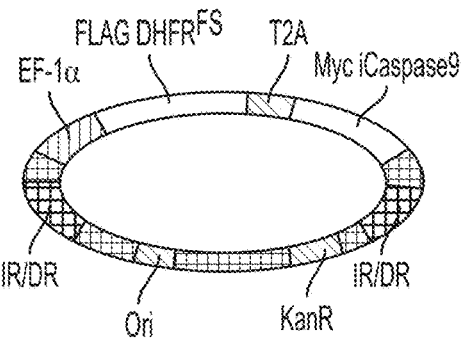
FIG. 8A shows a construct in which the suicide gene inducible caspase 9 (iC9) was designed to express with DHFR$^{FS}$ in the plasmid DFSiC9 shown in (A).
Figure 8B:
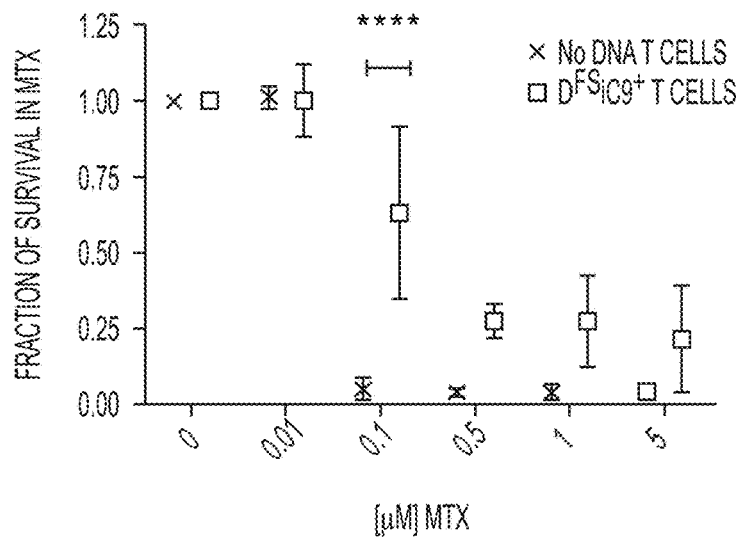
FIG. 8B shows the testing of the construct depicted in FIG. 8A in PBMC of 3 healthy donors stimulated with a 1:1 ratio of OKT3-loaded AaPC and treated with MTX from day 2 until day 7 when survival is shown.
Figure 8C:
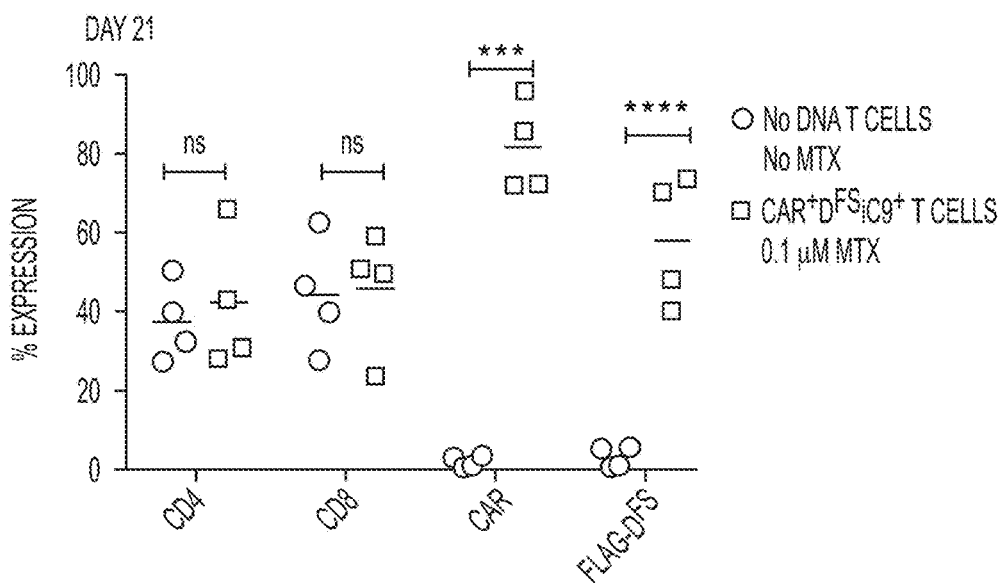
FIG. 8 depicts an example that AThyRs select for transgenes of interest. Increased selection of DHFR$^{FS}$ is desirable for difficult to isolate genes of interest, such as suicide genes.

FIG. 8C shows T cells were electroporated with CD19-specific chimeric antigen receptor (CAR), $D^{FS}iC9$, and SB transposase and expanded on CARL$^+$ K562 in the presence of MTX for 21 days to select for each transgene, with CARL an acronym for ligand for CAR. The expression of costimulatory T cell receptors CD4, CD8, and transgenes CAR and DHFR$^{FS}$ are shown in 21 day CARL expanded transgenic T cells in comparison to mock electroporated T cells expanded on OKT3-loaded AaPC clone.4. Experiments were performed with 4 normal donors and repeated twice. Significance for each comparison was initially determined by Two-Way ANOVA followed by Sidak's post-hoc analysis; *=p<0.05, =p<0.01, *=p<0.001, ****=p<0.0001.

Figure 8D:
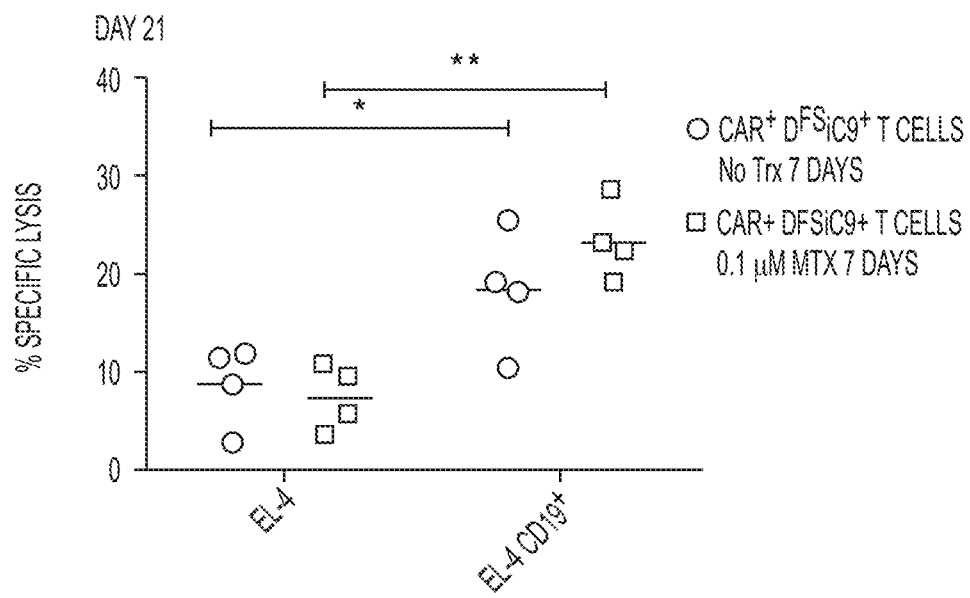

FIG. 8D shows the effect of MTX on cytotoxicity in DHFR$^{FS+}$ CAR$^+$ T cells was tested by stimulating CAR$^+$ T cells in the presence or absence of MTX for 7 days after stimulation on day 14. Cytotoxicity was assessed by chromium release assay (CRA) on Day 21 using CD19 positive or CD19 negative murine lymphoma EL-4 cells. T cells were co-incubated with EL-4 at a 1 target: 5 effector ratio. Experiments were performed with 4 normal donors and repeated twice. Significance for each comparison was initially determined by Two-Way ANOVA followed by Sidak's post-hoc analysis; *=p<0.05, =p<0.01, *=p<0.001, ****=p<0.0001.

Figure 8E:
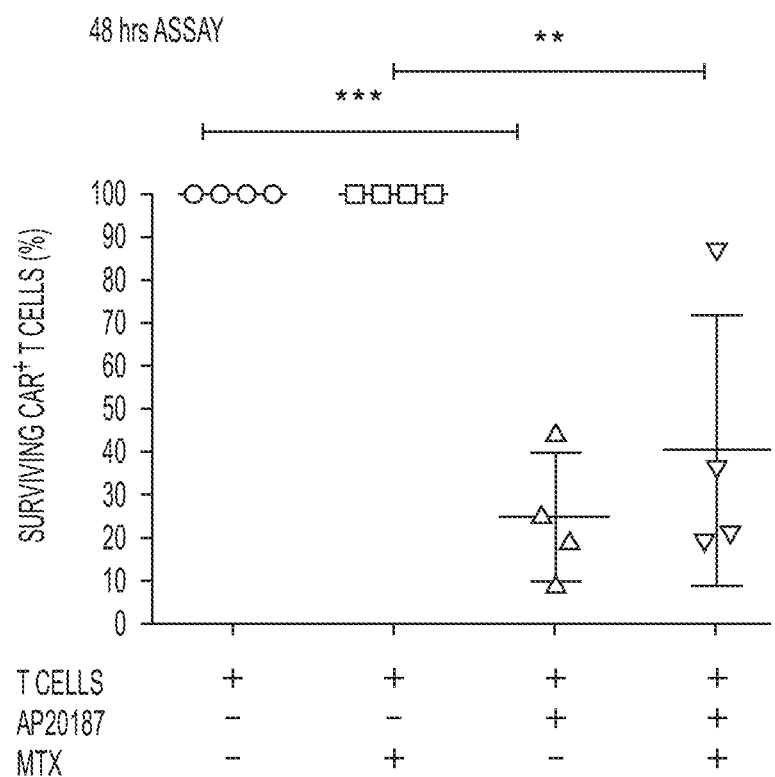

FIG. 8E shows the assessment of the functionality of iC9 on day 21 by resting T cells for 48 hours in 10 nM AP20187. T cells had previously been stimulated for 7 days in the presence or absence of MTX. Comparison of surviving CAR$^+$ T cells is made to matched, un-treated cells. Experiments were performed with 4 normal donors and repeated twice. Significance for each comparison was initially determined by Two-Way ANOVA followed by Sidak's post-hoc analysis; *=p<0.05, =p<0.01, *=p<0.001, ****=p<0.0001. Co-expressing DHFR$^{FS}$ with iC9 rather than CAR added the potential to ablate T cells through the addition of iC9 chemical inducer of dimerization AP20187. The addition of AP20187 significantly depleted resting CAR$^+$ T cells independent of MTX. This demonstrates that $D^{FS}iC9$ can select for iC9 expression and deplete genetically-modified T cells as necessary. The use of DHFR$^{FS}$ has the advantage of selecting transgene expression in T cells independent of antigen-specificity and antigen expression, making DHFR$^{FS}$ a more portable tool for use in a variety of T cell studies.

FIG. 9 depicts that post-transcriptional regulation of thymidine synthesis locks expression of DHFR to TYMS. MTX-induced increases in DHFR expression were inhibited by restoration of thymidine synthesis (TMP—thymidine monophosphate from UMP—uridine monophosphate). Likewise, MTX-induced decreases in TYMS expression were restored to normal levels by the restoration of DHFR activity reducing DHF—dihydrofolate to THF-tetrahydrofolate.

FIG. 10 shows that the drug selection of TCD4, FoxP3 by MTX occurs in part through toxicity. The known selection of $T_{CD4, FoxP3}$ by MTX was analyzed by targeting enzymes that contribute to the action of MTX. As $T_{CD4, FoxP3}$ are a rare component of PBMC, drug based inhibition was originally sought to analyze the phenomenon. Multiple drugs with actions similar to MTX were used to assay for the selection of $T_{CD4, FoxP3}$. In this case, γ-irradiation, G418, and cisplatin (CDDP) were used for controls as none of those treatments act on the known enzymatic targets of MTX.

FIG. 10A shows the association of each drug to the enzyme targets of MTX.

FIG. 10B-I shows PBMC stimulated with anti-CD3/CD28 and soluble human IL-2 were given lethal doses of each treatment and assayed after 7 days for viability.

FIG. 10B-II shows that these treatments resulted in variable selection for $T_{CD4, FoxP3}$ on day 7. The inability of folate analogs targeting DHFR, TYMS, or GARFT to significantly select for $T_{CD4, FoxP3}$ suggested that inhibition of AICARtf/inosine monophosphate (IMP) cyclohydrolase (ATIC) contributes to this selection. A dose dependence study followed analyzing the contribution of ATIC inhibitor in the selection of $T_{CD4, FoxP3}$. The study in B-II noted that G418 depleted $T_{CD4, FoxP3}$, thus, this was used as a negative control while the known selection of $T_{CD4, FoxP3}$ by rapamycin (Rapa) was a positive control. A non-folate analog known to inhibit ATIC (iATIC) was used as a specific inhibitor of ATIC.

FIGS. 10C-I, 10D-I, 10E-I and 10F-I show the cytotoxicity of G418 (C-I), MTX (D-I), iATIC (E-I), and Rapa (F-I).

FIGS. 10C-II, 10D-II, 10E-II and 10F-II show the selection for TCD4, FoxP3 for G418 (C-II), MTX (D-II), iATIC (E-II), and Rapa (F-II).

Figures 10E, 10F:
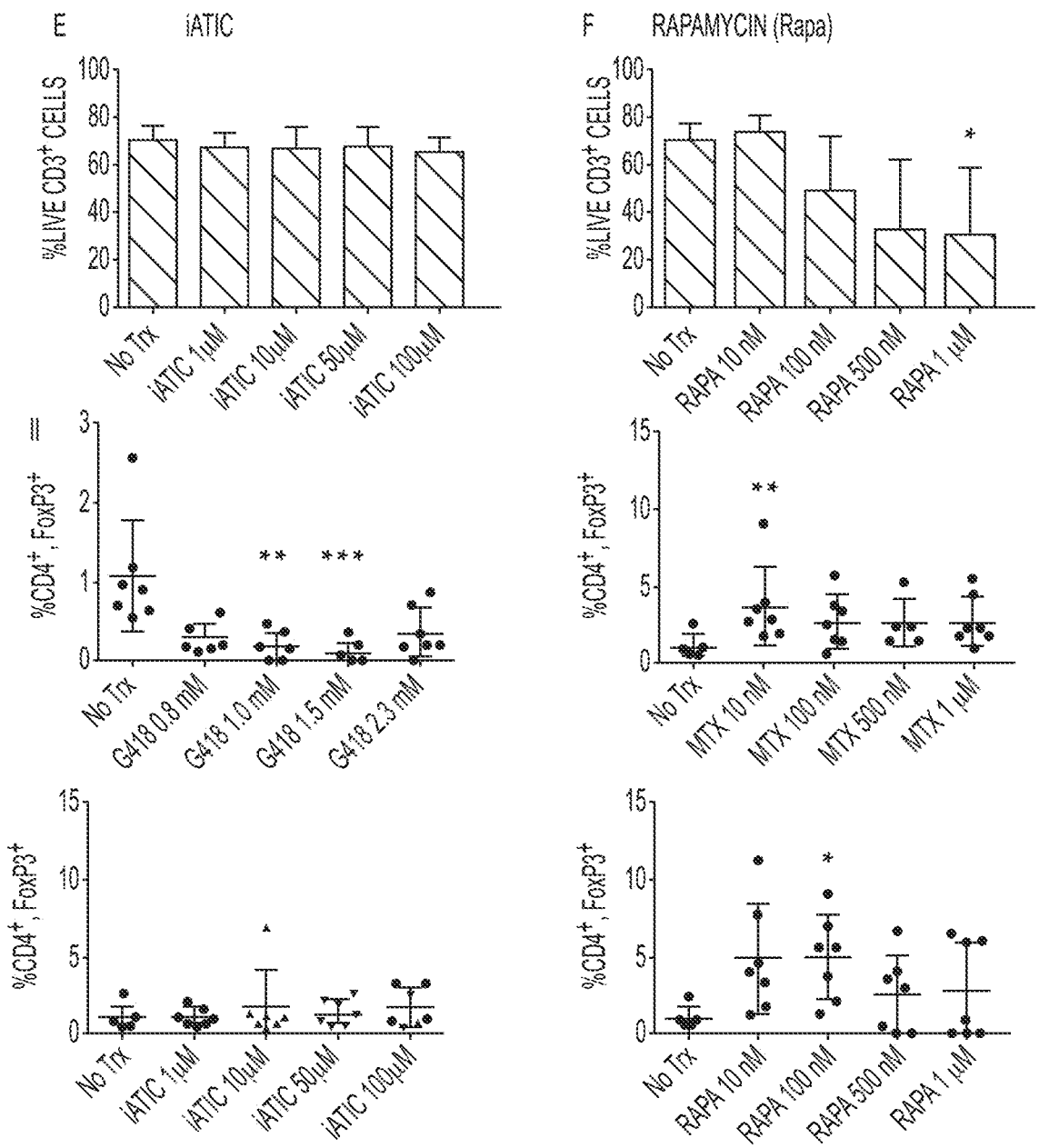
Figure 10G:
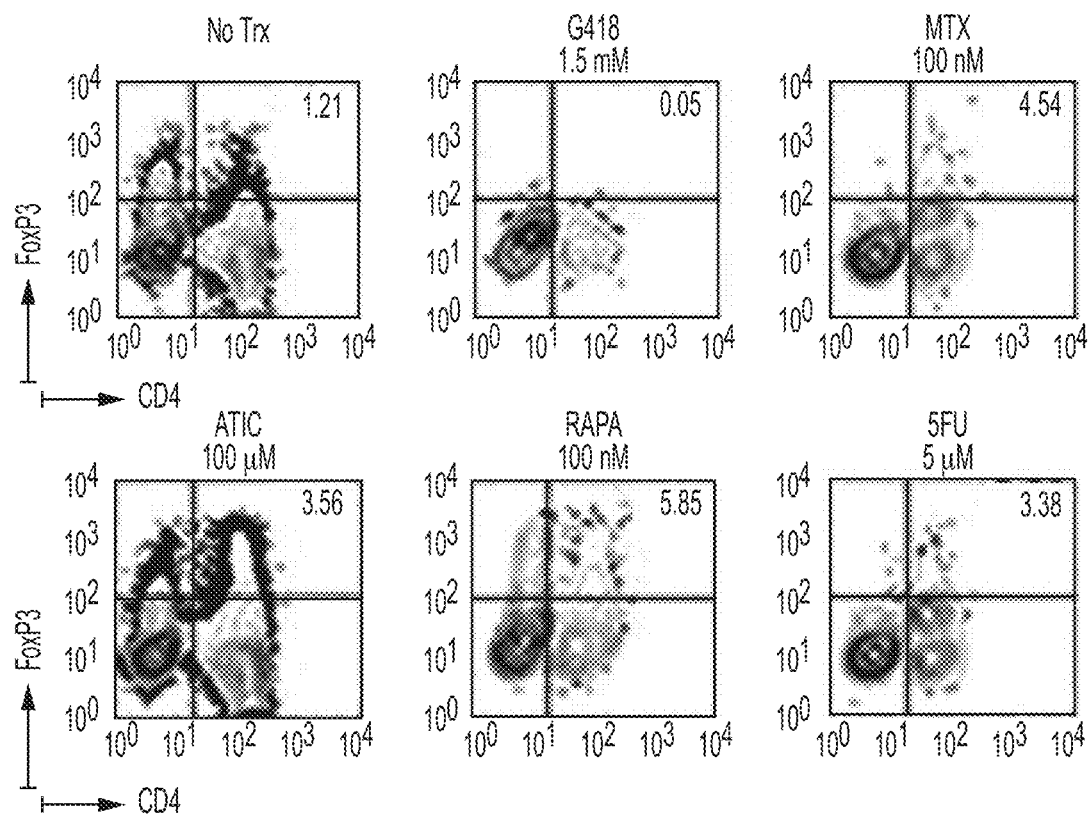

FIG. 10G depicts flow plots for CD4 and FoxP3 expression. FoxP3 expression was enhanced by iATIC similar to the action of Rapa, suggesting that MTX selection relies in part on cytotoxicity and in part by inhibition of ATIC to enhance selection of $T_{CD4, FoxP3}$. All assays used 4-7 donors independently repeated 2-3 times. Statistical significance was assessed using One-Way ANOVA for viability and Kruskall-Wallis test for percentage of $T_{CD4, FoxP3}$; *=p<0.05, =p<0.01, *=p<0.001, ****=p<0.0001.

FIG. 11 shows correlative findings in the selection of Tregs from primary T cells through resistance to the anti-DHFR and anti-TYMS actions of MTX.

Figure 11A:
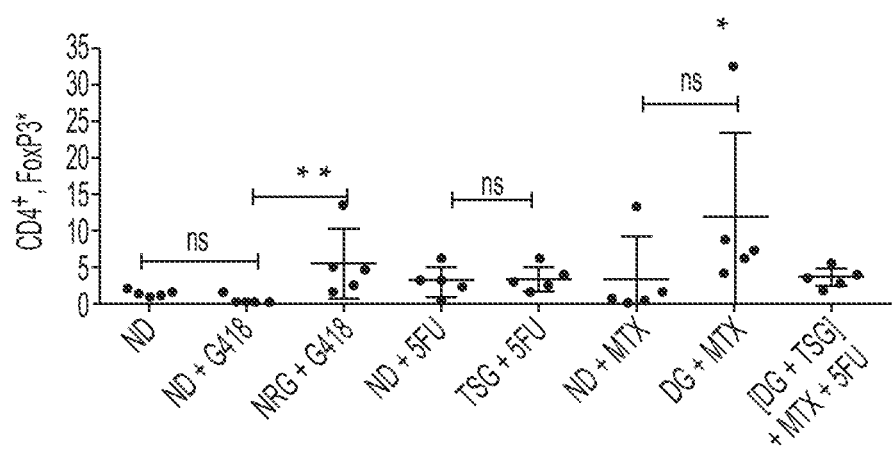

FIG. 11A shows the selection of TCD4, FoxP3 was assessed at day 21 in each experiment. Selection of TCD4, FoxP3 was assessed at day 21 in each experiment. The selection of $T_{CD4, FoxP3}$ in the experiment corresponding to column I of FIG. 2 is shown in A. It is notable for the rescue of $T_{CD4, FoxP3}$ with NeoR and early selection of $T_{CD4, FoxP3}$ with MTX selection of DHFR$^{FS}$.

Figure 11B:
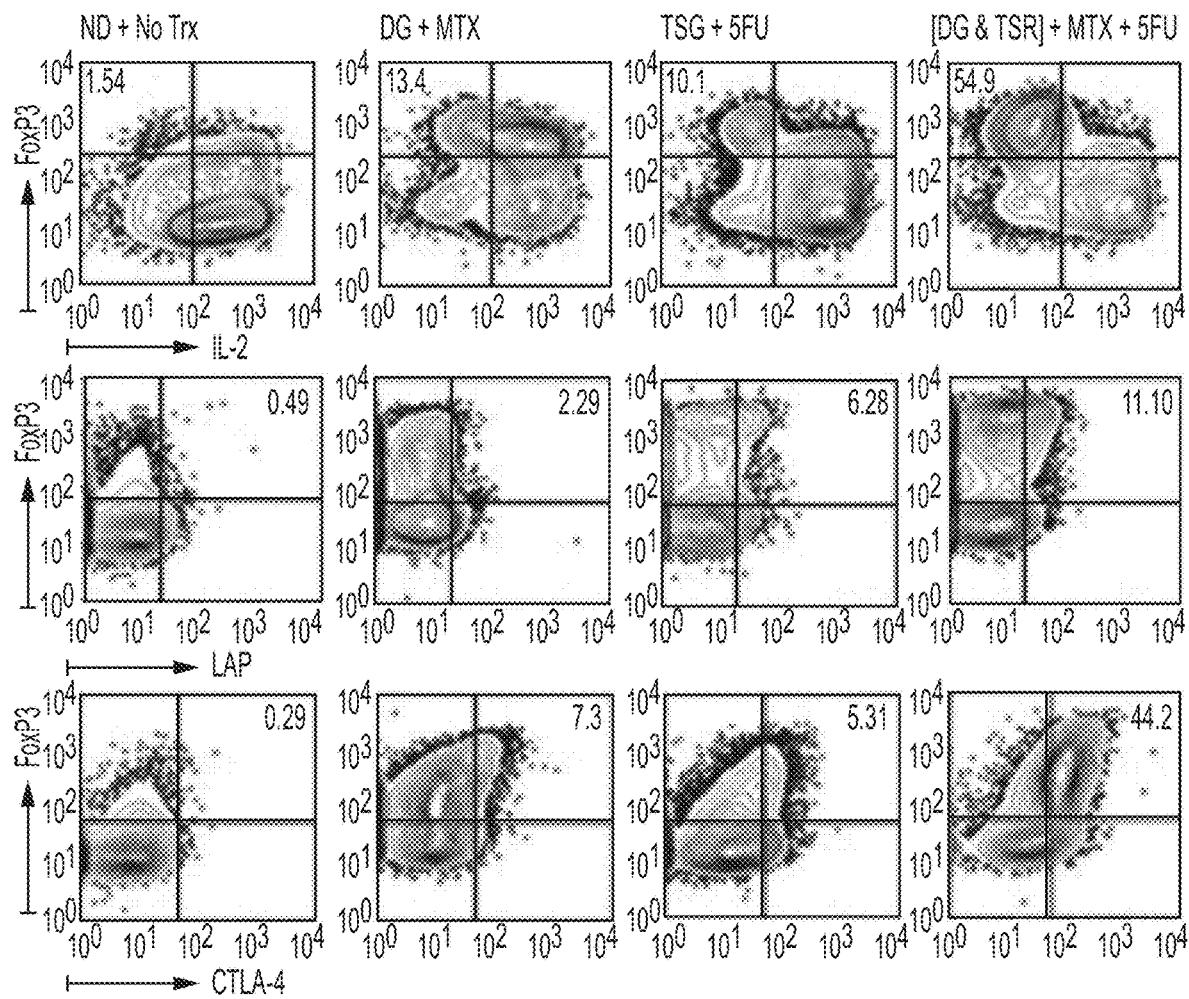

FIG. 11B shows flow plots in which FoxP3 is co-expressed with IL-2 in the top row, LAP in the middle row or CTLA-4 in the bottom row for the same experiment after stimulation on Day 35. This experiment utilized 5 donors and was independently repeated twice. Significance was assessed by Two-Way ANOVA and Sidak's post-hoc; *=p<0.05, **=p<0.01.

FIGS. 12A-D show that primary T cells resistant to the anti-DHFR and anti-TYMS actions of MTX preferentially expand Tregs. Primary T cells were electroporated with DHFR$^{FS}$ and TYMS$^{SS}$ transgenes resistant to the anti-DHFR and anti-TYMS actions of MTX, respectively, in order to assess the contribution of each pathway to the selection of $T_{CD4, FoxP3}$. T cells were electroporated with plasmids expressing drug resistant transgenes and stimulated with artificial antigen presenting cells (AaPCs) weekly at a 1:1 ratio. T cells were selected for 2 weeks in the combined with TYMS$^{SS}$-2A-RFP (TSR) and selected using both MTX and 5FU, or control selection vector NeoR-2A-GFP (NRG) selected with G418. Selection of TYMS$_{SS}$ by 5-FU was incomplete. Thus, ffLuc-2A-NeoR (NRF) vector was included with the MTX resistant transgenes DG, TSG, or [DG & TSR] to remove untransformed T cells in the experiments shown in column II. Equivalent selection for each transgene showed that MTX enhanced selected for $T_{reg}$ in the presence of MTX resistant DHFR. It was still uncertain whether the enzymatic activity of TYMS or 5-FU played a part in the selection of $T_{reg}$. Therefore, the experiment shown in column III was performed to test the influence of TYMS inhibition in the selection of $T_{reg}$. Selection of $T_{reg}$ phenotype was found to be associated with 5-FU, but independent of TYMS activity. The Kruskall-Wallis test was used to assess differences between groups for 5-6 biologic replicates and tests were independently repeated twice; *=p<0.05, **=p<0.01.

Figure 13:
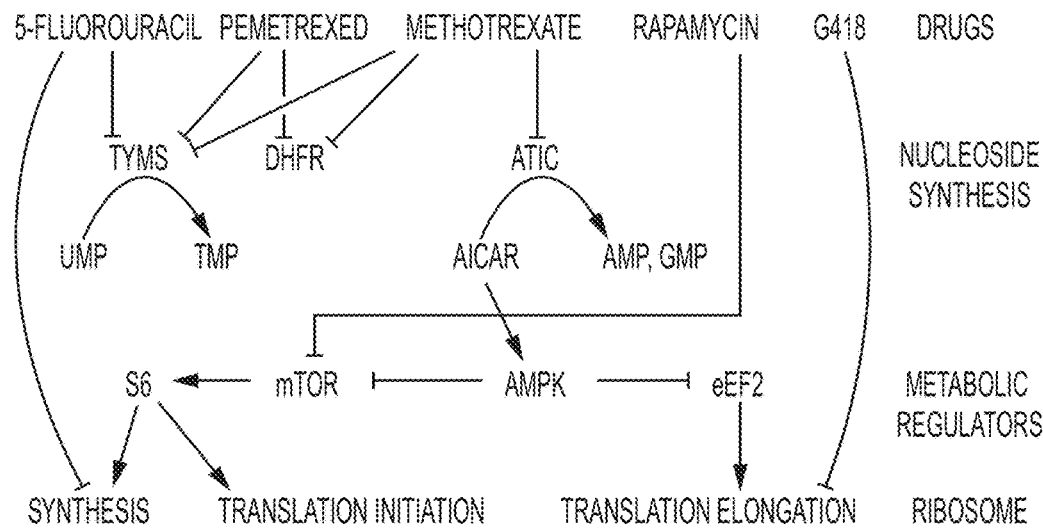

FIG. 13 is a diagrammatic representation of biochemical and protein interactions thought to influence selection of $T_{reg}$.

FIG. 14 shows that ribosomal Inhibition by aminoglycoside G418 selectively depletes replicating $T_{CD4, FoxP3}$.

Figure 14A:
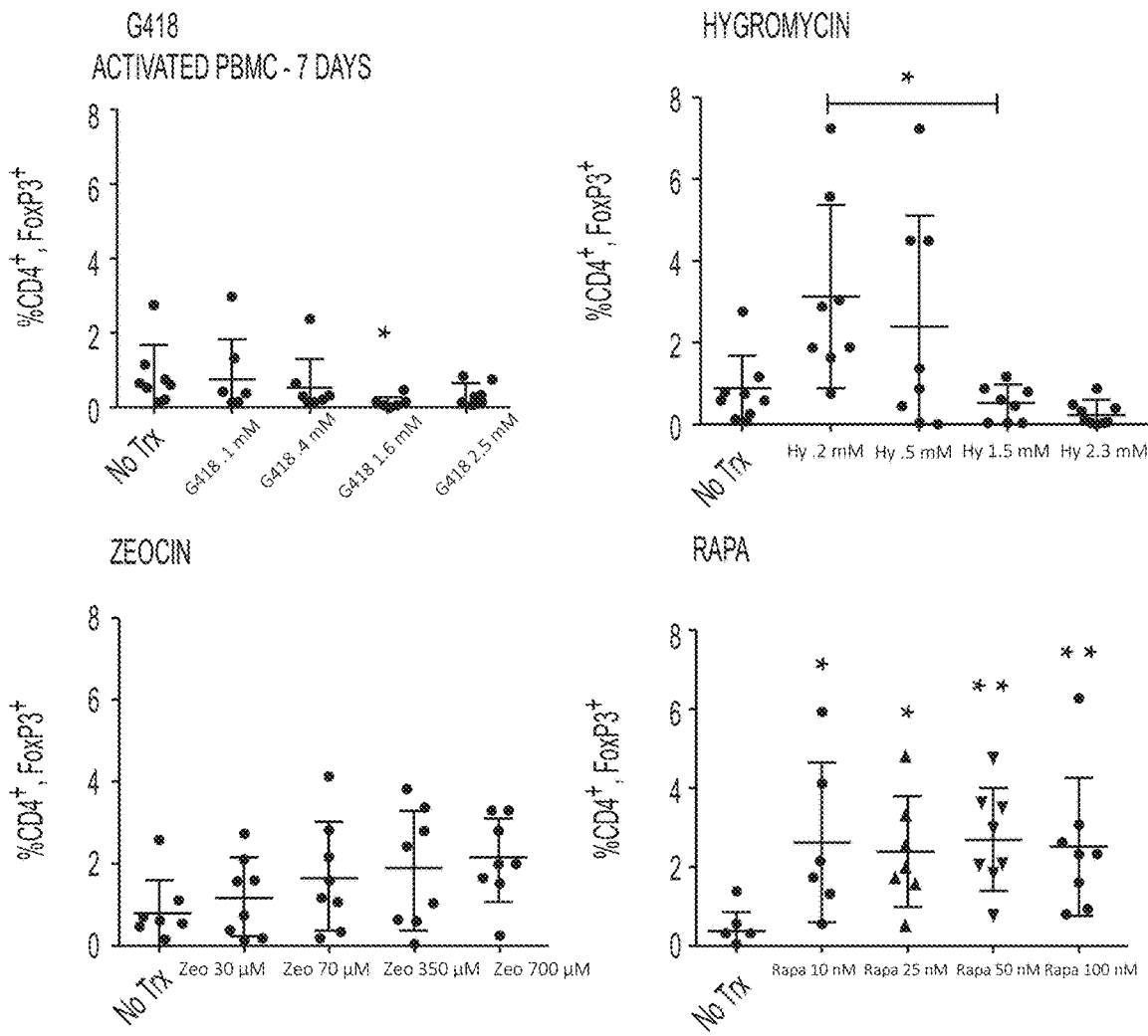

FIG. 14A shows that thawed PBMC were stimulated with anti-CD3/CD28 and IL-2 in the presence of increasing concentrations of G418, hygromycin, zeocin, or rapamycin for 7 days and the selection for $T_{CD4, FoxP3}$.

Figures 14B, 14C, 14D, 14E:
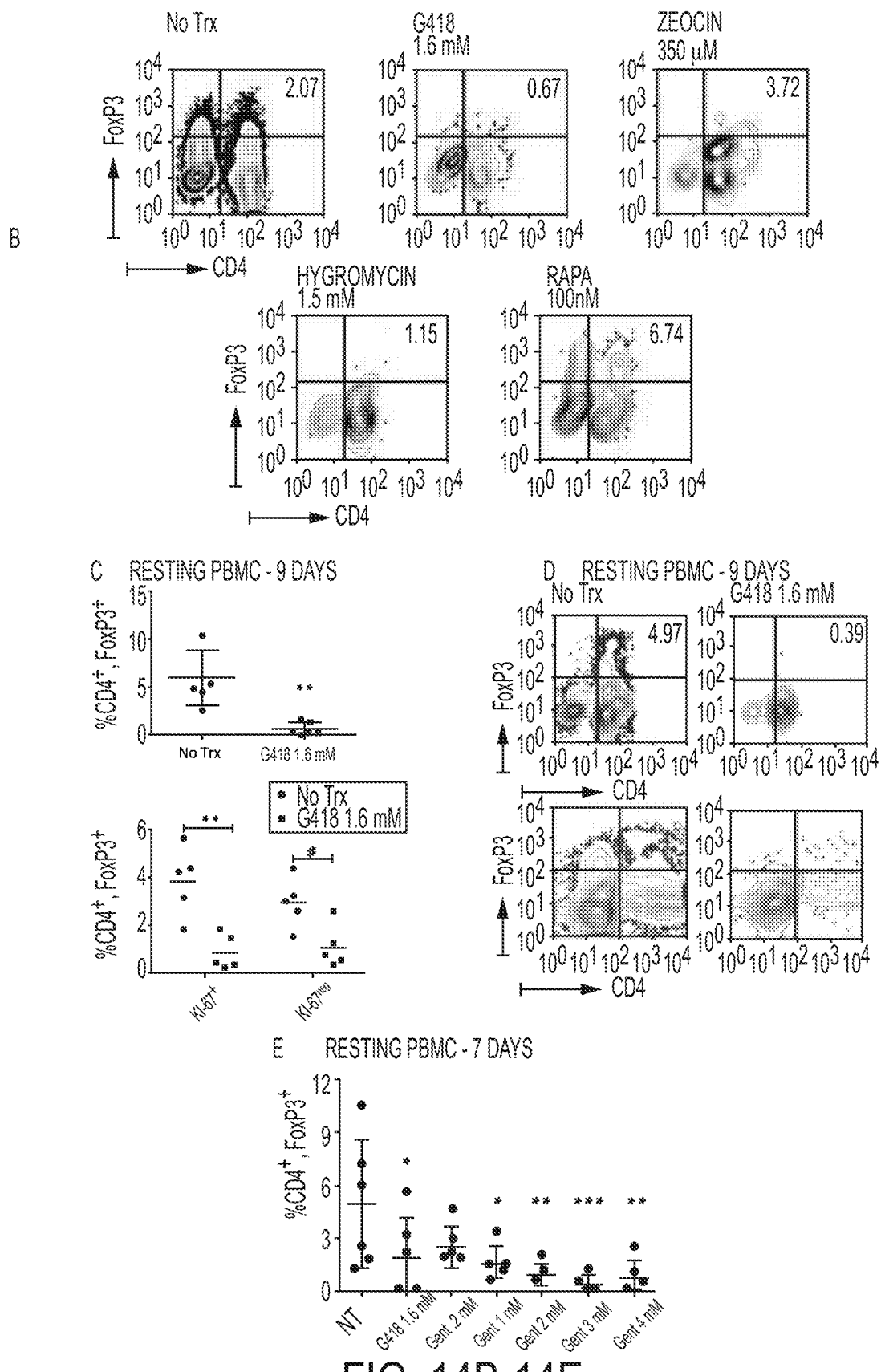

FIG. 14B shows flow plots of FoxP3 and CD4 expression, which in turn show the representative trends for one donor following the use of each drug.

FIG. 14C, the top panel shows the loss of $T_{CD4, FoxP3}$ was tested in unstimulated, thawed PBMC over the course of 9 days with or without G418 while the bottom panel shows the effects of G418 on proliferating and non-proliferating $T_{CD4, FoxP3}$ as indicated by Ki-67.

In FIG. 14D, representative flow plots for one donor demonstrate the effect of G418 on CD4 and FoxP3 expression in the top panel while FoxP3 and Ki-67 expression are shown in the bottom panel Gentamicin is an FDA approved aminoglycoside antibiotic and was subsequently tested in comparison to G418 for depletion of $T_{CD4, FoxP3}$ over a 7 day period. All experiments were performed with 6 normal donors and repeated independently twice.

FIG. 14E depicts the depletion of $T_{CD4, FoxP3}$ in resting PBMC after 7 days from gentamicin, an aminoglycosin, and demonstrates the action of aminoglycosides in depleting $T_{CD4, FoxP3}$. It was next tested whether depletion of $T_{CD4, FoxP3}$ corresponded with a loss of $T_{reg}$ marker expression or selective $T_{reg}$ toxicity.

FIG. 15 shows the effects of MTX, 5-FU, and G418 in sorted $T_{reg}$.

Figures 15A, 15B, 15C, 15D:
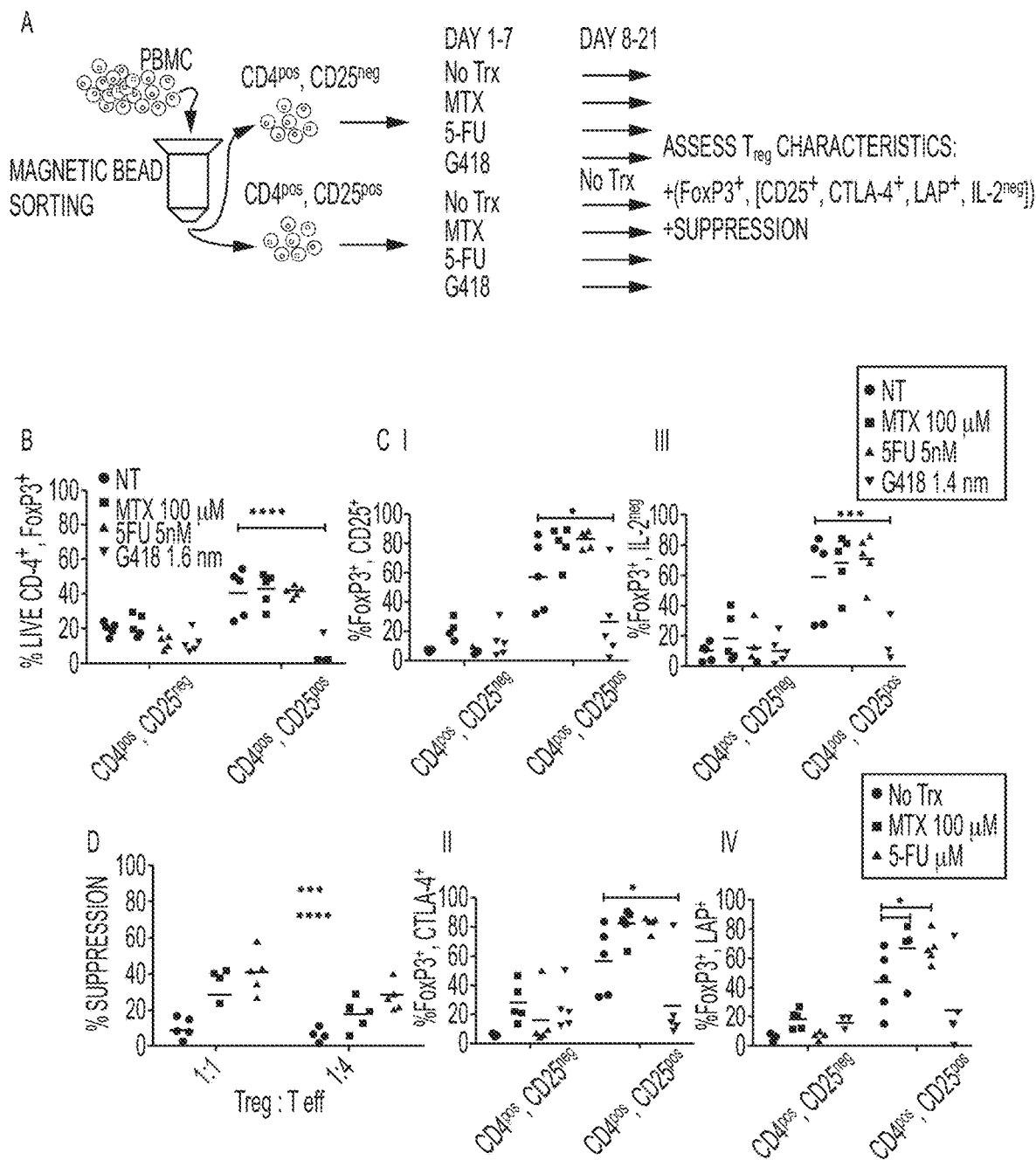

FIG. 15A diagrammatically shows the $T_{reg}$ and $T_{eff}$ were treated with MTX, 5-FU, or G418 as before for 7 days before stimulating without drug for the remaining 2 weeks of the experiment.

FIG. 15B shows an assessment of markers and activity of $T_{reg}$ on Day 21 to determine the contribution of each drug to selection or depletion of $T_{reg}$, and the live $T_{CD4, FoxP3}$ on Day 21 are shown in B.

FIG. 15C shows that after stimulating with soluble anti-CD3/CD28 and IL-2 for 48 hours T cells were assessed for co-expression of FoxP3 with CD25 in C-I, FoxP3 with CTLA-4 in C-II, and FoxP3 with LAP in C-IV. Six hours of stimulation with PMA/ionomycin was used to assess loss of IL-2 secretion in FoxP3 expressing T cells, C-III. A 72 hour suppression assay was performed by mixing treated $T_{reg}$ with untreated $T_{eff}$ and looking at uptake of [$^3$H] Thymidine at two separate concentrations, shown in D. This experiment was performed with 5 normal donors and repeated twice. All experiments were assessed with Two-Way ANOVA and significance was determined by Sidak's post-hoc analysis, *=p<0.05, =p<0.01, *=p<0.001, ****=p<0.0001.

FIG. 16 shows that stimulation of $T_{CD4, FoxP3}$ enhances adenosine monophosphate (AMP) Kinase (AMPK) activation and leads to inhibition of translational elongation factor eEF2. Differentiation of $T_{CD4, FoxP3}$ from $CD4_+ CD25_{neg}$ T cells was accomplished by gating in the stimulated and unstimulated experiments.

Figures 16A, 16B, 16D:
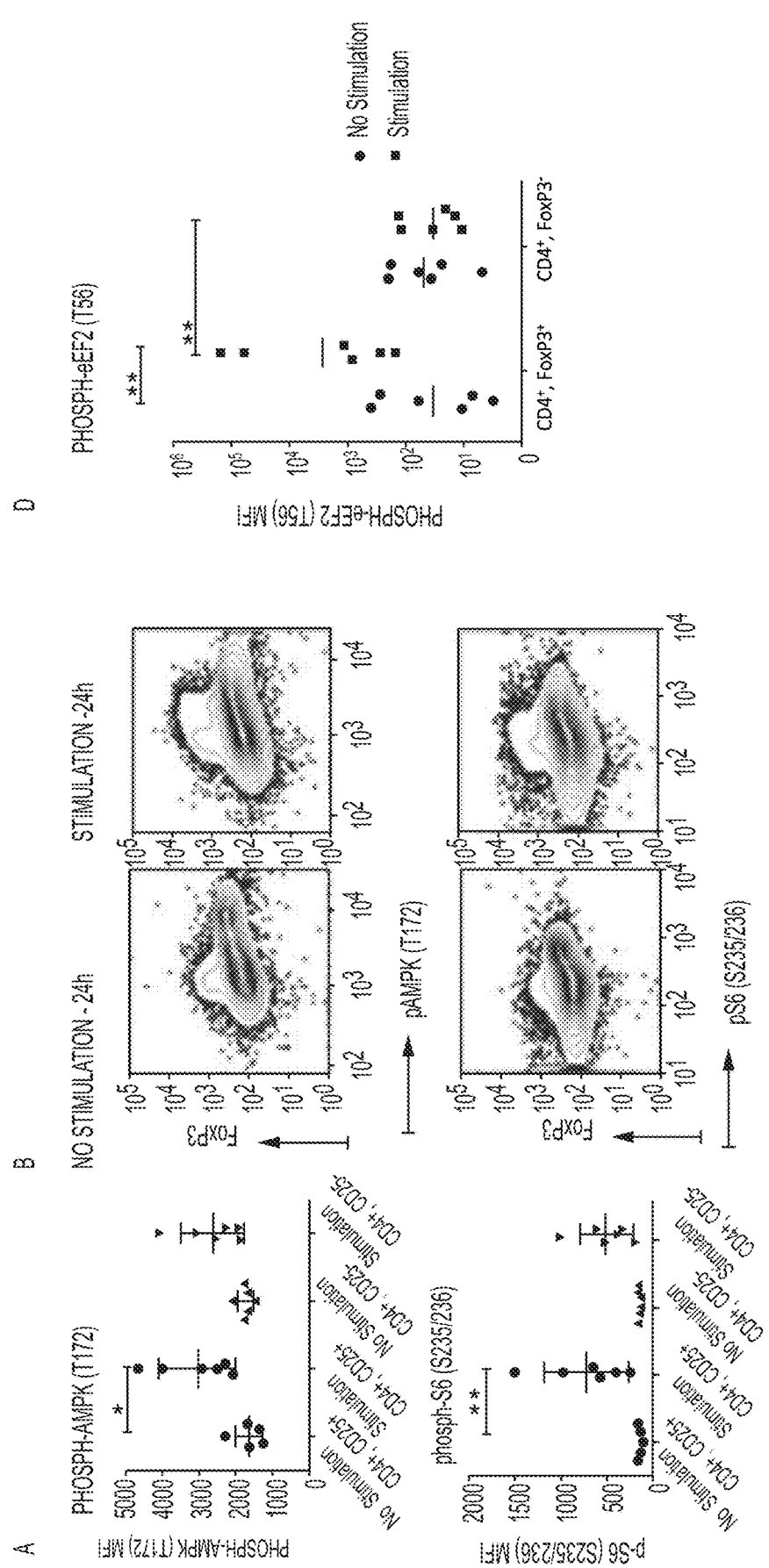

FIG. 16A depicts the mean fluorescence intensity (MFI) of AMPK activated by phosphorylation at T172 after stimulation in the top panel while the lower panel of FIG. 16A depicts the MFI of activated S6 by phosphorylation at sites S235/S236.

FIG. 16B depicts a flow plot depicting the changes in phosphorylation for $T_{CD4, FoxP3}$ and $CD4^+ CD25_{neg}$ T cells in the upper panel for AMPK and in the lower panel for S6 with respect to FoxP3 expression in gated $CD4^+$ cells.

Figures 16C, 16E:
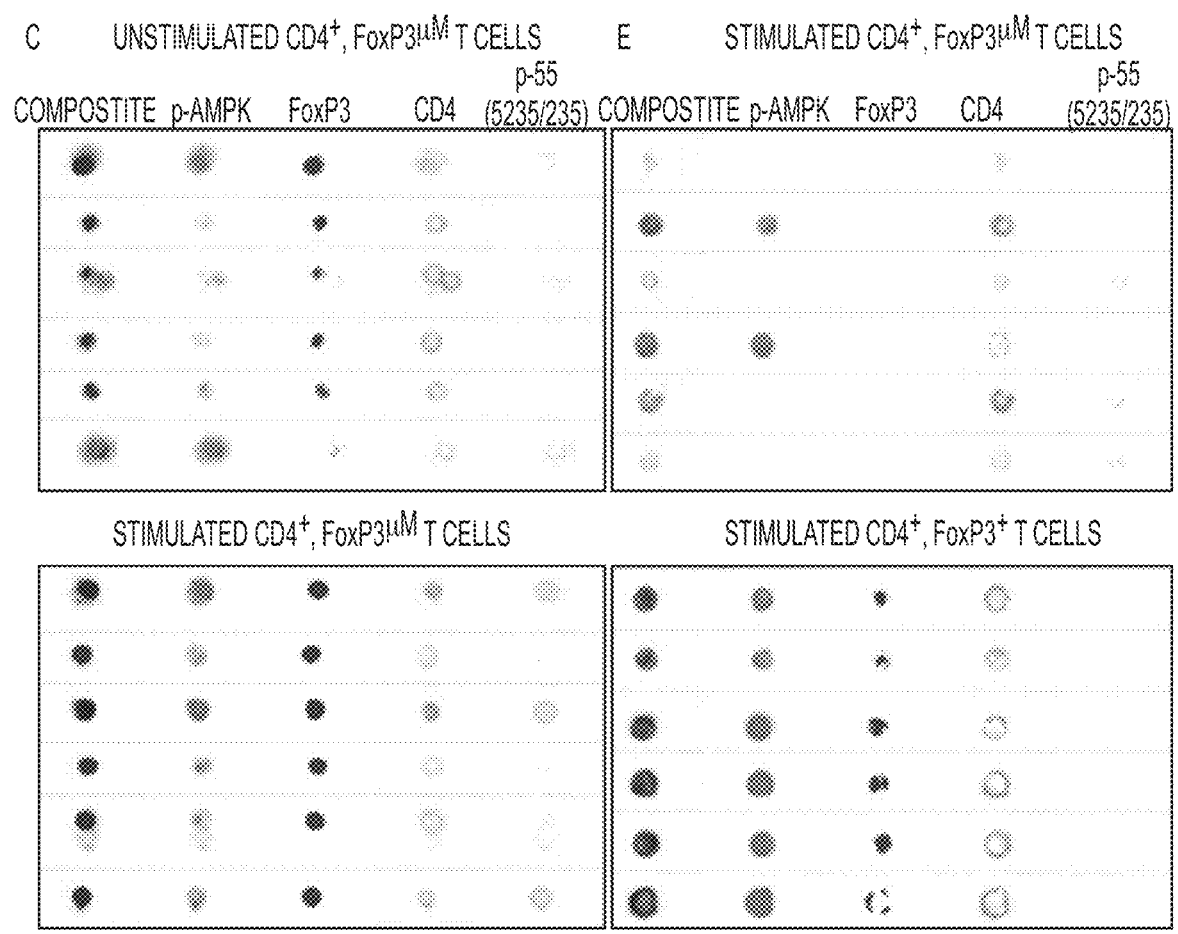

FIG. 16C is an image cytometry gallery depicting fluorescent and morphologic changes in $T_{CD4, FoxP3}$ following stimulation.

FIG. 16D shows an image cytometer was used to analyze p-eEF2 T56 MFI and depicts an increase in activation of $T_{CD4, FoxP3}$.

FIG. 16E shows the difference from $CD4^+ FoxP3^{neg}$ T cells in image cytometry gallery.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. Unless defined otherwise, all technical and scientific terms used herein have the same meaning as commonly understood by one of ordinary skill in the art. The following terms are provided below.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

By "animal" is meant any member of the animal kingdom including vertebrates (e.g., frogs, salamanders, chickens, or horses) and invertebrates (e.g., worms, etc.). "Animal" is also meant to include "mammals." Preferred mammals include livestock animals (e.g., ungulates, such as cattle, buffalo, horses, sheep, pigs and goats), as well as rodents (e.g., mice, hamsters, rats and guinea pigs), canines, felines, primates, lupine, camelid, cervidae, rodent, avian and ichthyes.

As used herein, the term "antibody" is meant to refer to complete, intact antibodies, and Fab fragments and F(ab)$_2$ fragments thereof. Complete, intact antibodies include monoclonal antibodies such as murine monoclonal antibodies (mAb), chimeric antibodies and humanized antibodies. The production of antibodies and the protein structures of complete, intact antibodies, Fab fragments and F(ab)$_2$ fragments and the organization of the genetic sequences that encode such molecules are well known and are described, for example, in Harlow et al., ANTIBODIES: A LABORATORY MANUAL, Cold Spring Harbor Laboratory, Cold Spring Harbor, N.Y. (1988) which is incorporated herein by reference.

As used herein, the term "autologous" is meant to refer to any material derived from the same individual to which it is later to be re-introduced into the individual.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

By "epitope" is meant a region on an antigen molecule to which an antibody or an immunogenic fragment thereof binds specifically. The epitope can be a three dimensional epitope formed from residues on different regions of a protein antigen molecule, which, in a native state, are closely apposed due to protein folding. "Epitope" as used herein can also mean an epitope created by a peptide or hapten portion of matriptase and not a three dimensional epitope.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fusion protein" or "fusion polypeptide" is a polypeptide comprised of at least two polypeptides and optionally a linking sequence, and that are operatively linked into one continuous protein. The two polypeptides linked in a fusion protein are typically derived from two independent sources (i.e., not from the same parental polypeptide), and therefore a fusion protein comprises two linked polypeptides not normally found linked in nature. Typically, the two polypeptides can be operably attached directly by a peptide bond, or may be connected by a linking group, such as a spacer domain. An example of a fusion polypeptide is a polypeptide that functions as a receptor for an antigen, wherein an antigen binding polypeptide forming an extracellular domain is fused to a different polypeptide, forming a "chimeric antigen receptor".

By "knock-in" of a target gene means an alteration in a host cell genome that results in altered expression (e.g., increased, including ectopic) of the target gene, e.g., by introduction of an additional copy of the target gene or by operatively inserting a regulatory sequence that provides for enhanced expression of an endogenous copy of the target gene. See U.S. Pat. No. 6,175,057.

By "knock-out" of a gene means an alteration in the sequence of the gene that results in a decrease of function of the target gene, preferably such that target gene expression is undetectable or insignificant. See U.S. Pat. No. 6,175,057.

By "modulating" or "regulating" is meant the ability of an agent to alter from the wild type level observed in the individual organism the activity of a particular gene, protein, factor, or other molecule.

By "mutant" with respect to a polypeptide or portion thereof (such as a functional domain of a polypeptide) is meant a polypeptide that differs in amino acid sequence from the corresponding wild type polypeptide amino acid sequence by deletion, substitution or insertion of at least one amino acid. A "deletion" in an amino acid sequence or polypeptide is defined as a change in amino acid sequence in which one or more amino acid residues are absent as compared to the wild-type protein. As used herein an "insertion" or "addition" in an amino acid sequence or polypeptide is a change in an amino acid sequence that has resulted in the addition of one or more amino acid residues as compared to the wild-type protein.

As used herein "substitution" in an amino acid sequence or polypeptide results from the replacement of one or more amino acids by different amino acids, respectively, as compared to the wild-type protein.

"Isolated" means altered or removed from the natural state. For example, a nucleic acid or a peptide naturally present in a living animal is not "isolated," but the same nucleic acid or peptide partially or completely separated from the coexisting materials of its natural state is "isolated" An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses Vectors derived from lentiviruses offer the means to achieve significant levels of gene transfer in vivo.

The term "linker", also referred to as a "spacer" or "spacer domain" as used herein, refers to a an amino acid or sequence of amino acids that that is optionally located between two amino acid sequences in a fusion protein.

The term "operably linked" (and also the term "under transcriptional control") refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to a human being.

The term "polynucleotide" is a chain of nucleotides, also known as a "nucleic acid". As used herein polynucleotides include, but are not limited to, all nucleic acid sequences which are obtained by any means available in the art, and include both naturally occurring and synthetic nucleic acids.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" means a DNA sequence recognized by the synthetic machinery of the cell, or introduced synthetic machinery, required to initiate the specific transcription of a polynucleotide sequence.

By "somatic cell" is meant any cell of a multicellular organism, preferably an animal, that does not become a gamete.

The term "therapeutically effective amount" shall mean that amount of drug or pharmaceutical agent that will elicit the biological or medical response of a tissue, system or animal that is being sought by a researcher or clinician.

The term "transfected" or "transformed" or "transduced" means to a process by which exogenous nucleic acid is transferred or introduced into the host cell. A "transfected" or "transformed" or "transduced" cell is one which has been transfected, transformed or transduced with exogenous nucleic acid. The transduced cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Examples of vectors include but are not limited to, linear polynucleotides, polynucleotides associated with ionic or amphiphilic compounds, plasmids, and viruses. Thus, the term "vector" includes an autonomously replicating plasmid or a virus. The term is also construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

DESCRIPTION OF ILLUSTRATIVE EMBODIMENTS

In one aspect, an isolated transgenic mammalian T cell comprising or expressing a transgene and one or more of $DHFR^{FS}$ and $TYMS^{SS}$ is provided. In some embodiments, the isolated transgenic mammalian T cell comprises or expresses a transgene, $DHFR^{FS}$ and $TYMS^{SS}$. Briefly, T cells can be obtained from peripheral blood mononuclear cells, bone marrow, lymph node tissue, cord blood, thymus tissue, tissue from a site of infection, ascites, pleural effusion, spleen tissue, and tumors. T cell lines available in the art may be used. Preferably, T cells are obtained from a unit of blood collected from a subject using any number of techniques known to those skilled in the art. Isolation of T cells may proceed according to procedures known in the art, as described in US2013/0287748 A1. The harvested T cells are then expanded using methods well-known in the art, such as described in US2013/0287748 A1.

According to one embodiment, T-cells are harvested and processed for lentiviral transduction as follows. Patient peripheral blood mononuclear cells are purified and washed in phosphate-buffered saline (PBS) with 1% human serum albumin. Lymphocytes are enriched using magnetic bead depletion of monocytes, according to known methods. Lymphocytes are cultured according to Good Manufacturing Practice regulations as previously described by Levine et al., (1998), *J Hematother* 7:437-448. The cells are expanded ex vivo for 14 days in a serum-free hematopoietic cell medium, e.g., X-VIVO 15 of Lonza Group Ltd. (a chemically defined, serum-free hematopoietic cell medium) supplemented with 10% Normal Human Antibody Serum, and then processed for reinfusion on day 14 of culturing. The magnetic beads are removed using a magnetic cell separation system. The cells are harvested, washed and resuspended in a Plasmalyte A containing 1% human serum albumin before being transduced with lentiviral vectors.

As demonstrated herein, T cells are genetically modified to express anti-thymidylate resistance (AThyR) transgenes, and other transgenes. AThyRs are shown to rescue T cells from anti-thymidylate (AThy) drug toxicity, such as AThy toxicity mediated by 5-FU and anti-folates targeting DHFR and TYMS. Also, as demonstrated herein DHFR muteins such as DHFR$^{FS}$ permits methotrexate (MTX)-inducible increase in transgene expression that is thymidine dependent, and TYMS muteins such as TYMS$^{SS}$ permit MTX-inducible decrease in transgene expression that is dihydrofolate dependent. As further demonstrated herein, AThyRs can be used to positively select for transgenes of interest without the use of immunogenic genes or magnetic selection.

The use of AThyR transgenes DHFR$^{FS}$ and TYMS$^{SS}$ alone or in combination, engineered into T cells expressing a transgene of interest, provides a unique capacity to select for transgene expression within the bulk population, can modulate the expression of cis as well as trans transgenes of interest, and promote survival in toxic concentrations of AThys. Thus, T cells expressing transgenes of interest, such as T cells expressing tumor-targeting chimeric antigen receptors (CARs), further engineered to express AThyRs such as DHFR$^{FS}$ and/or TYMS$^{SS}$, find utility in treating cancers such as lung, colon, breast, and pancreas that are in need of new therapeutic options.

As demonstrated herein, combining AThyRs DHFR$^{FS}$ and TYMS$^{SS}$ in T cells leads to significant survival advantages for such cells treated with toxic concentrations of AThys: MTX, Pem, or 5-FU. These AThy drugs are regularly used to treat lung and colon cancer among other common cancers. The findings described herein indicate that AThyRs T cells can survive toxic AThy concentrations. Combining the immunomodulatory effects of chemotherapy like 5-FU with T cells resistant to the cytotoxic effects of 5-FU could substantially improve the anti-cancer response of the patient beyond that of either therapeutic used alone.

As described herein, for the purpose of selecting transgenes of interest for T cell expression, AThyRs were compared to one of the earliest drug resistance transgenes—NeoR. As described herein, it was found that DHFR$^{FS}$ is superior to NeoR in promoting survival, selection, and drug-dependent increases of expression of a representative transgene (eGFP). Notably, DHFR$^{FS}$ and TYMS$^{SS}$ have lower immunogenicity as human proteins, and MTX can be used both in vitro and in vivo[1] to improve transgene selection, whereas G418 cannot. The findings described herein demonstrate that DHFR$^{FS}$ can select for cells expressing transgenes such as the suicide gene iC9. Thus, DHFR$^{FS}$ and [DHFR$^{FS}$ & TYMS$^{SS}$] are attractive alternatives to alternative to magnetic beads for selecting T cells expressing one or more transgenes of interest. In fact, the potential to select for AThyR+ T cells in vivo using MTX indicates that transgene selection could be performed within the patient rather than ex vivo.

In another aspect is provided a method for inhibiting AThy toxicity in a mammalian T cell comprising expressing an AThyR transgene in said mammalian T cell. In some embodiments, the AThyR transgene is DHFR$^{FS}$. In some embodiments, the AThyR transgene is TYMS$^{SS}$.

In another aspect is provided a method for selecting a T cell expressing a transgene of interest. The method comprises applying a thymidine synthesis inhibitor to a plurality of T cells that comprises a T cell expressing the transgene of interest and DHFR$^{FS}$ and selecting for one or more T cells surviving after seven or more days of application of the thymidine synthesis inhibitor, wherein the one or more T cells expresses the vector comprising the transgene of interest and DHFR$^{FS}$. The thymidine synthesis inhibitor may be selected from the group consisting of methotrexate (MTX), 5-FU, Raltitrexed and Pemetrexed.

In some embodiments, a DNA sequence, including DNA sequences from genes described herein, is inserted into the vector. Vectors derived from retroviruses are preferred, as they provide long-term gene transfer since and allow stable integration of a transgene and its propagation in daughter cells. Expression of nucleic acids encoding the AThyRs described herein may be achieved using well-known molecular biology techniques by operably linking a nucleic acid encoding the AThyRs to a promoter, and incorporating the construct into a suitable expression vector. The vectors can be suitable for replication and integration eukaryotes. Typical cloning vectors contain transcription and translation terminators, initiation sequences, and promoters useful for regulation of the expression of the desired nucleic acid sequence.

In some embodiments, one or more DNA constructs encode the transgene and one or more DNA constructs encoding one or more AThyRs, DHFR$^{FS}$ and TYMS$^{SS}$. In other embodiments, the transgene and the one or more AThyRs, DHFR$^{FS}$ and TYMS$^{SS}$ are operably linked. A chimeric construct encoding the various nucleotide sequences encoding one or more transgenes and one or more AThyRs, DHFR$^{FS}$ and TYMS$^{SS}$ may be prepared by well-known molecular biology techniques, from naturally derived or synthetically prepared nucleic acids encoding the components. The chimeric constructs may be prepared using natural sequences. The natural genes may be isolated and manipulated as appropriate so as to allow for the proper joining of the various domains. Thus one may prepare the truncated portion of the sequence by employing polymerase chain reaction (PCR) using appropriate primers which result in deletion of the undesired portions of the gene. Alternatively, one may use primer repair where the sequence of interest may be cloned in an appropriate host. In either case, primers may be employed which result in termini which allow for annealing of the sequences to result in the desired open reading frame encoding the CAR protein. Thus, the sequences may be selected to provide for restriction sites which are blunt-ended or have complementary overlaps. Preferably, the constructs are prepared by overlapping PCR.

As demonstrated herein, anti-thymidylates or thymidine synthesis inhibitors, exemplified by MTX, can be used to regulate transgene expression either to higher or lower expression levels for a transgene expressed cis to DHFR$^{FS}$ or TYMS$^{SS}$. MTX-inducible positive or negative modulation of cis-transgenes is believed clinically useful in situations where MTX is used to modulate the spatial and temporal expression of dangerous but necessary transgenes in T cells, such as transgenes expressing certain chimeric antigen receptors (CAR) or cytokines. The correlated expression of DHFR$^{FS}$ with trans expressed TYMS$^{SS}$ is also useful in expressing proteins such as TCR α and β that need to be expressed at nearly equivalent amounts and where the use of 2A mediated cleavage sites may adversely affect protein structure and function.

Yet another aspect is a method for selectively propagating peripheral blood mononuclear cells (PBMC) resistant to MTX and 5-FU. The method comprises transfecting peripheral PBMC with a vector comprising an AThyR gene, treating the transfected PBMC with a thymidine synthesis inhibitor and selecting for PBMC that express the AThyR gene. In some embodiments of this aspect, the method further comprises propagating a T cell population from the transfected PBMC. In some embodiments, the thymidine synthesis inhibitor may be selected from the group consisting of methotrexate (MTX), 5-FU, Raltitrexed and Pemetrexed. In some embodiments, the thymidine synthesis inhibitor is MTX. In some embodiments, the AThyR gene is TYMS$^{SS}$. In some embodiments, the AThyR gene is DHFR$^{FS}$.

Another aspect is an isolated transgenic mammalian T cell comprising a nucleic acid sequence comprising a transgene of interest and a nucleotide sequence encoding DHFR$^{FS}$ or TYMS$^{SS}$. In some embodiments, the isolated transgenic mammalian T cell comprises a nucleic acid comprising a transgene of interest and a nucleotide sequence encoding DHFR$^{FS}$, wherein the transgene of interest and the nucleotide sequence encoding DHFR$^{FS}$ are operably linked. In some embodiments, the isolated transgenic mammalian T cell comprises a nucleic acid comprising a transgene of interest and a nucleotide sequence encoding TYMS$^{SS}$, wherein the transgene of interest and the nucleotide sequence encoding TYMS$^{SS}$ are operably linked.

In another aspect is provided an isolated transgenic mammalian T cell expressing a transgene and DHFR$^{FS}$, wherein the T cell comprises (1) a polynucleotide comprising sequence that encodes the transgene and (2) a polynucleotide comprising sequence that encodes the DHFR$^{FS}$.

In certain aspects, a sequence encoding DHFR$^{FS}$ encodes a polypeptide at least about 80%, 85%, 90%, 91%, 92%, 93%, 94%, 95%, 96%, 97%, 98%, 99% or 100% to SEQ ID NO: 12. In some embodiments, a sequence encoding DHFR$^{FS}$ encodes a polypeptide having no more than 1, 2, 3, 4, 5, 6, 7, 8, 9 or 10 amino acid deletions, insertions or substitutions relative to SEQ ID NO: 12.

In another aspect is provided an isolated transgenic mammalian T cell expressing a transgene and TYMS$^{SS}$, wherein said T cell comprises (1) a polynucleotide comprising sequence that encodes the transgene and (2) a polynucleotide comprising sequence that encodes the TYMS$^{SS}$.

In certain aspects, a sequence encoding TYMS$^{SS}$ encodes a polypeptide at least about 80%, 85%, 90%, 91%, 92%, 93%, 94%, 95%, 96%, 97%, 98%, 99% or 100% to SEQ ID NO: 11. In some embodiments, a sequence encoding TYMS$^{SS}$ encodes a polypeptide having no more than 1, 2, 3, 4, 5, 6, 7, 8, 9 or 10 amino acid deletions, insertions or substitutions relative to SEQ ID NO: 11.

In a further aspect, a composition is provided comprising a plurality of human cells (e.g., T-cells), wherein the cells comprise a sequence encoding TYMS$^{SS}$ and a first transgene, said cells having been treated with MTX (e.g., in culture or in a living organism), thereby changing expression of the transgene. In certain embodiments, the transgene encodes a CAR, TCR, polypeptide hormone (e.g., an endocrinological hormone, such as glucagon), cytokine, a transcription factor or chemokine. In still further aspects, a transgene of the embodiments encodes a cell surface polypeptide, such as an integrin, cytokine receptor, chemokine receptor or a receptor of a hormone (e.g., a neurological or endocrine hormone).

In still a further aspect, a composition is provided comprising a plurality of human cells (e.g., T-cells), wherein the cells comprise a sequence encoding DHFR$^{SS}$ and a first transgene, said cells having been treated with MTX (e.g., in culture or in a living organism), thereby changing expression of the transgene. In certain embodiments, the transgene encodes a CAR, TCR, polypeptide hormone (e.g., an endocrinological hormone, such as glucagon), cytokine, transcription factor or chemokine. In still further aspects, a transgene of the embodiments encodes a cell surface polypeptide, such as an integrin, cytokine receptor, chemokine receptor or a receptor of a hormone (e.g., a neurological or endocrine hormone).

In a further aspect, there is provided a composition comprising a first plurality of T cells isolated from a mammal and treated with a thymidine synthesis inhibitor, wherein the first plurality of T cells is enriched for regulatory T cells as compared to a second plurality of T cells isolated from a mammal that is depleted by a thymidine synthesis inhibitor during stimulation with a(n) antibody(ies) compromising any singular or combination use of anti-CD2, anti-CD3, anti-CD27, anti-CD28, anti-41BB, anti-OX40, phytohemagluttinin (PHA), ionomycin or peptide pulsed antigen presenting cells (whether synthetic or biologic and of any cell origin whether human or otherwise if utilized to stimulate T cells in such a way that the T cells begin to replicate).

In yet another aspect is provided a method of treating a patient with a cancer comprising to administering to a patient a therapeutically effective amount of a T cell of an isolated T cell of any of the above embodiments. While few cell therapies and no cell-based gene therapies are currently approved by the FDA, any of the transgenic techniques reported herein can be used to prepare a composition to administer to a patient with cancer. Further, CAR-mediated ex vivo expansion can be used to generate a therapeutically effective amount of a T cell of an isolated T cell of any of the above embodiments.

The processed T cells of the invention can be generated by introducing a lentiviral vector containing any of the above-described nucleic acid constructs into T cells, such as autologous T cells of a patient to be treated for cancer or an IgE-mediated allergic disease. A composition comprising autologous T cells is collected from a patient in need of such treatment. The cells are engineered into the processed T cells ex vivo, activated and expanded using the methods described herein and known in the art, and then infused back into the patient. The processed T cells replicate in vivo resulting in persistent immunity against cancer cells or other cells expressing mIgE.

Any of the above isolated T cells may be processed, with the processed T cells then transduced with lentiviral vectors as described above to generate processed T cells for administration. Transduction is carried out according to known protocols.

The processed T cells are administered to a subject in need of treatment for an IgE-mediated allergic disease. The processed T cells are able to replicate in vivo, providing long-term persistence that can lead to sustained allergic disease control. The processed T cells may be administered either alone, or as a pharmaceutical composition in combination with one or more pharmaceutically acceptable carriers, diluents or excipients and/or with other components, such as cytokines or other cell populations. Such compositions may comprise buffers such as neutral buffered saline, phosphate buffered saline and the like: carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions are preferably formulated for intravenous administration. Preferably, the T cells comprise autologous T cells that are removed from the subject and engineered ex vivo to express the CAR and administered to the subject.

The processed T cells or pharmaceutical composition thereof may be administered by a route that results in the effective delivery of an effective amount of cells to the patient for pharmacological effect. Administration is typically parenteral. Intravenous administration is the preferred route, using infusion techniques that are commonly known in immunotherapy (see, e.g., Rosenberg et al., New Eng. J. of Med. 319:1676, 1988). The quantity of CAR$^+$ T cells and frequency of administration are determined by such factors as the condition of the patient, and the type and severity of the patient's disease, although appropriate dosages may be determined by clinical trials. An "effective amount" is determined by a physician with consideration of individual differences in age, weight, disease state, and disease severity of the patient. Generally, the amount of CAR$^+$ T given in a single dosage will range from about $10^6$ to $10^9$ cells/kg body weight, including all integer values within those ranges. The CAR$^+$ T may be administered multiple times at these dosages. The optimal dosage and treatment regime for a particular patient can readily be determined by one skilled in the art of medicine by monitoring the patient for signs of disease and adjusting the treatment accordingly.

In yet another aspect is provided a method for selecting for a T cell expressing a transgene of interest, as shown in any of the FIGS. or as described in the description.

In yet another aspect is provided a T cell, as shown in any of the FIGS. or as described in the description.

In another aspect is a method for selectively propagating primary human T cells resistant to one or more of MTX, 5-FU, Raltitrexed and Pemetrexed, as shown in any of the FIGS. or as described in the description.

Another aspect is a method of enriching for regulatory T cells in a population of T cells isolated from a mammal by contacting said population with a thymidine synthesis inhibitor selected from the group consisting of MTX, 5-FU, Raltitrexed and Pemetrexed, or a combination thereof, to selectively deplete effector T cells in the population. In some embodiments, the population of T cells isolated from a mammal is contacted with both MTX and 5-FU. In some embodiments, the T cells express one or more of DHFR$^{FS}$ and TYMS$^{SS}$. In some embodiments, the T cells express both DHFR$^{FS}$ and TYMS$^{SS}$.

Specific inhibition of 5-aminoimidazole-4-carboxamide riboside (AICAR) synthesis has been shown herein to be neither toxic to T cells nor selective for $T_{CD4, FoxP3}$. FoxP3 expression in $T_{CD4, FoxP3}$ has now been found to be enhanced by the specific action of AICARtf inhibition, suggesting some action of AMPK may improve $T_{reg}$ phenotype. Without wishing to be bound by theory, isolated $T_{reg}$ studies described herein show that the action of MTX is twofold: 1) Selection of $T_{reg}$ is dependent on the depletion of $T_{eff}$ as removal of $T_{eff}$ prevents the selective increase of $T_{reg}$ following MTX treatment. 2) The action of MTX does enhance $T_{reg}$ functional activity in some regard as latency associated peptide (LAP) expression and suppression of Teff proliferation were increased above untreated $T_{reg}$. The activation of AMPK in the absence of folate depletion by MTX was achieved in the transgenic T cell experiments and increased the percent of T cells with a functional $T_{reg}$ phenotype. Thus, MTX depletes $T_{eff}$ and promotes an immunosuppressive $T_{reg}$ phenotype.

Another aspect is a method for depleting regulatory T cells in a population of T cells isolated from a mammal by culturing said population in the presence of one or more aminoglycosidases to selectively deplete the regulatory T cells in said culture. In some embodiments, the T cells express one or more of DHFR$^{FS}$ and TYMS$^{SS}$. In some embodiments, the T cells express both DHFR$^{FS}$ and TYMS$^{SS}$. In some embodiments, Treg can be rescued from G418-mediated depletion when Neomycin resistance gene, which prevents G418 toxicity, was present. The aminoglycoside depletion may be specifically limited to regulatory T cells. While aminoglycosides have been in use for several decades the capacity of this drug to deplete Treg has not been described. Without wishing to be bound by theory, the most likely explanation is that the drug is used at much lower doses in vivo than those used to deplete Treg in vitro, and is often discontinued for toxicity to multiple tissues.

In some embodiments, aminoglycosides can be administered to a patient with a tumor in order to enhance anti-tumor activity. Aminoglycosides can be administered by pretreatment in a therapy, for example.

Another aspect is a method for selecting for a regulatory T cell isolated from a mammal. The method comprises treating a plurality of T cells expressing one or more of DHFR$^{FS}$ and TYMS$^{SS}$ with a thymidine synthesis inhibitor and selecting a regulatory T cell that expresses a marker for a regulatory T cell. In some embodiments, the T cells express DHFR$^{FS}$. In some embodiments, the selecting step comprises cell isolating with magnetic bead sorting using one or more of an anti-CD4 antibody, an anti-CD25 antibody, an anti-CD3 antibody, an anti-CD8 antibody, an anti-CD25 antibody, an anti-CD39 antibody, an anti-CD45 antibody, an anti-CD152 antibody, an anti-KI-67 antibody, and an anti-FoxP3 antibody. In some embodiments, the thymidine synthesis inhibitor is selected from the group consisting of methotrexate (MTX), 5-FU, Raltitrexed or Pemetrexed. In some embodiments, the method further comprises treating the regulatory T cell with one or more of folate, leucovarin and FU.

As further demonstrated herein, AThyRs protect AThyRs T cells from anti-folate toxicity from MTX or Pem. Results described herein establish that MTX is more toxic to T cells than Pem and that MTX susceptibility to <1 µM MTX could be completely abrogated by the codon optimization of DHFR$^{FS}$ or by the addition of TYMS$^{SS}$ to DHFR$^{FS}$ in T cells. Concentrations of up to 1 µM MTX are achieved during the treatment of rheumatoid arthritis. Higher doses of MTX are achieved in cancer chemotherapy (>1 mM MTX) with the use of leucovorin. Leucovorin rescues thymidine synthesis through the same pathway as combination DHFR$^{FS}$ and TYMS$^{SS}$. Thus, it is believed that [DHFR$^{FS}$ & TYMS$^{SS}$]$^+$ T cells will likely resist cytotoxicity induced by the range of MTX experienced for both immune suppression and cancer treatment.

In another aspect is provided a composition comprising a first plurality of T cells isolated from a mammal and a thymidine synthesis inhibitor. The first plurality of T cells is enriched for regulatory T cells as compared to a second plurality of T cells isolated from a mammal that does not comprise a thymidine synthesis inhibitor.

In various embodiments of any of the above aspects and embodiments, T cells (T lymphocytes) as used herein may comprise or consist of any naturally occurring or artificially (e.g., synthetically, genetically, recombinantly) engineered immune cells expressing naturally occurring or made to express or present on the cell surface artificially (e.g., synthetically, genetically, recombinantly) engineered T cell receptors or portions thereof, including, for example but not limited to, chimeric, humanized, heterologous, xenogenic, allogenic, and autologous T cell receptors.

In various embodiments of any of the above aspects and embodiments, "T cells" as used herein include all forms of T cells, for example, but not limited to T helper cells ($T_H$ cells), cytotoxic T cells ($T_c$ cells or CTLs), memory T cells ($T_{CM}$ cells), effector T cells ($T_{EM}$ cells), regulatory T cells (Treg cells, also known as suppressor T cells), natural killer T cells (NKT cells), mucosal associated invariant T cells, alpha-beta T cells (Tαβ cells), and gamma-delta T cells (Tγδ cells).

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and together with the detailed description, serve to explain the principles of the present invention.

All cited patents and publications referred to in this application are herein incorporated by reference in their entirety.

Example 1

Materials and Methods
Cells and Culture Conditions:

Cells: Peripheral blood mononuclear cells (PBMC) derived from healthy donors at the Gulf Coast Regional Blood Bank or MDACC Blood Bank, both in Houston, Tex., was subjected to density gradient centrifugation using Ficoll-Paque Plus (GE Healthcare Biosciences, Piscataway Township, N.J.; Cat No. 17-1440-02). PBMC were washed once in CliniMACS Plus PBS/EDTA buffer (Miltenyi Biotec, Gladbach, Germany, Cat. No. 130-070-525) and twice in Dulbecco's PBS (D-PBS) (Sigma-Aldrich, St. Louis, Mo., Cat. No. D8537) before resting in complete media (CM) made of RPMI 1640 (Thermo Scientific Hyclone, Bridgewater, N.J.; Cat. No. SH30096.01), 10% heat-inactivated fetal bovine serum (FBS-Thermo Scientific Hyclone, Cat. No. SH30070.03), and 2 mM GlutaMAX supplement (Life Technologies, Grand Island, N.Y.; Cat. No. 35050061). Alternatively, PBMC were frozen using a prepared mixture of 50% heat-inactivated FBS, 40% RPMI 1640, and 10% DMSO (Sigma-Aldrich, PA: Cat. No. D2650)—freeze media (FM) at 4×107 cells/mL. The use of rested or frozen PBMC is outlined in each experiment, below. The Jurkat cell line, a human T cell acute lymphoblastic leukemia (American Type Culture Collection, Manassas, Va., Cat. No. TIB-152) was used and maintained in CM. The identity of this cell line was assured by short tandem repeat DNA fingerprinting performed by MDACC Cancer Center Support Grant Characterized Cell Line Core. Activating and propagating cells (AaPC) were used to stimulate T cells. The AaPC cell line K562 clone.4, expressing CD86, CD137, CD64, along with membrane bound IL-15, was modified to present OKT3 antibody for the polyclonal stimulation of T cells, as previously described (Singh et al., *Journal of immunotherapy* 2014, 37(4):204-213). For the propagation of chimeric antigen receptor (CAR)+ T cells, the AaPC CARL+ K562 (Rushworth et al., *Journal of immunotherapy* 2014, 37(4):204-213) was utilized.

All AaPC were rapidly thawed in a 37° C. water bath and washed twice before stimulation of T cells (Singh et al., supra). Jurkat and AaPC were tested for the presence of mycoplasma before use Cell counting was accomplished in a mixture of 0.1% Trypan Blue (Sigma-Aldrich, T8154) with the Cellometer K2 Image Cyotmeter (Nexcelom, Lawrence, Mass.).

Chemical and Biological Agents:

Stimulation via CD3 and CD28 was achieved by the addition of 30 ng/mL OKT3 antibody (eBioscience, San Diego, Calif., Cat. No. 16-0037-85), 100 ng/mL anti-CD28 antibody (EMD Millipore, Temecula, Calif., Cat. No. CBL517). T cell stimulation included recombinant human IL-2 (Proleukin, Prometheus Labs, San Diego, Calif.). When indicated, the following drugs were used: 5-FU, MTX, pemetrexed, raltitrexed, G418, and AP20187. Further information regarding each drug is given in Table 1.

DNA Expression Plasmids:

DNA plasmids for testing anti-thymidylate resistance (AThyR) transgenes were generated using the previously described DNA plasmid G4CAR as a backbone (Rushworth et al., supra). Commercially synthesized FLAG-DHFR$^{FS}$, codon optimized (CoOp) DHFR$^{FS}$, FLAG-TYMS$^{SS}$, and CoOp TYMS$^{SS}$ DNA (Life Technologies, Gene Art), and neomycin resistance gene (NeoR) DNA product were cleaved by NheI and ApaI. Reporter genes mCherry with N-terminus SV40 nuclear localization sequence (RFP), inducible suicide gene CoOp iC9 (both produced by GeneArt), and enhanced green fluorescent protein.

TABLE 1

| Chemical Agents | | |
|---|---|---|
| Agent | Manufacturer | ID No. |
| 5-fluorouracil | APP Pharmaceuticals, Schaumburg, IL | NDC 63323-117-10 |
| Methotrexate | Hospira, Lake Forest IL | NDC 61703-350-38 |
| Pemetrexed | Lilly, Indianapolis, IN | NDC 0002-7610-01 |
| Raltitrexed | Abcam Biochemicals, Cambridge, MA | AB142974 |
| G418 | Invivogen, San Diego, CA | Ant-gn-1 |
| AP20187 | Clontech, Mountain View, CA | 635060 |

Figure 1A:
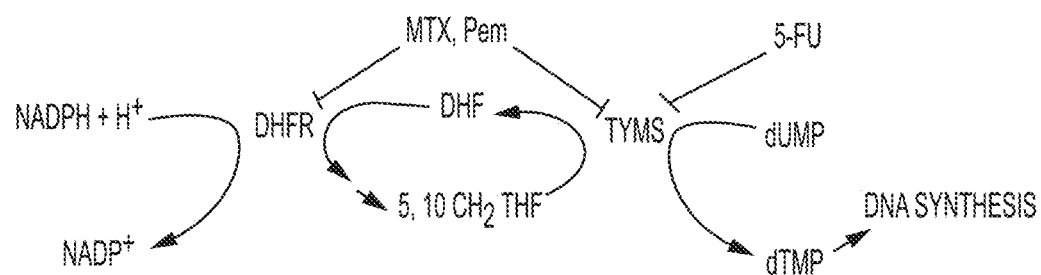
FIG. 1A depicts a pathway showing the role of synthesis of thymidine in DNA replication and cell survival.
Figure 1B:
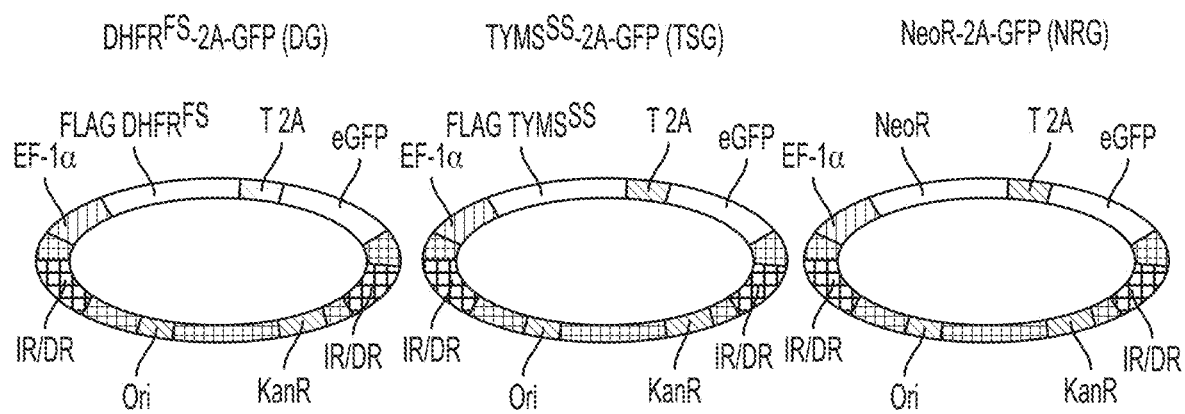
FIG. 1B depicts the design of putative AThyR transgenes resistant to AThy toxicity in order to confer resistance to T cells that might be used in a combination therapeutic with AThy chemotherapy. AThyRs were co-expressed with a fluorescent protein to indicate that surviving cells contained the transgene. These transgene utilized the Sleeping Beauty transposon/transposase system to induce stable transgene expression in Jurkat. Human muteins $DHFR^{FS}$—resistant to MTX (left), human mutein $TYMS^{SS}$—resistant to 5-FU (center), and the gold-standard Neomycin resistance gene (NeoR) drug resistance gene-resistance to G418 (right) were used in this study. Codon optimized (CoOp) versions of $DHFR^{FS}$ & $TYMS^{SS}$ replaced native codon $DHFR^{FS}$ & $TYMS^{SS}$ to test whether known post-transcriptional regulatory mechanisms were affecting AThyR selection or survival.

(eGFP) DNA were digested by ApaI and KpnI. The G4CAR backbone was restriction enzyme digested by NheI and KpnI. The G4CAR backbone was ligated with NheI and ApaI digested fragments and ApaI and KpnI digested fragments in a three component ligation. Enzyme digestion locations of NheI, KpnI, and ApaI are shown in FIG. 1B. The drug resistant component (DHFR$^{FS}$, TYMS$^{SS}$, or NeoR) was permutated with the transgenes (RFP, CoOp iC9, and GFP) to make the following DNA plasmids: FLAG-DHFR$^{FS}$-2A-eGFP pSBSO (DG), FLAG-CoOp DHFR$^{FS}$-2A-eGFP pSBSO (CoOp DG); FLAG-TYMS$^{SS}$-2A-GFP pSBSO (TSG); FLAG-CoOp TYMS$^{SS}$-2A-GFP pSBSO (CoOp TSG); FLAG-TYMS$^{SS}$-2A-RFP pSBSO (TSR); NeoR-2A-GFP pSBSO (NRG); and FLAG-DHFR$^{FS}$-2A-iC9 pSBSO (DFSiC9). The construct FLAG-TYMS$^{SS}$-2A-IL-12p35-2A-IL-12p40 pSBSO (TS$^{SS}$IL-12) was synthesized from codon optimized (GeneArt, Life Technologies) IL-12 p35 and IL-12 p40 transgenes and digested within the 2A regions to ligate IL-12 p35 and IL-12 p40 with a TYMS$^{SS}$ fragment also digested within the 2A region. TS$^{SS}$G backbone digestion points 5′ to the start site of TYMS$^{SS}$ and 3' to the IL-12p40 stop site ligated the three components into the TS$^{SS}$G backbone in a four part ligation. A construct is also provided, which encodes Myc-DHFR$^{FS}$-2A (the polypeptide sequence corresponding to Myc-DHFR$^{FS}$-2A is provided as SEQ ID NO: 10). The polypeptide sequence for TYMS$^{SS}$ is provided as SEQ ID NO: 11. The polypeptide sequence for DHFR$^{FS}$ is provided as SEQ ID NO: 12. Codon optimization of DHFR$^{FS}$ and TYMS$^{SS}$ DNA was performed to avoid the mRNA transcript from being bound by DHFR and TYMS proteins, respectively. Known RNA binding motifs of DHFR and TYMS mRNA are recognized by DHFR (Tai et al., *The Biochemical journal* 2004, 378 (Pt 3): 999-1006) and TYMS (Lin et al., *Nucleic acids research* 2000, 28(6):1381-1389), respectively. Codons of DHFR$^{FS}$ and TYMS$^{SS}$ were altered as much as possible while maintaining the amino acid sequence of each protein in order to avoid protein binding of the mRNA transcript. Previously described CD19-specific chimeric antigen receptor (CAR) (Rushworth et al., supra) was utilized without modification.

Myc-ffLuc-NeoR pSBSO (NRF) was constructed using the backbone of CD19-2A-Neo pSBSO (Rushworth et al., supra) isolated after restriction digestion with NheI and SpeI. NheI and SpeI digested Myc-firefly Luciferase (ffLuc) insert was ligated to CD19-2A-Neo backbone followed by digestion of the ligation product with SpeI and EcoRV. SpeI and EcoRV digested NeoR fragments were then ligated to the digested backbone to yield NRF. All constructs contain Sleeping Beauty (SB) indirect/direct repeat (IR/DR) sites to induce genomic integration in the presence of SB transposase. Each transgene is promoted using elongation factor 1 alpha (EF1-α) promoter. Cartoon representations of constructs can be seen in FIG. 1B and FIG. 8A. Select DNA and protein sequences can be found in Table 2.

TABLE 2

Synthetic DNA/protein sequences

| | |
|---|---|
| FLAG-dmDHFR | Atggactacaaggacgacgacgacaaggattacaagga tgatgatgataaggactataaagacgacgatgataagg acgtcgttggttcgctaaactgcatcgtcgctgtgtcc cagaacatgggcatcggcaagaacggggacttccctg gccaccgctcaggaatgaatccagatattccagagaa tgaccacaacctcttcagtagaaggtaaacagaatctg gtgattatgggtaagaagacctggttctccattcctga gaagaatcgaccttttaaagggtagaattaatttagttc tcagcagagaactcaaggaacctccacaaggagctcat tttctttccagaagtctagatgatgccttaaaacttac tgaacaaccagaattagcaaataaagtagacatggtct ggatagttggtggcagcctgtttataaggaagccatga atcacccaggccatcttaaactatttgtgcaaggatc atgcaagactttgaaagtgacacgttttttccagaaat tgatttggagaaatataaacttctgccagaatacccag gtgttctctctgatgtccaggaggagaaaggcattaag tacaaatttgaagtatatgagaagaatgat (SEQ ID NO: 1) |
| FLAG-CoOp dmDHFR | Atggactacaaggacgacgacgacaaggattacaagga tgatgatgataaggactataaggacgatgatgacaaag acgtcgtgggcagcctgaactgcatcgtggccgtgtcc cagaacatgggcatcggcaagaacggcgacttccctg gccccctctgcggaacgagagccggtacttccagcgga tgaccaccaccagcagcgtggaaggcaagcagaacctc gtgatcatgggcaagaaaacctggttcagcatccccga gaagaaccggcccctgaagggccggatcaacctggtgc tgagcagagagctgaaagagccccctcagggcgcccac ttcctgagcagatctctgacgacgccctgaagctgac cgagcagccaggctggccaacaaggtggacatggtgt ggatcgtgggcggcagctccgtgtacaaagaagccatg aaccaccctggccacctgaaactgttcgttaccgtat aatgcaggatttcgagagcgatacctctcccccgaga tcgacctggaaaagtacaagctgcttcccgagtaccc | |

TABLE 2-continued

Synthetic DNA/protein sequences

| | |
|---|---|
| | ggcgtgctgtccgatgtgcaggaagagaagggcatcaa gtacaagttcgaggtgtacgagaagaatgac (SEQ ID NO: 2) |
| FLAG-dmTYMS | Atgtatccgtacgacgtaccagactacgcatatccgta cgacgtaccagactacgcagacgtccctgtggccggct cggagctgccgcgccggccttgcccccgccgcacag gagcgggacgccgagccgcgtccgccgcacggggagct gcagtacctggggcagatccaacacatcctccgctgcg gcgtcaggaaggacgaccgctcgagcaccggcaccctg tcggtattcggcatgcaggcgcgctacagcctgagaga tgaattccctctgctgacaaccaaacgtgtgttctgga agggtgttttggaggagttgctgtgttatcaaggga tccacaaatgctaaagagctgtcttccaagggagtgaa aatctgggatgccaatggatcccgagacttttttggaca gcctgggattctccaccagagaagaaggggacttggga ccagtttatggcttccagtggaggcattttggggcaga atacagagatatggaatcagattattcaggacagggag ttgaccaactgcaaagagtgattgacaccatcaaaacc aaccctgacgacagaagaatcatcatgtgcgcttgaa tccaagagatcttcctctgatggcgctgcctccatgcc atgccctctgccagttctatgtggtgaacagtgagctg tcctgccagctgtaccagagatcgggagacatgggcct cggtgtgcctttcaacatcgccagctacgccctgctca cgtacatgattgcgcacatcacgggcctgaagccaggt gactttatacacactttggggagtgcacatatttacct gaatcacatcgagccactgaaaattcagcttcagcgag aacccagaccttcccaaagctcaggattcttcgaaaa gttgagaaaattgatgacttcaaagctgaagactttca gattgaagggtacaatccgcatccaactattaaaatgg aaatggctgtt (SEQ ID NO: 3) |
| FLAG-CoOp-dmTYMS | Atggactacaaggacgacgacgacaaggattacaagga tgatgatgataaggactataaggacgatgatgacaaag acgtccccgtggccggcagcgagctgcctagaaggcct ctgcctcctgccgctcaggaaaggacgccgaacctag acctcctcacggcgagctgcagtacctgggccagatcc agcacatcctgagatgcggcgtgcggaaggacgacaga agcagcacaggcaccctgagcgtgttcggaatgcaggc cagatacagcctgcgggacgagttccctctgctgacca ccaagcgggtgttctggaagggcgtgctggaagaactg ctgtggttcatcaagggcagcaccaacgccaaagagct gagcagcaagggcgtgaagatctgggacgccaacggca gcagagacttcctggacagcctgggcttcagcaccagga gaggaaggcgatctgggtcccgtgtacgggtttcaatg gcggcacttcggcgccgagtatcgggacatggagagcg actacagcggccagggcgtggaccagctgcagagagtg atcgacaccatcaagaccaacccccgacgaccggcggat catcatgtgcgcctggaacccccagagatctgccctga tggccctgcctccatgtcacgccctgtgccagttctac gtcgtgaactccgagctgagctgccagctgtaccagcg gagcggcgatatgggactgggcgtgcctttcaatatcg ccagctacgccctgctgacatgatcgcccacatc accggcctgaagcccggcgactttatccacaccctggg cgacgcccatatctacctgaaccacatcgagccctga agattcagctgcagcgcgagcccagacccttcccaaag ctgcggatcctgcggaaagtgaaaagatcgacgactt caaggccgaggacttccagatcgagggctacaaccccc accccacaatcaagatggaaatggccgtg (SEQ ID NO: 4) |
| eGFP forward | 5' cccgggcccggcgccatgccacctcctcgcctcct cttc 3' (SEQ ID NO: 5) |
| eGFP reverse | 5' ggtacccttgtacagctcgtccatgccgagagtga tcccgcggcggtcac 3' (SEQ ID NO: 6) |
| NeoR forward | 5' gctagcacatgtgccaccatgattgaacaagatgg attgcacgcaggttctccggccgcttgg 3' (SEQ ID NO: 7) |
| NeoR reverse | 5' aagcttccgcggccctctccgctaccgaagaactc gtcaagaaggcgatagaaggcgatgcgctgcgaat c 3' (SEQ ID NO: 8) |
| NLS | MAPKKKRKVGIHRGVP (SEQ ID NO: 9) |

Genetic Modification and Propagation of Cells:

The Amaxa Nucleofector® II (Lonza, Allendale, N.J.) was used to electroporate both Jurkat and human PBMC. Electroporation of Jurkat cells utilized a modified buffer (Chicaybam et al., *Proceedings of the National Academy of Sciences of the United States of America* 2002, 99(6):3400-3405) containing 5 mM KCl, 15 mM $MgCl_2$, 120 mM $Na_2HPO_4/NaH_2PO_4$, pH 7.2, and 50 mM DMSO, where $10^6$ Jurkat cells per cuvette were electroporated using program T-14 before immediate transfer to CM. The addition of drug occurred 48 hours after electroporation and cell culture remained undisturbed until sampling for gene expression on days 10-12 post electroporation. Human PBMC electroporation followed a previously described protocol (Rushworth et al., supra). Briefly, 1 to $2 \times 10^7$ thawed PBMC per cuvette were electroporated in Amaxa T cell Nucleofector solution (Lonza Biosciences; Cat No. VPA-1002) using program U14. On the following day, PBMC were stimulated in fresh CM with AaPC at a ratio of 1:1 including 50 IU/mL IL-2, unless otherwise noted. The cellular co-culture concentration of $10^6$ cells/mL was maintained at each stimulation, and PBMC derived T cells were re-stimulated every 7 days using the same concentrations. IL-2 was added when media was changed between stimulations. Drug treatment initiated 48 hours after co-culture began and continued until day 14. Drug was only added with fresh CM.

Western Blot:

$10^6$ T cells were centrifuged from culture, supernatant aspirated, and the pellet rapidly frozen in liquid nitrogen. Whole-cell extracts were harvested using 50 mM Tris, 150 mM NaCl, 1 mM EDTA, 1% NP-40, 0.5% deoxycholate, 1 mM phenylmethylsulfonyl fluoride, 150 mM p-nitrophenyl phosphate and 0.3 µM Aprotinin, pH 7.4. Proteins were separated by SDS-PAGE in reducing conditions and analyzed using specific primary antibodies indicated in Table 3. Detection was performed using an enhanced chemiluminescence detection system.

Flow Cytometry:

Cultured cells were resuspended, and washed once in FACS staining solution (Rushworth et al., supra). If transgene expression alone was sought, the specimen was then analyzed on a flow cytometer. The BD LSRFortessa (BD Biosciences) was used to analyze RFP expression; otherwise, BD FACSCalibur (BD Biosciences) was used. Surface antibody staining was performed in FACS staining solution with fluorochrome-conjugated antibodies at 4° C. for at least 30 minutes. Antibody targets, concentrations, and manufacturers are listed in Table 4. Analysis of flow cytometry data utilized FlowJo v 10.0.5 (Tree Star Inc., Ashland, Oreg.).

Luciferase Assay:

Cultured T cells were tested for the persistence of ffLuc transgene by the cleavage of D-luciferin (Perkin Elmer, Waltham, Mass., Cat. No. 122796). Resuspended cells were plated and washed once in D-PBS before testing in a D-PBS solution of D-luciferin at 0.14 mg/mL. After incubation at 37° C. for 10 min, the plate was analyzed on a TopCount NXT Luminescence Counter (Perkin Elmer).

TABLE 3

Western Blot Antibodies

| Antibody | Manufacturer | Cat. No. | Dilution |
|---|---|---|---|
| Actin | Sigma | A2228 | 1:10000 |
| Hsp-70 | Santa Cruz Biotechnology, Dallas, TX | SC-24 | 1:5000 |

TABLE 3-continued

Western Blot Antibodies

| Antibody | Manufacturer | Cat. No. | Dilution |
|---|---|---|---|
| DHFR | Santa Cruz Biotechnology | SC-377091 | 1:1000 |
| TYMS | Millipore | MAB4130 | 1:1000 |
| Myc Tag | CST | 2276S | 1:1000 |
| DYKDDDDK Tag | Pierce | MA1-91876 | 1:1000 |

TABLE 4

Flow Cytometry Antibodies

| Antibody | Manufacturer | Cat. No. | Dilution |
|---|---|---|---|
| CD3-APC | BD Pharmingen | 340661 | 1:33 |
| CD3-PerCP-Cy5.5 | BD Pharmingen | 340949 | 1:33 |
| CD4 FITC | BD Pharmingen | 340133 | 1:33 |
| CD4-PE | BD Pharmingen | 347327 | 1:33 |
| CD4-PerCP-Cy5.5 | BD Pharmingen | 341645 | 1:33 |
| CD8-APC | BD Pharmingen | 340359 | 1:33 |
| Annexin V-PE | BD Pharmingen | 556422 | 1:20 |
| 7-AAD | BD Pharmingen | 559925 | 1:20 |
| Propidium Iodide | BD Pharmingen | 556463 | |
| Human Fc-PE | Invitrogen | H10104 | 1:40 |
| Myc-AF488 | MBL | M047-A48 | 1:33 |
| FLAG-AF647 | Cell Signaling | 3916S | 1:33 |

Chromium Release Assay:

Antigen specific cytotoxicity was assessed by CRA. This assay was previously described (Rushworth et al., supra). Briefly, antigen positive CD19+ EL-4 were compared to antigen negative $CD19^{neg}$ EL-4 after each cell line was loaded with $^{51}Cr$ for 3 hours and subsequently incubated with CD19-specific CAR+ T cells at a 1 target:5 effector cell ratio for 6 hours. Release of $^{51}Cr$ from cell lysis was assessed by the TopCount NXT scintillation counter.

Statistical Analysis:

Statistical analysis and graphical representation of data was achieved using Prism v6.0 (Graph Pad Software Inc., La Jolla, Ca). Experiments of more than one variable were analyzed by multivariate analysis: Two-Way ANOVA was used when appropriate with Sidak's multiple comparison test, One-Way ANOVA was used when appropriate with Tukey's or Dunnett's multiple comparison tests as applicable, non-Gaussian distributions were assessed by the Kruskall-Wallis test followed by Dunn's multiple comparison test. Single variable tests (experimental vs. control) were made using the Mann-Whitney test. Statistical significance was designated as $\alpha < 0.05$.

Results

A. Testing AThyR Transgene Selection in Jurkats $DHFR^{FS}$ were used to determine whether T cells can be genetically-modified to resist toxic doses of AThys used in the initial treatment of malignancy. $DHFR^{FS+}$ T cells resistant to MTX are described by Jonnalagadda et al., *PloS one* 2013, 8(6):e65519, and Jonnalagadda et al., *Gene therapy* 2013, 20(8):853-860. 5-FU resistant TYMS muteins previously identified within a bacterial culture system (Landis et al., *Cancer research* 2001, 61(2):666-672) were tested in human cells (data not shown) and $TYMS^{SS}$ was chosen for further study.

Figure 1C:
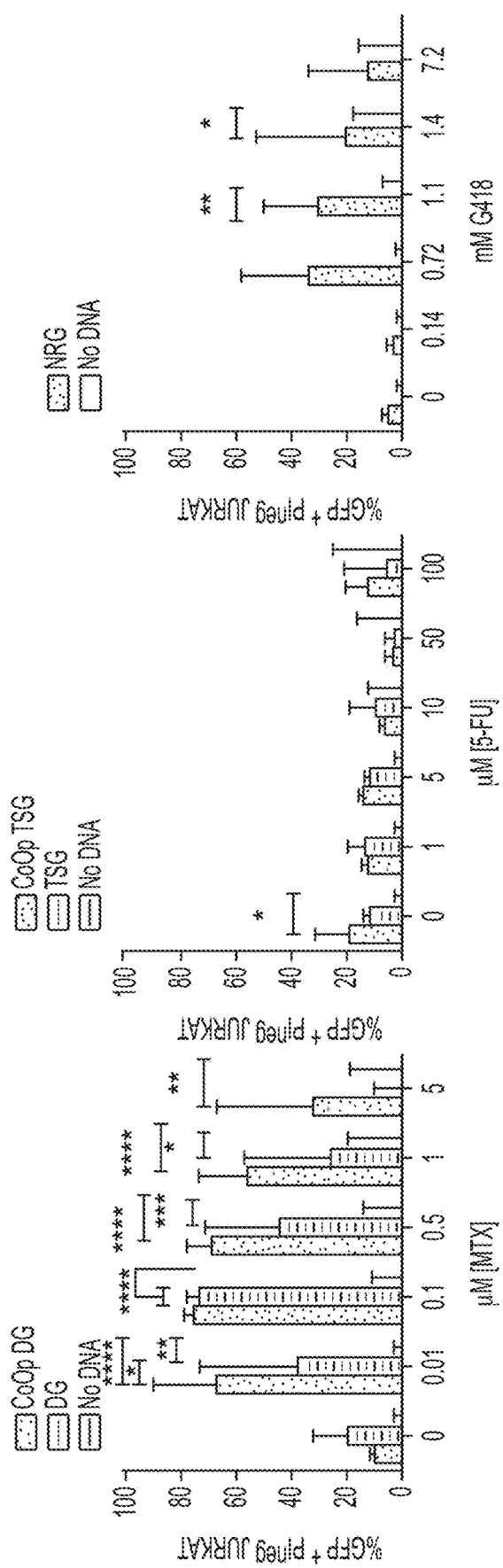
FIG. 1C depicts three different panels showing the percentage of eGFP+ viable Jurkat T cells following treatment with MTX (left panel), 5-FU (center panel) and G418 (right panel) at varying concentrations. The left panel relates to DHFR$^{FS}$-2A-GFP (DG), CoOp DG, and no DNA, that were electroporated into Jurkat and subjected to MTX after 2 days. The center panel relates to TYMS$^{SS}$-2A-GFP (TSG), CoOp TSG, and No DNA electroporated Jurkat that were treated on day 2 with 5-FU. The right panel relates to NeoR-GFP and No DNA electroporated Jurkat that were treated on day 2 with G418. For each experiment in C the percentage of eGFP$^+$ viable Jurkat is given after testing on day 8-10 after the addition of drug.

To test the enhanced survival of each AThyR, constructs individually expressing $DHFR^{FS}$, $TYMS^{SS}$, and NeoR were ligated into the same backbone containing Sleeping Beauty (SB) transposable elements upstream of eGFP (FIG. 1B), eGFP was used to track the predominance of surviving genetically-modified T cells. Jurkat cells were co-electroporated with each construct and SB11 transposase (Singh et al., *Cancer Research* 2008, 68(8):2961-2971), which mediated genomic integration of each construct. Cytotoxic drugs were added two days after electroporation. Jurkat were assessed for eGFP expression in viable cells by propidium iodide (PI) exclusion on day 10-12 (FIG. 1C). Increased percentage expression of eGFP was sought as a measure for transgene selection in the presence of drug. Overall survival and mean fluorescence intensity (MFI) of eGFP are also given in FIG. 2AI and AII, respectively. Overall, the data demonstrate that DHFR$^{FS}$ has much better selection than the traditional drug-resistance transgene NeoR. The data also demonstrate that TYMS$^{SS}$ has no independent capacity to enhance Jurkat survival.

Figures 2A, 2B, 2C:
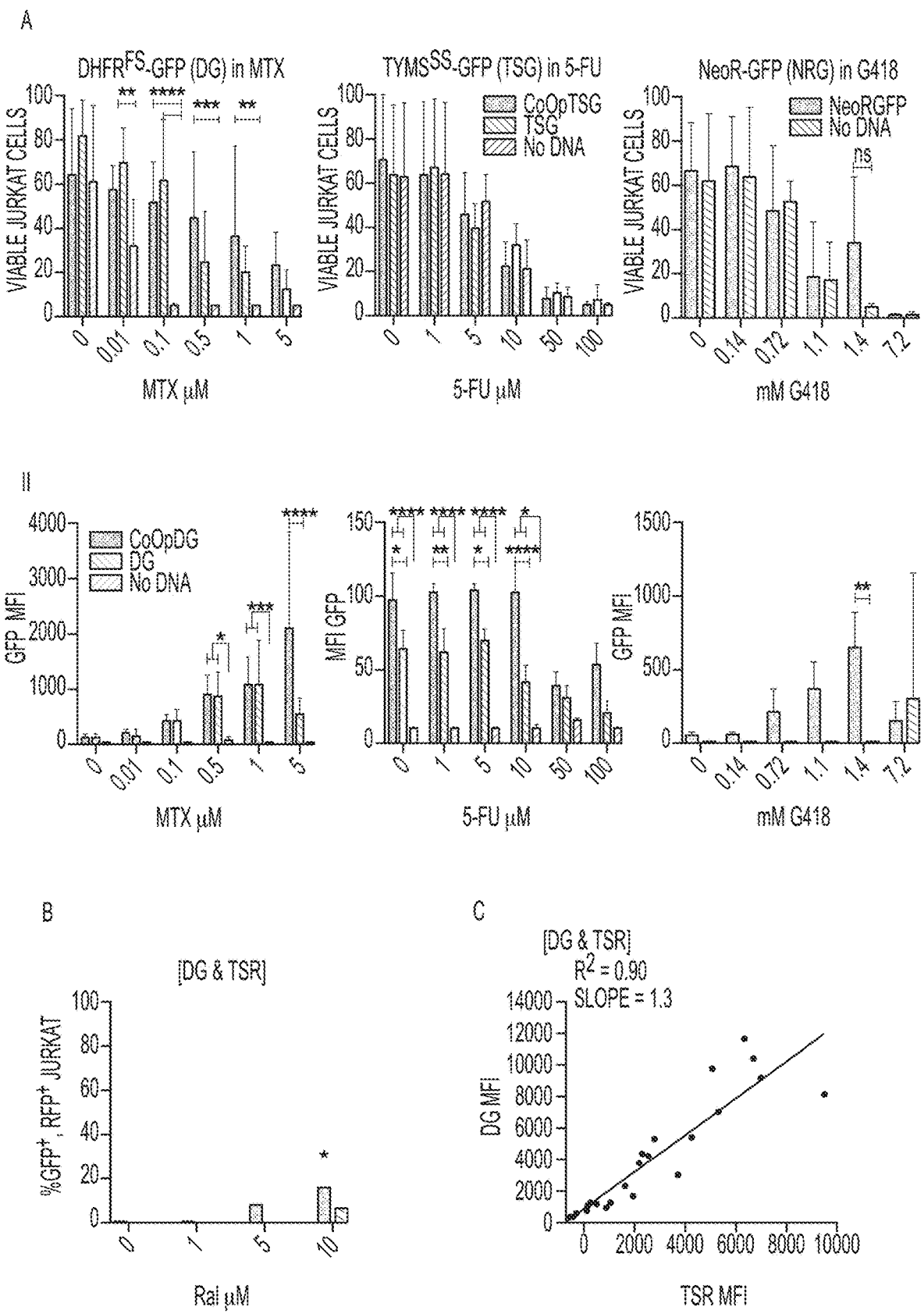

More specifically, it was found that DHFR$^{FS}$ confers resistance to MTX at concentrations range of 0.01-0.5 μM, and codon optimization of DHFR$^{FS}$ enhanced the drug resistance range of CoOp DHFR$^{FS}$ to 0.01-1 μM (FIG. 1C). Codon optimization removed potential endogenous DHFR binding to the DHFR$^{FS}$ mRNA as well as possible micro RNA binding domains. Notably, gating on eGFP$^+$ cells demonstrated that DHFR$^{FS}$ constructs lead to a MTX dependent increase in eGFP MFI. Hence, eGFP expression within a single cell increased based on the addition of MTX. This finding occurred independent of mRNA regulation until 5 μM MTX where endogenous codon DHFR$^{FS}$ expression significantly decreased compared to CoOp DHFR$^{FS}$ ($p<0.0001$) (FIG. 2A-II). Drug inducible transgene expression is a rare phenomenon. This phenomenon, although rare, is not novel. While the capacity of DHFR to increase cis-expressed eGFP in an MTX dependent manner was previously described for native DHFR, the phenomenon was attributed to MTX binding DHFR, DHFR releasing DHFR mRNA, and free DHFR mRNA leading to increased translation of DHFR protein (Meyer et al., *Proceedings of the National Academy of Sciences of the United States of America* 2002, 99(6):3400-3405). Here it is noted that the phenomenon also occurs with MTX resistant DHFR$^{FS}$, and with DHFR$^{FS}$ occurs independent of mRNA regulation from 0.01-1 μM MTX. Hence, without wishing to be bound by any theory, it is believed that the regulation of DHFR expression occurs partially through a heretofore unknown mRNA independent mechanism.

There was no drug selective advantage for TYMS$^{SS}$ expressing Jurkat when tested with 5-FU (FIG. 1C). Native codon TYMS$^{SS}$ had no expression advantage over No DNA Jurkat at any concentration of 5-FU. Further analysis of eGFP$^+$ cells for eGFP MFI revealed that TYMS$^{SS}$ expressed at a lower eGFP MFI compared to CoOp TYMS$^{SS}$ (FIG. 2A). It is concluded that lower expression of TYMS$^{FS}$ due to mRNA based suppression contributed to the lack of TYMS$^{SS}$ survival advantage. When mRNA regulatory mechanisms are ablated by codon optimization, TYMS$^{SS}$ has a significant expression advantage over mock electroporated Jurkat, and a weak survival advantage in 5 μM 5-FU. Without wishing to be bound by any theory, the lack of significantly enhanced survival is likely due to an alternative mechanism of 5-FU contributing to toxicity.

NeoR was used to select for enhanced survival of Jurkat in the presence of G418. This was intended to serve as a standard to gauge the utility of DHFR$^{FS}$ and TYMS$^{SS}$. Electroporation of NeoR into Jurkat improved survival in the presence of G418 at 0.72-1.1 mM G418 (FIG. 1C). The survival advantage of NeoR over No DNA was not significant due to variability (FIG. 2A), but a G418 dependent increase in GFP MFI was noted. The GFP MFI significantly increased above No DNA Jurkat at 1.4 mM G418 (FIG. 2A-II). These results reinforce that DHFR$^{FS}$ and NeoR are capable of providing dose-dependent transgene selection advantage in surviving Jurkat. However, only DHFR$^{FS}$ conferred reliable survival advantages to Jurkat in this experiment (FIG. 2A-II).

Figure 1D:
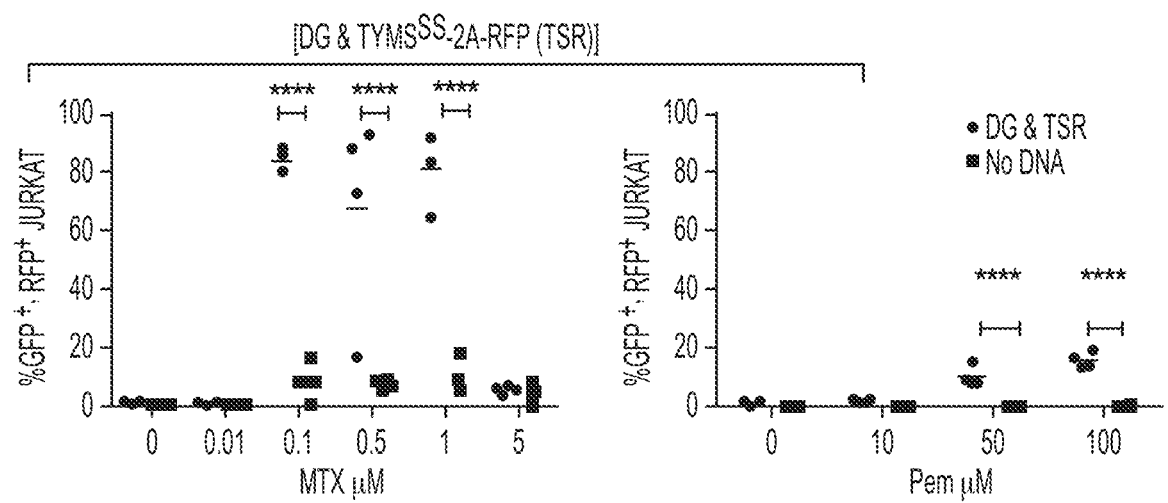
FIG. 1D depicts the effect of MTX and Pemetrexid on the survival of cells that expressed native DHFR and TYMS ("No DNA") or expressed. DG and TYMS$^{SS}$-2A-RFP (TSR) were co-electroporated into Jurkat to determine whether combination DHFR$^{FS}$ & TYMS$^{SS}$ confer enhanced survival to MTX (left) or Pemetrexid (right).
Figure 1E:
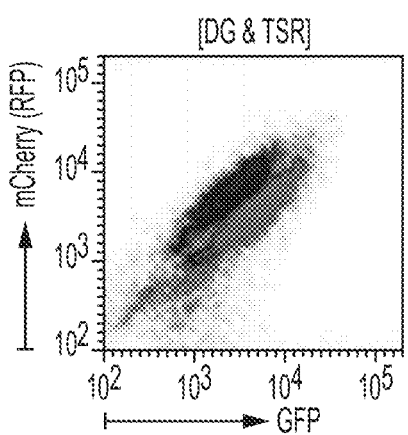
FIG. 1E depicts that following 2 weeks of selection in 1 μM MTX, [DHFR$^{FS}$ & TYMS$^{SS}$]$^+$ Jurkat displayed a uniform and repeatable pattern of correlated expression. Shown here, four separate [DHFR$^{FS}$ & TYMS$^{SS}$]$^+$ Jurkat experiments are overlaid in different shades. Experiments were independently repeated at least twice with 4-6 replicates. *=p<0.05, =p<0.01, *=p<0.001, ****=p<0.0001; Dihydrofolate (DHF); DHF reductase (DHFR), deoxyuridine monophosphate (dUMP), deoxythymidine monophosphate (dTMP); 5, 10-methylenetetrahydrofolate (5,10 CH$_2$THF); nicotinamide adenine dinucleotide phosphate (NADP).

The next experiment combined DHFR$^{FS}$ and TYMS$^{SS}$ by co-electroporating each plasmid into Jurkat. The capacity of the combined transgenes to resist commonly used anti-folate AThys: MTX, Pem, and Raltitrexed (Ral), were tested. As before, drug was added on day 2 and cells were tested on day 10-12. There was clear selection for [DHFR$^{FS}$ & TYMS$^{SS}$] expressing Jurkat in 0.1-1 μM MTX when compared to similarly treated No DNA or untreated [DHFR$^{FS}$ & TYMS$^{SS}$]$^+$ Jurkat (FIG. 1D). It should be noted that endogenous codon DHFR$^{FS}$ was used in these experiments and the resistance to MTX was enhanced from 0.5 (FIG. 1C) to 1 μM MTX (FIG. 1D) by the addition of TYMS$^{SS}$ with no other changes to the experimental conditions. Selection was also noted for 50-100 μM Pem (FIG. 1D). Moderate selection was also noted with 10 μM Ral when compared to untreated [DHFR$^{FS}$ & TYMS$^{SS}$]$^+$ Jurkat (FIG. 2B). Ral primarily targets TYMS, whereas MTX and Pem target both DHFR and TYMS (Walling, *Investigational new drugs* 2006, 24(1):37-77), hence the improved selection for MTX and Pem over Ral in [DHFR$^{FS}$ & TYMS$^{SS}$]$^+$ Jurkat. After 2 weeks within 1 μM MTX, surviving [DHFR$^{FS}$ & TYMS$^{SS}$]$^+$ Jurkat were refreshed in untreated media and grown for 3-5 weeks. Subsequently, the stability of transgene expression of [DHFR$^{FS}$ & TYMS$^{SS}$]+ Jurkat was tested by flow cytometry with the co-expression of eGFP representing DHFR$^{FS}$ expression and RFP representing TYMS$^{SS}$ expression as seen in FIG. 1E. Each color represents a separate experiment and is overlaid to represent the trend that DHFR$^{FS}$ and TYMS$^{SS}$ co-express in a correlated fashion. In fact, analysis of GFP MFI representing DHFR$^{FS}$ expression and RFP MFIs representing TYMS$^{SS}$ expression over multiple anti-folate drugs, at multiple concentrations demonstrated that DHFR$^{FS}$ & TYMS$^{SS}$ co-express with a strong Pearson's correlation ($R^2=0.9$) (FIG. 2C). Without wishing to be bound by theory, this finding suggests that expression of DHFR$^{FS}$ is somehow regulated by the expression of TYMS$^{SS}$, or vice versa.

B. Selective Propagation of Primary Human T Cells Resistant to MTX and/or 5-FU.

Figure 3A:
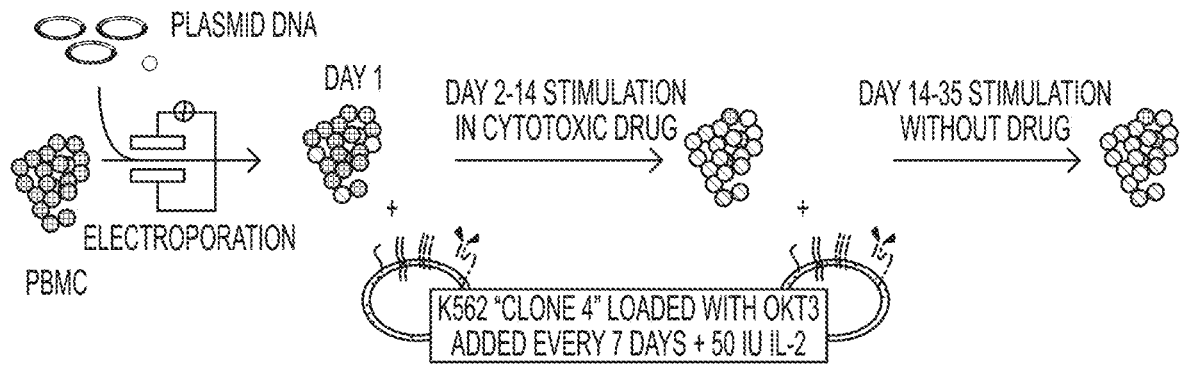
FIG. 3A depicts a propagation schematic showing initial AaPC stimulation. Two days after AaPC stimulation, the co-cultures received 0.1 μM MTX, 5 μM 5-FU, or 1.4 mM G418 until day 14. The co-cultures were re-stimulated with AaPC at a 1:1 ratio and given 50 IU/mL IL-2 every 7 days from day 1 to 35. Phenotypic changes in transgene expression were tracked during drug administration for the first 14 days and for the 21 days after drug administration had ended
Figure 3B:
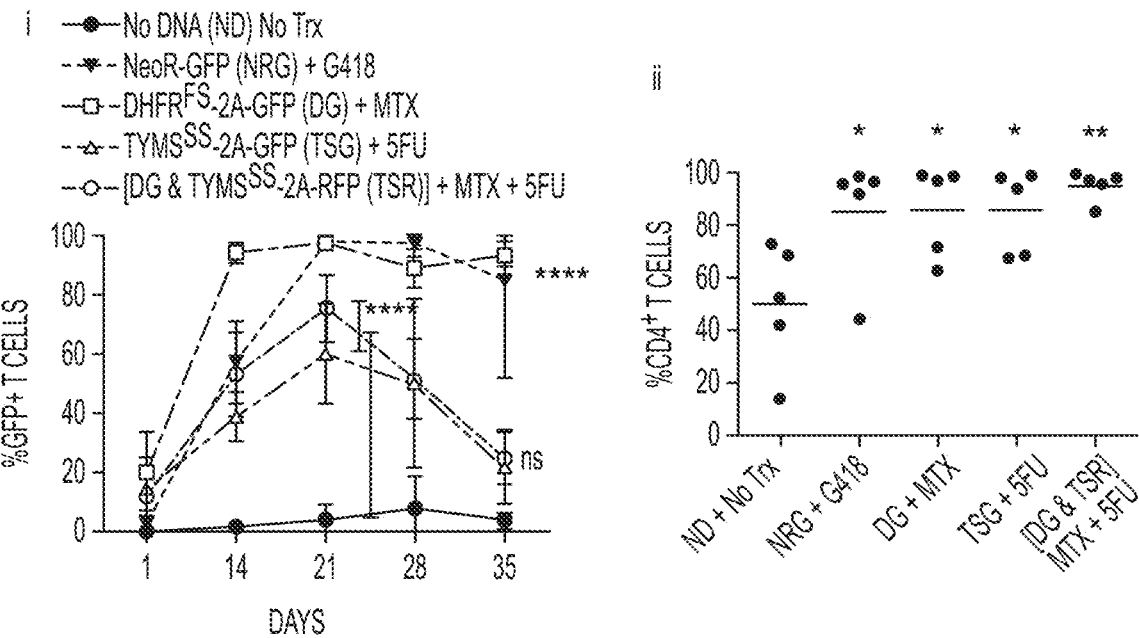
Figure 3C:
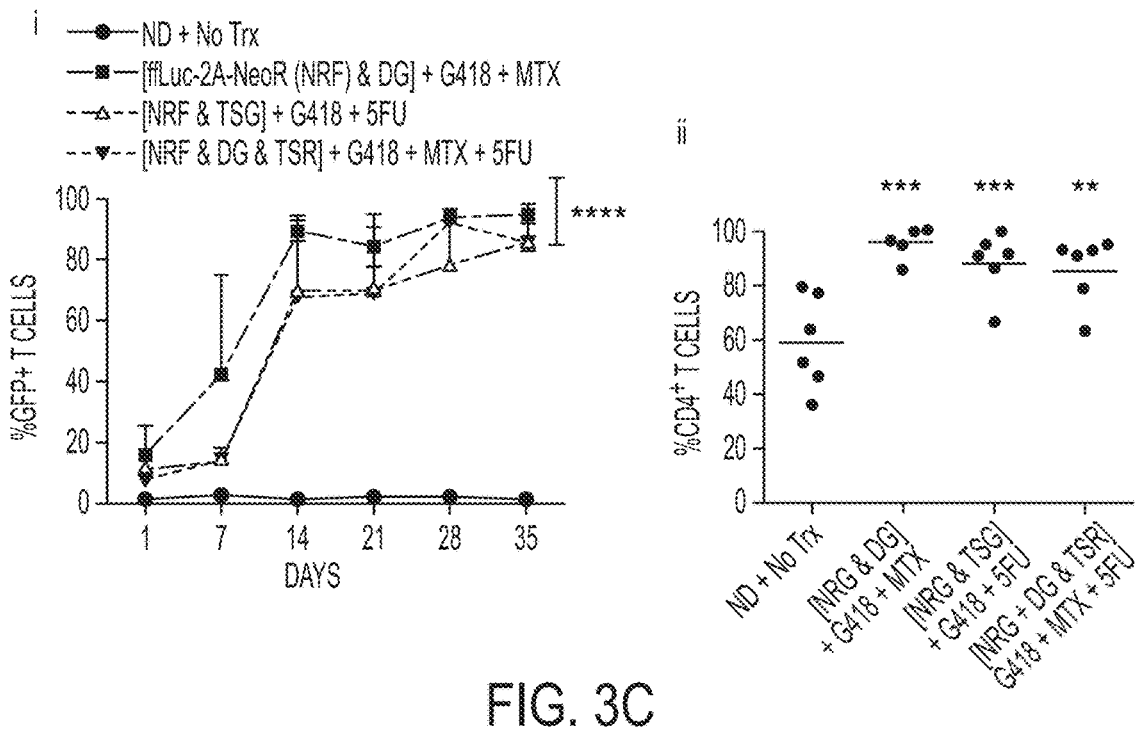

As demonstrated, TYMS$^{SS}$ enhances the ability of Jurkat expressing DHFR$^{FS}$ to survive in the presence of MTX and Pem, which both target endogenous DHFR and TYMS to prevent thymidine synthesis. Given the more robust survival to toxic MTX concentrations conferred by DHFR$^{FS}$ and TYMS$^{SS}$, experiments with MTX were undertaken to demonstrate anti-folate and AThy resistance. TYMS$^{SS}$ with DHFR$^{FS}$ were tested in human cells by electroporation into human PBMC. The day following electroporation, cells were stimulated with an OKT3-loaded AaPC capable of polyclonal T cell propagation. The propagation schematic is shown in FIG. 3A. Two days after AaPC stimulation, the co-cultures received 0.1 μM MTX, 5 μM 5-FU, or 1.4 mM G418 until day 14, as designated in FIG. 3. The co-cultures were re-stimulated with AaPC at a 1:1 ratio and given 50 IU/mL IL-2 every 7 days from day 1 to 35. Phenotypic changes in transgene expression were tracked during drug administration for the first 14 days and for the 21 days after drug administration had ended. The weekly changes in transgene expression can be noted in FIG. 3B-I, C-I, D-I.

Initial testing of DHFR$^{FS}$, TYMS$^{SS}$, and NeoR co-expressed with fluorescent proteins demonstrated rapid and persistent selection to nearly complete selection for expression of DHFR$^{FS}$ with MTX and NeoR with G418 (FIG. 3B-I). Survival and propagation of AThyR+ T cells (TAThyR) compared to No DNA T cells on day 21 showed that the presence of AThyR or NeoR transgene plays a role in T cell survival and growth (FIG. 4A). On day 35, total inferred cell count for T cells expressing AThyR and NeoR transgenes were compared to untreated No DNA T cells, and NeoR+ T cells were the only T cells with significantly inferior growth at Day 35 (FIG. 4B-I). In opposition to experiments in Jurkat, TYMS$^{SS}$ demonstrated selection within the population of surviving T cells on Day 21 in the presence of 5-FU. However, the selected TYMS$^{SS}$ expressing T cells did not persist to Day 35, and the lack of persistence was also noted when [DHFR$^{FS}$ & TYMS$^{SS}$] were selected using MTX and 5-FU. Without wishing to be bound by any theory, thymidine synthesis may be restored by TYMS$^{SS}$ and thymidine transporters then make thymine available to un-transformed cells. Without wishing to be bound by any theory, this is likely mediated by an equilibrative nucleoside transporter as the same transporter that permits 5-FU entry also mediates equilibrative transport of thymine. As TYMS$^{SS}$ restores thymidine synthesis in the presence of methotrexate, DHFR$^{FS}$ is no longer able to select for T cells expressing DHFR$^{FS}$ & TYMS$^{SS}$ as noted in FIG. 3B-I.

In order to achieve complete selection of TYMS$^{SS}$ for possible use in combination therapies, NeoR was co-electroporated into primary T cells with DHFR$^{FS}$, TYMS$^{SS}$, and [DHFR$^{FS}$ & TYMS$^{SS}$]. The only change made to the propagation method was the addition of 100 IU/mL IL-2 rather than 50 IU/mL from days 14-35 to supplement the poor outgrowth already noted in G418 selected T cells. The higher doses of IL-2 were insufficient to rescue poor outgrowth when G418 and 5-FU were combined for T cell selection (FIG. 4B-II). With the co-transfection of NeoR into DHFR$^{FS}$ and/or TYMS$^{SS}$ expressing T cells, nearly 100% transgenes selection was observed with the same transgene selection kinetics among all groups (FIG. 3C-I).

The influence of TYMS$^{SS}$ on DHFR$^{FS}$ selection in T cells subjected to MTX was tested. Plasmids expressing DHFR$^{FS}$ were co-electroporated into T cells along with either TYMS$^{SS}$ co-expressing RFP or a vector expressing RFP alone. This experiment followed the same strategy as described for FIG. 3B. Due to technical limitations, the total amount of DHFR$^{FS}$ expressing plasmid DNA electroporated into the same number of T cells was decreased. Consequently, fewer T cells initially expressed DHFR$^{FS}$ at the beginning of the experiment and DHFR$^{FS}$ was incompletely selected by the addition of MTX within a 14 day time period (FIG. 3D-I). The progressive loss of DHFR$^{FS}$ after day 14 is reminiscent of TYMS$^{SS}$ expression in FIG. 3B-I. This demonstrates that AThyR transgenes must select for a large portion of the T cell population to maintain stable expression within the population. With regards to the influence of TYMS$^{SS}$ on the selection of DHFR$^{FS}$, it appears that TYMS$^{SS}$ blunts DHFR$^{FS}$ selection in T cells as selection of [DHFR$^{FS}$ & RFP] expressing T cells was more robust than selection of [DHFR$^{FS}$ & TYMS$^{SS}$] expressing T cells. This is attributed to the restoration of thymidine synthesis in the presence of TYMS$^{SS}$ (FIG. 3D-I). The presence of 5-FU prevents selection of DHFR$^{FS}$ with or without TYMS$^{SS}$, and this is attributed to the TYMS$^{SS}$ independent inhibition of mRNA and rRNA.

Figures 6A, 6B, 6C:
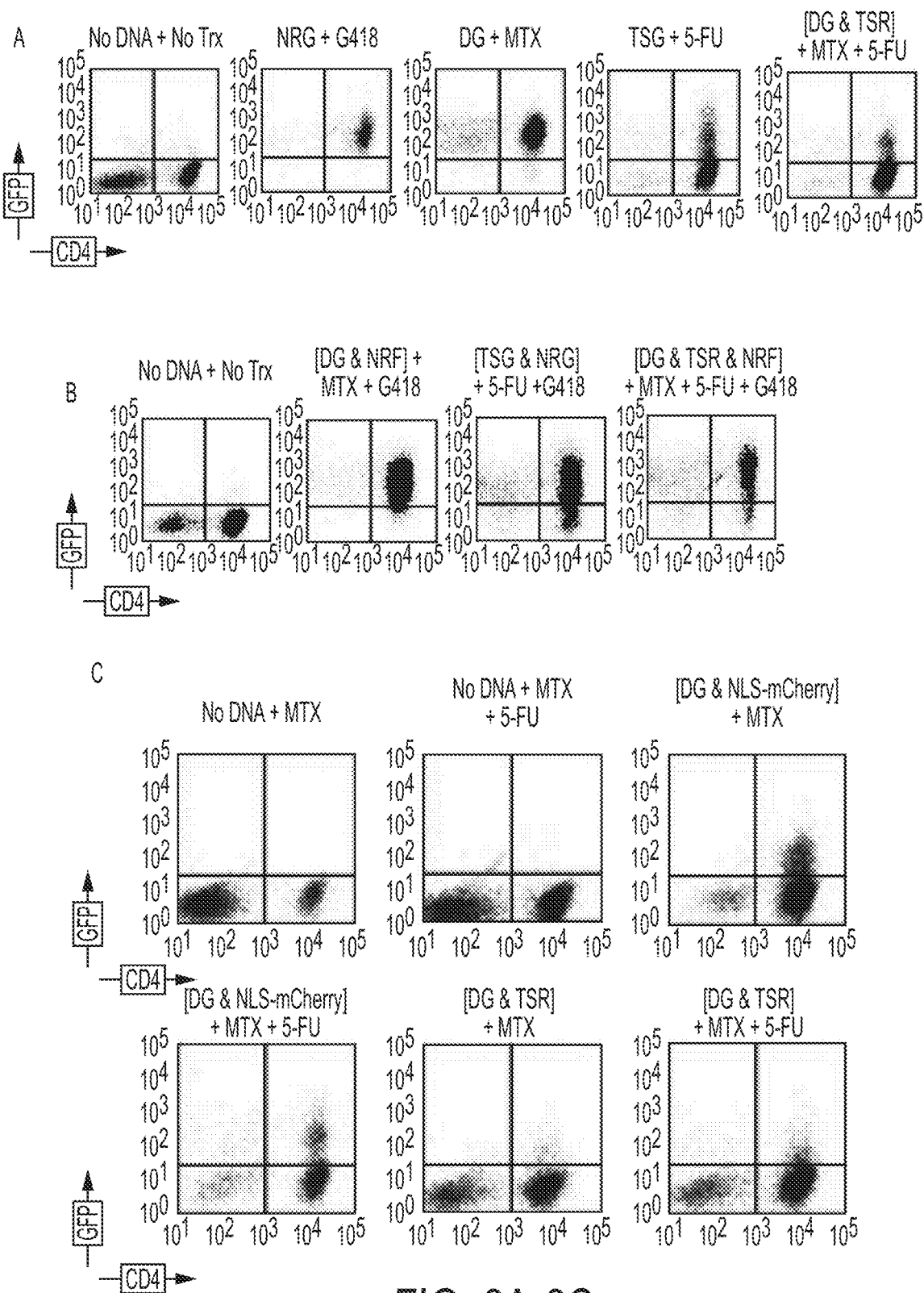
FIG. 6A depicts experimental conditions that corresponds to the experiment described for FIG. 3B.
FIG. 6B depicts experimental conditions that corresponds to the experiment described for FIG. 3C.
FIG. 6C depicts experimental conditions that corresponds to the experiment described for FIG. 3D.
Figure 6D:
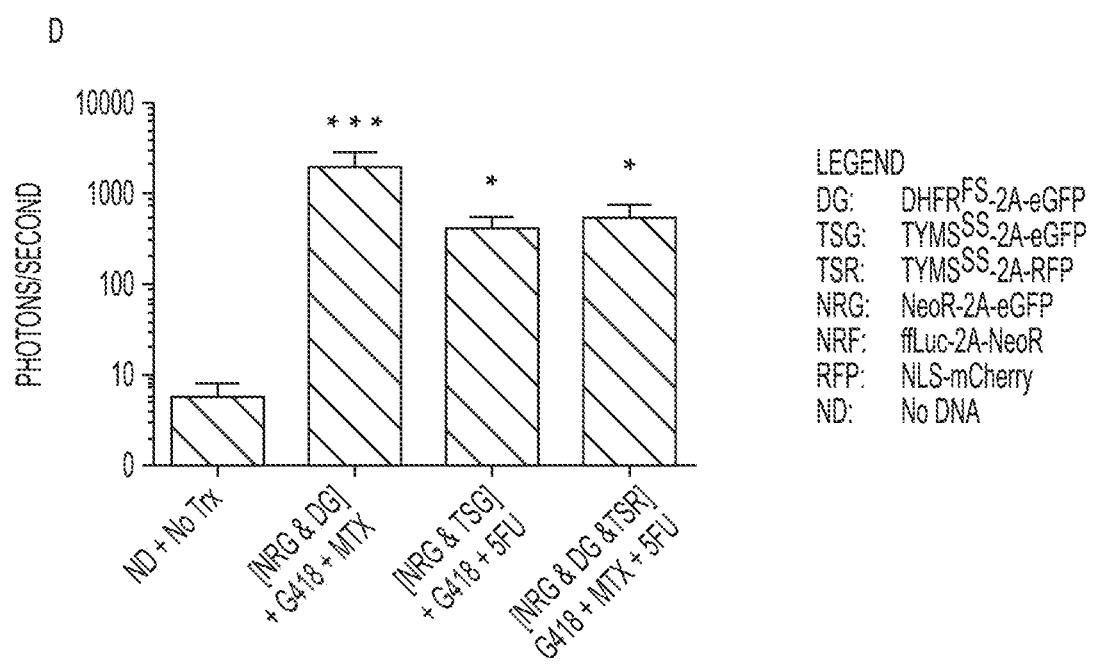
FIG. 6D shows that the presence of ffLuc-2A-NeoR-NRF—on day 35 for experiment noted in FIG. 6B is demonstrated using D-luciferin to induce T cell chemiluminescence. Each experiment was independently repeated at least twice with 6 replicates. Representative flow plots are depicted. *=p<0.05, =p<0.01, *=p<0.001.

It was also noted that transgenic selection tended to increase the population of CD4+ T cells by day 35 in all T cell experiments, which was not seen with un-modified T cell cultures. This was noted in any experiment involving one or more transgenes selected in the presence of cytotoxic drug (FIG. 3B-II, 3C-II, 3D-II, respective flow plots seen in FIGS. 6A, 6B, and 6C). The experiment in FIG. 3D-II demonstrates that it is not caused by cytotoxic drug, rather, the presence of transgene in combinations with cytotoxic drug leads to CD4+ T cell predominance by day 35. The selection towards CD4+ T cell predominance was not noted 7 days after initial drug selection for AThyR+ T cells (FIG. 4C), which is consistent with previously published findings using DHFR$^{FS}$ T cells (Jonnalagadda et al., *Gene therapy* 2013, 20(8):853-860). The longer period of follow-up than prior experiments demonstrated a previously unknown phenomenon that CD8+ T cells are unable to persist for long periods of time following cytotoxic insult, or are selectively outgrown by CD4+ T cells.

C. MTX Increases Cis-Transgene Expression in DHFR$^{FS+}$ T Cells

Figure 5A:
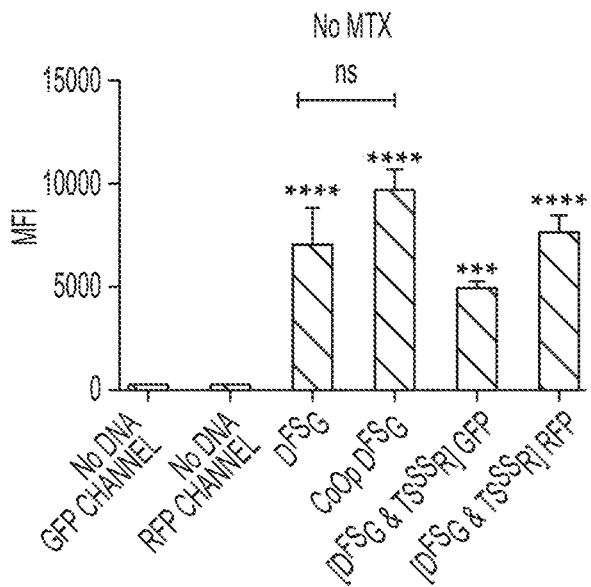
FIG. 5A-H: Cis-transgenes downstream of DHFR$^{SS}$ increase in the presence of MTX independent of mRNA sequence and the increase is suppressed by restoration of thymidine synthesis.
Figure 5B:
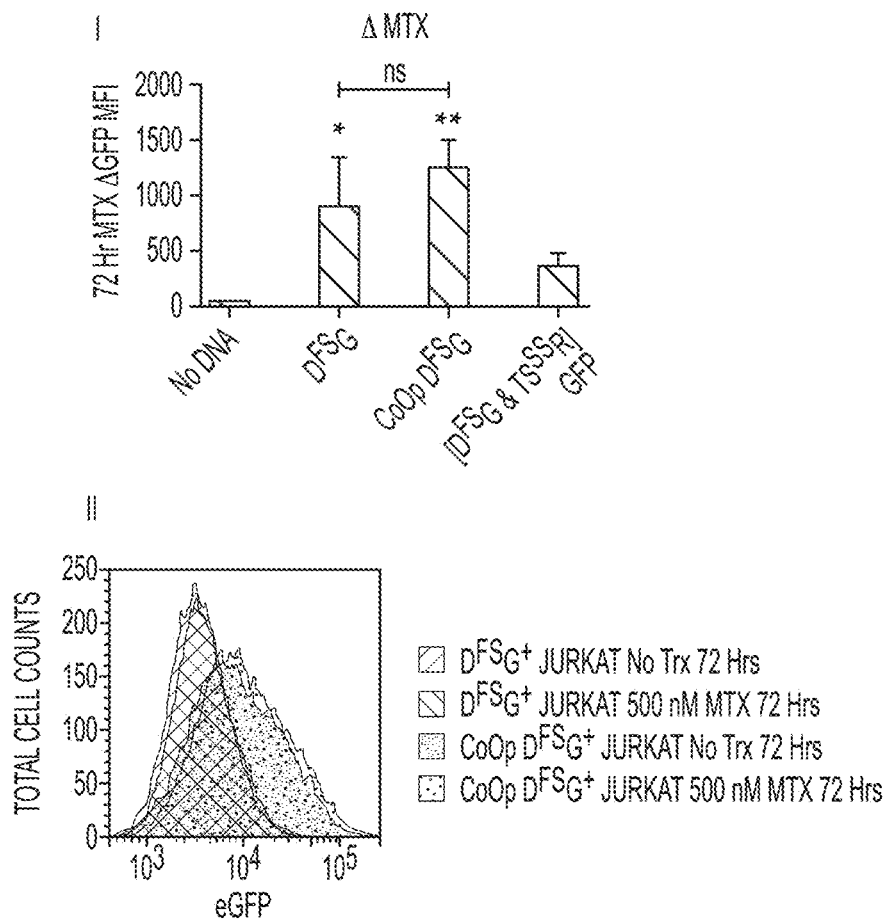

MTX mediated changes in transgene expression are useful for in vivo control of transgene expression in both animals and humans. Thus, according to the present invention, MTX, a clinically available drug, is used to mediate transgene expression either up or down in T cells. To investigate the persistence of this regulation, DHFR$^{FS}$, CoOp DHFR$^{FS}$, and [DHFR$^{FS}$ & TYMS$^{SS}$] expressed in Jurkat were selected in 1 μM MTX for 2 weeks and rested for 3-5 weeks before testing MTX mediated regulation of DHFR$^{FS}$ expression. The expression of DHFR$^{FS}$ and codon optimization (CoOp) DHFR$^{FS}$ selected for uniform expression in Jurkat T cell line is shown in FIG. 5A. CoOp DHFR$^{FS}$ did not contribute to a significantly higher expression of DHFR$^{FS}$ as indicated by a cis-expressed eGFP, nor did it prevent MTX induced increases in transgene expression as noted in FIG. 5B. This was unexpected. However, the loss of MTX induced increase in DHFR$^{FS}$ expression was noted when TYMS$^{SS}$ was co-expressed with DHFR$^{FS}$ as seen in FIG. 5A and FIG. 5B. The addition of TYMS$^{SS}$ led to an insignificant reduction in the expression of native DHFR$^{FS}$ in the absence of MTX. The addition of MTX was unable to induce the same increase in DHFR$^{FS}$ expression seen during the sole expression of either DHFR$^{FS}$ version Thus, TYMS$^{SS}$ is playing a role in the MTX inducible increase of DHFR$^{FS}$. In certain experiments, the co-expression of TYMS$^{SS}$ with DHFR$^{FS}$ in Jurkat blunts the MTX induced increase in eGFP MFI (FIG. 3B-I). Thus, DHFR$^{FS}$ maintains MTX-inducible expression of cis-transgenes which is dependent on MTX mediated inhibition of TYMS.

Figure 5C:
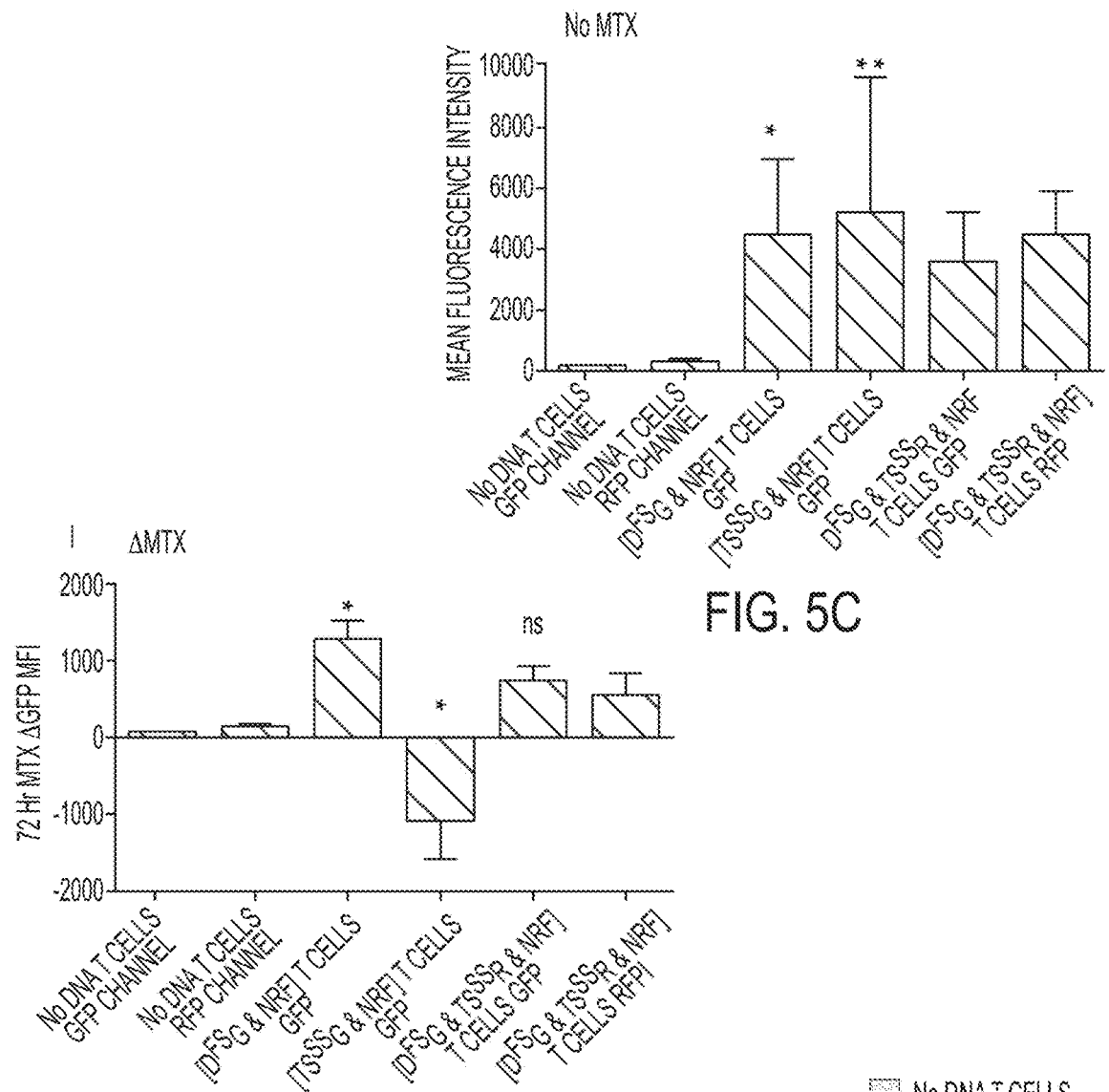
Figure 5D:
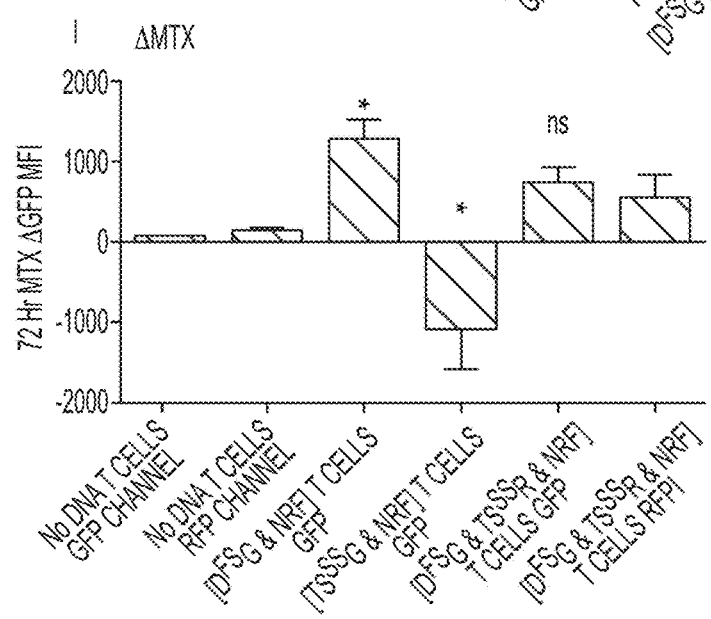
Figure 5D:
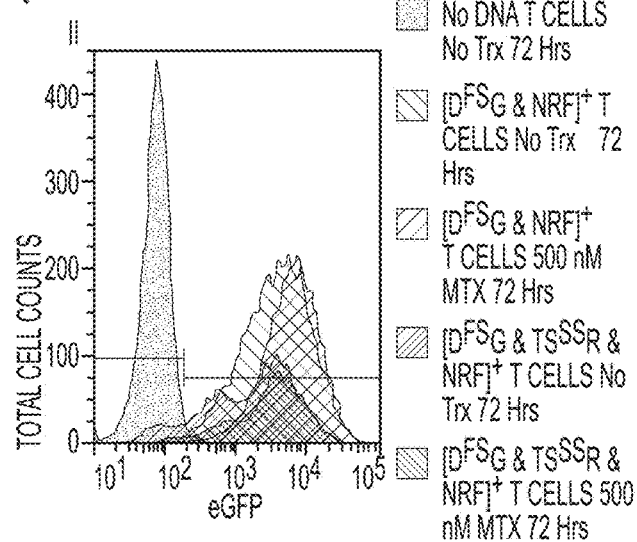

Expression of these transgenes in primary T cells was next attempted to recapitulate the findings of MTX inducible increases in DHFR$^{FS}$ expression that were prevented by TYMS$^{SS}$. Expression of DHFR$^{FS}$, TYMS$^{SS}$, or [DHFR$^{FS}$ & TYMS$^{SS}$] was achieved with stability and purity by selecting from days 2-14 of propagation with the respective drugs MTX, 5-fluorouracil (5-FU), and G418 when the selection vector containing neomycin resistance was included. The expression of DHFR$^{FS}$ linked eGFP and TYMS$^{SS}$ linked RFP can be noted in FIG. 5C for DHFR's, TYMS$^{SS}$, or [DHFR's & TYMS$^{SS}$]. Again it is noted that DHFR$^{FS}$ expression is increased in the presence of MTX (FIG. 5D), but this increase is blunted and no longer significant when TYMS$^{SS}$ is co-expressed with DHFR$^{FS}$, as in Jurkat. Of note, expression of TYMS$^{SS}$ without DHFR$^{FS}$ was successfully achieved in primary T cells by selection with 5-FU and a trans neomycin resistance gene selected by G418. When TYMS$^{SS}$ was tested for inducible changes in the presence of high doses of MTX (FIG. 5D), it was found that TYMS$^{SS}$ linked RFP decreased significantly. The presence of DHFR$^{FS}$ along with TYMS$^{SS}$ in the same treatment conditions prevented this decrease. MTX induced a reduction in the expression of TYMS$^{SS}$ that MTX resistant DHFR$^{FS}$ restored. These findings could indicate that TYMS$^{SS}$ is being repressed by a lack of 5, 10-methylenetetrahydrofolate (5, 10 CH$_2$THF). Without being limited by any particular mechanism, it is proposed that MTX, which leads to a drop in 5, 10 CH$_2$THF, is causing TYMS protein to bind TYMS and TYMS$^{SS}$ mRNA preventing expression. It should be noted that TYMS$^{SS}$ is equivalent to the native sequence with the exception of the point mutations.

Figures 5E, 5F:
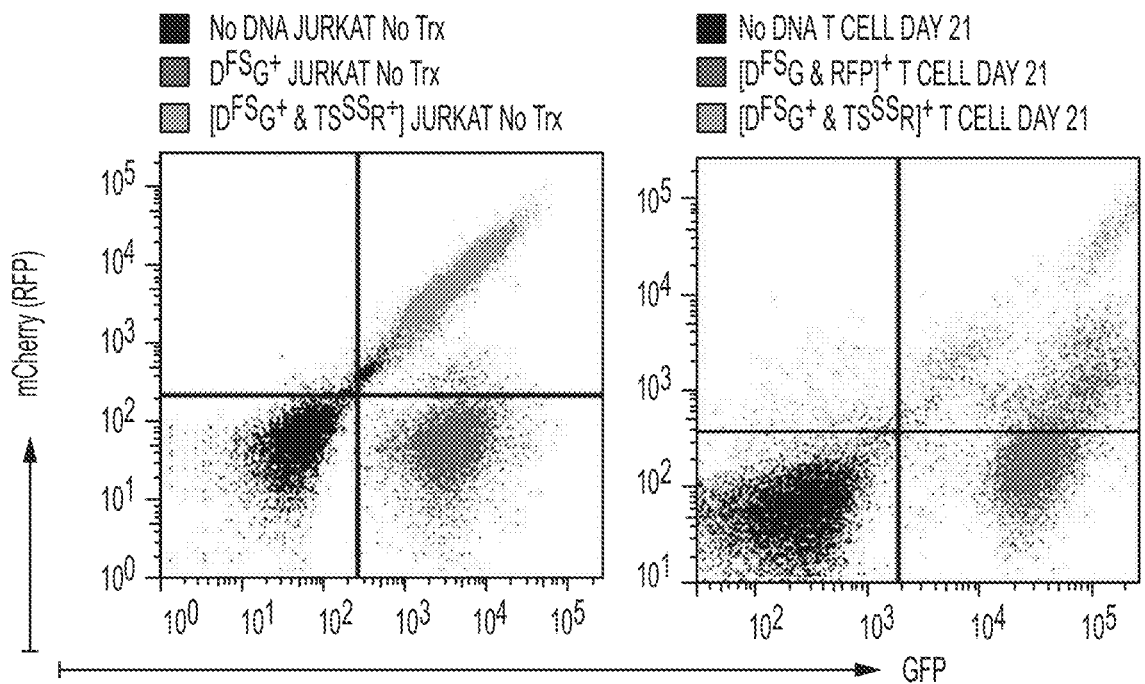
Figure 5G:
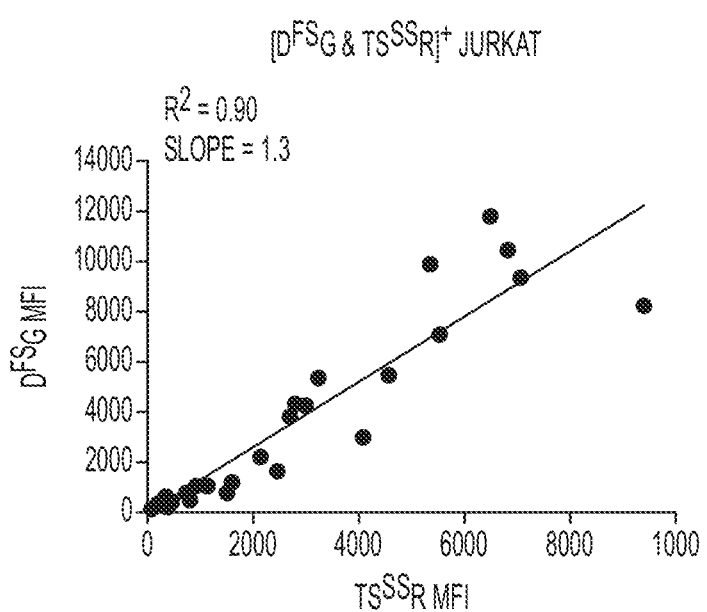

Based on findings in FIG. 5A-B, it is proposed that DHFR$^{FS}$ expression is also regulated by the synthesis of thymidine. Likewise, based on findings in FIGS. 5C & D, it is proposed that TYMS$^{SS}$ expression is regulated by the synthesis of tetrahydrofolate (THF). As a derivative of THF is used to make thymidine, a logical conclusion was made that DHFR$^{FS}$ regulates the expression of TYMS$^{SS}$ and TYMS$^{SS}$ regulates the expression of DHFR$^{FS}$. Therefore, a correlated expression of DHFR$^{FS}$ and TYMS$^{SS}$ should be noted within individual cells. When a correlated expression of DHFR$^{FS}$ and TYMS$^{SS}$ was tested by observing flow plots of Jurkat in FIG. 5E and primary T cells in FIG. 5F, it was noted. A control RFP vector co-expressed with DHFR$^{FS}$, but not modulated by cis expression with TYMS$^{SS}$, did not appear to have the same co-expression pattern (FIG. 5F). To quantify this observation, Jurkat expressing [DHFR$^{FS}$ & TYMS$^{SS}$] were treated with antifolates MTX, pemetrexed, and raltitrexed at varying concentrations for 2 weeks. DHFR$^{FS}$ linked eGFP MFI and TYMS$^{SS}$ linked RFP MFI for each separate well were then plotted and correlated. The linked expression between DHFR$^{FS}$ and TYMS$^{SS}$ was significant and fit a linear regression (FIG. 5G). These findings support a general mechanism for regulation of DHFR and TYMS, which leads to a linear co-expression of DHFR$^{FS}$ and TYMS$^{SS}$. This model is shown in FIG. 5H.

Figure 5H:
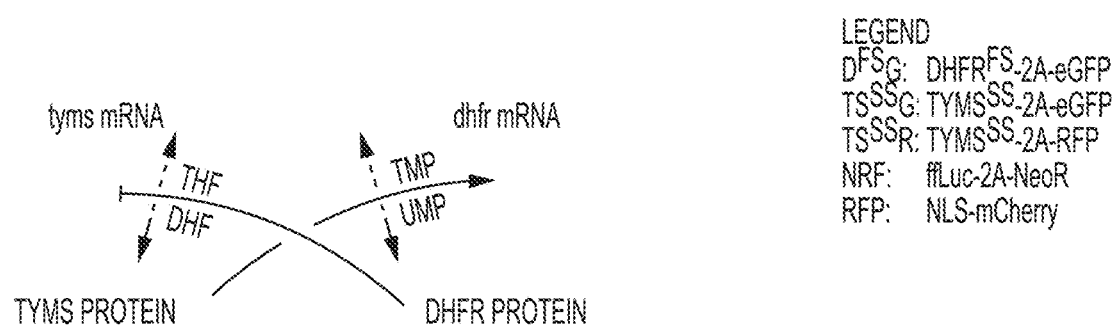
Figure 5I:
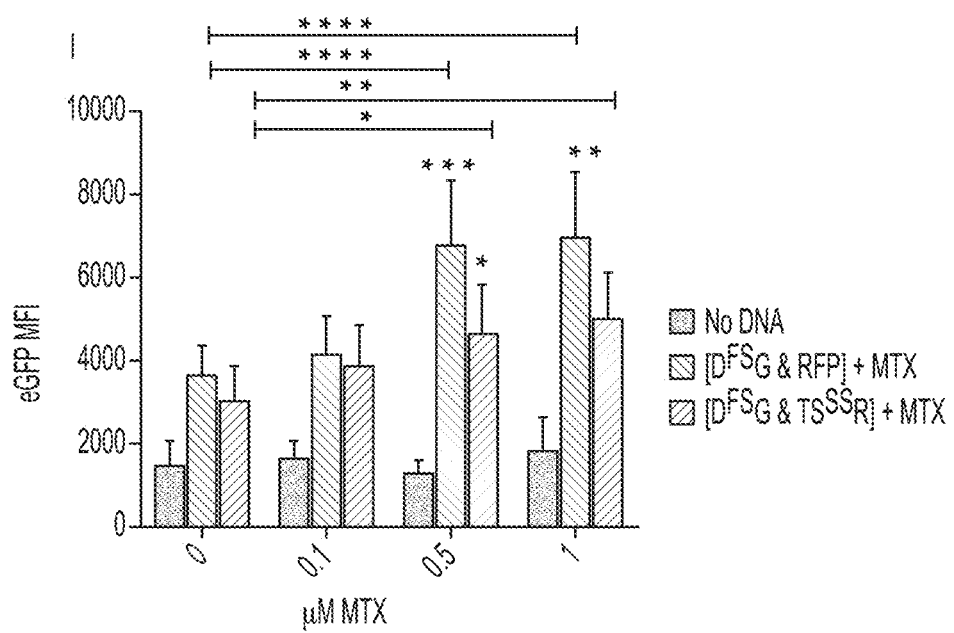
Figure 5J:
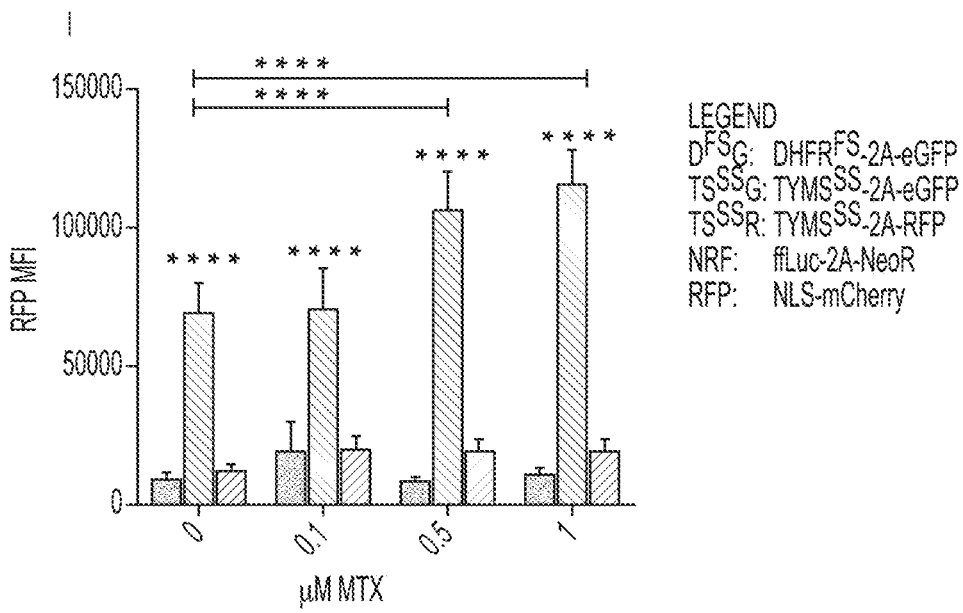

Based on the above model in FIG. 5H, it appears that TYMS$^{SS}$ expression will be stabilized by DHFR$^{FS}$ from strong expression changes in the presence of MTX. This was tested in FIG. 5I with primary T cells expressing DHFR$^{FS}$ along with either RFP or TYMS$^{SS}$ linked to RFP by applying increasing doses of MTX. As expected, DHFR$^{FS}$ linked eGFP was increased by increasing concentrations of MTX, and this increase was blunted by the presence of TYMS$^{SS}$ (FIG. 5I-J). This conserves the model in FIG. 5H where restoration of thymidine synthesis prevents the MTX induced increase in DHFR$^{FS}$. Further conserving the model, RFP linked to TYMS$^{SS}$ did not significantly increase over any concentration of MTX used (FIG. 5I-J). When DHFR$^{FS}$ linked eGFP increased so too did the control RFP, and an increase in the expression of RFP alone was not expected. A possible explanation is that this increase was noted above 0.5 µM MTX, and DHFR$^{FS}$ alone is only resistant to 0.5 µM MTX.[9] This suggests that higher doses of MTX begin to select for cells with higher gene content of DHFR$^{FS}$ and associated transgenes. Notably, DHFR$^{FS}$ co-expressed with TYMS$^{SS}$ is resistant to concentrations of up to 1 µM MTX. This further supports the use of TYMS$^{SS}$ to modulate transgene expression and prevent unwanted selection towards higher gene expression levels of genes expressed in cis or trans with DHFR$^{FS}$.

Figure 5K:
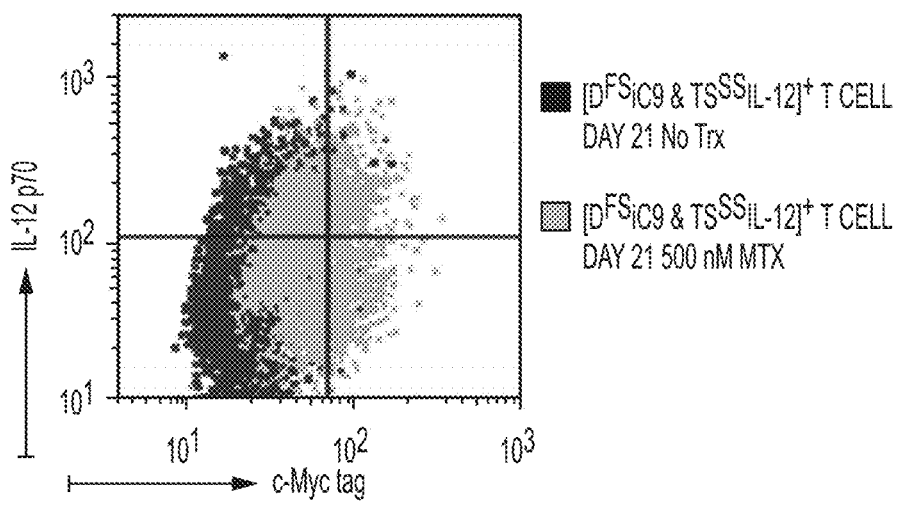
Figure 5L:
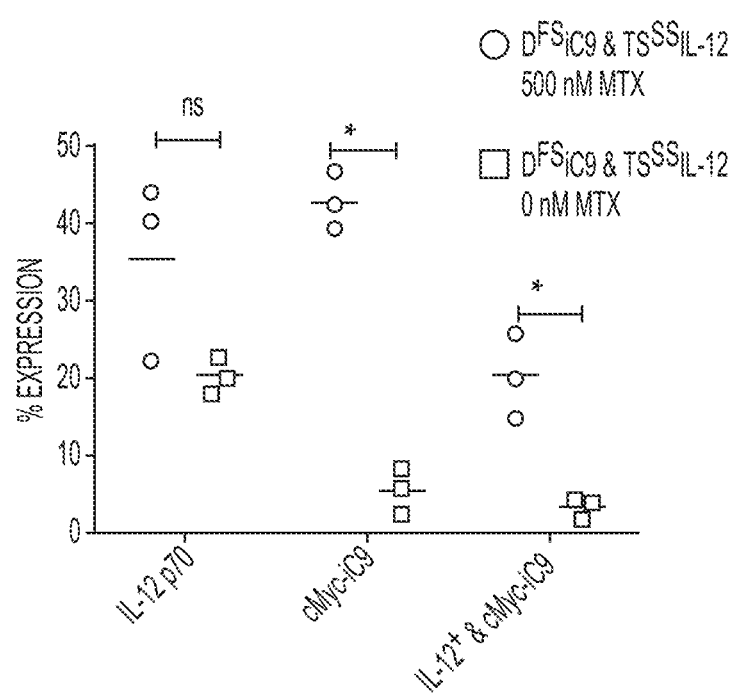

Next, a construct of DHFR$^{FS}$ cis expressing an inducible suicide gene-inducible caspase 9 (iC9) was employed. This construct, called D$^{FS}$iC9, selects for T cells expressing D$^{FS}$iC9 in the presence of MTX and ablates D$^{FS}$iC9+ T cells in the presence of drug that activates iC9 to induce apoptosis. Based on the above findings, the DHFR$^{FS}$ in D$^{FS}$iC9 could be used to modulate and potentially ablate the expression of a transgene of interest which is otherwise too toxic to express without regulation. Interleukin-12 (IL-12) is such a transgene. IL-12 is a cytokine capable of inducing a strong immune response against tumor from tumor specific T cells. However, systemic IL-12 is highly toxic and of low efficacy. Presented here is an alternative approach where IL-12 is expressed cis to TYMS$^{SS}$ in order to decrease and stabilize the expression level of IL-12. In FIG. 5K, a flow plot demonstrates the expression of IL-12 cis expressed with TYMS$^{SS}$ and iC9 cis expressed with DHFR$^{FS}$ expression. The donor cells were either left untreated or treated with high doses of MTX for 7 days. This expression pattern appears to indicate that IL-12 can be stably expressed even in prolonged toxic doses of MTX. A further analysis of similarly manipulated donors (FIG. 5L) demonstrates the potential of TYMS$^{SS}$ when co-expressed with DHFR$^{FS}$ to stabilize the expression of the potentially toxic transgenes of interest—IL-12.

Figure 3D:
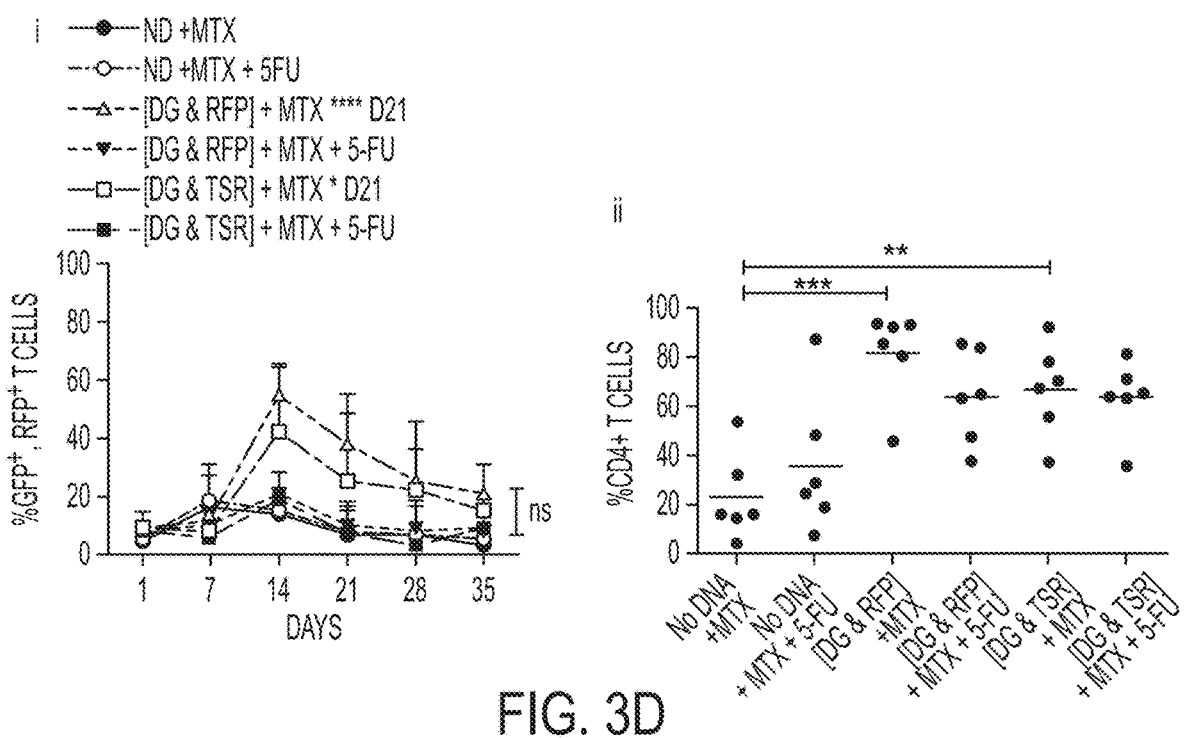
Figures 4A, 4B, 4C:
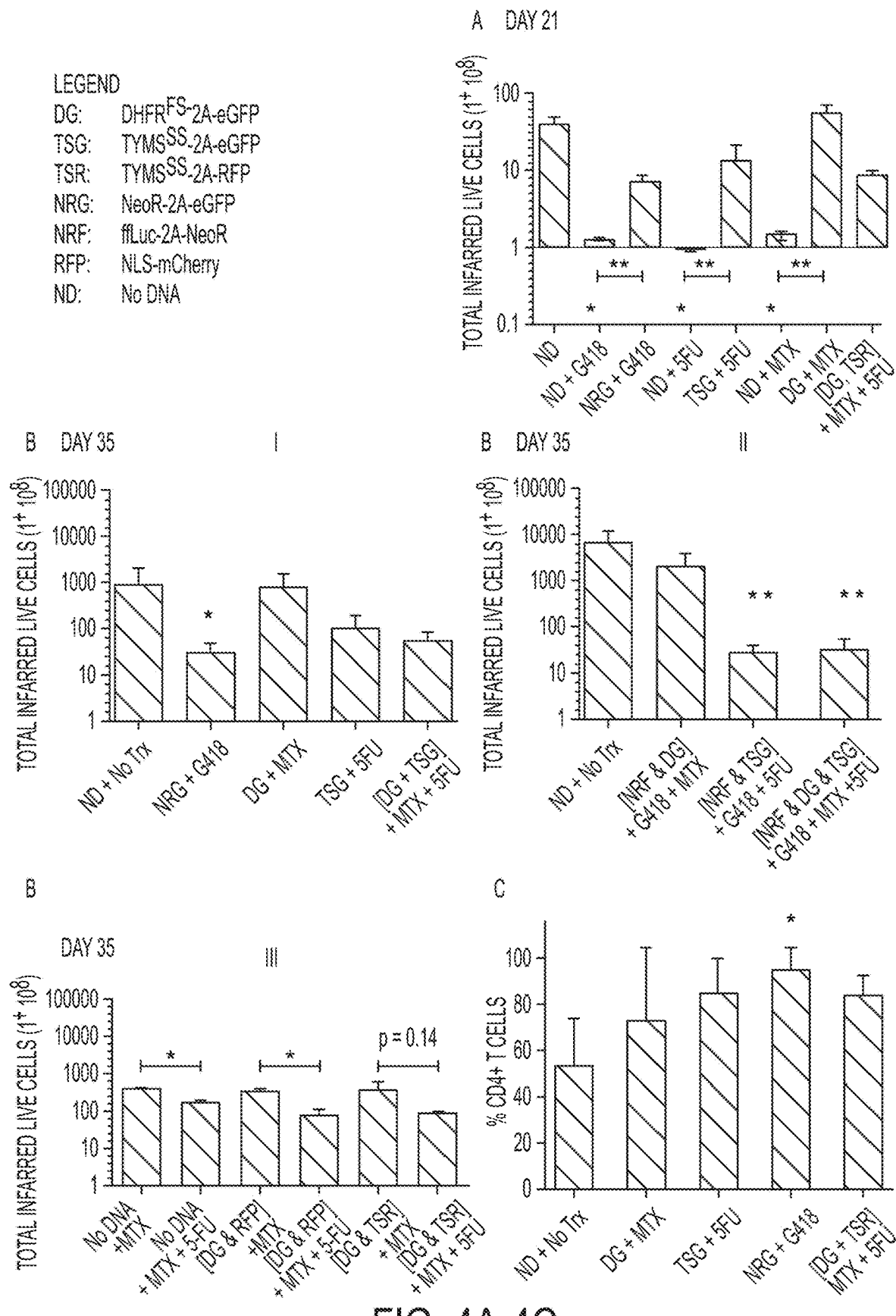
FIGS. 4A-4C show the propagation characteristics of AThyR+ T cells in the presence or absence of MTX, 5-FU, and/or G418.
Figure 7A:
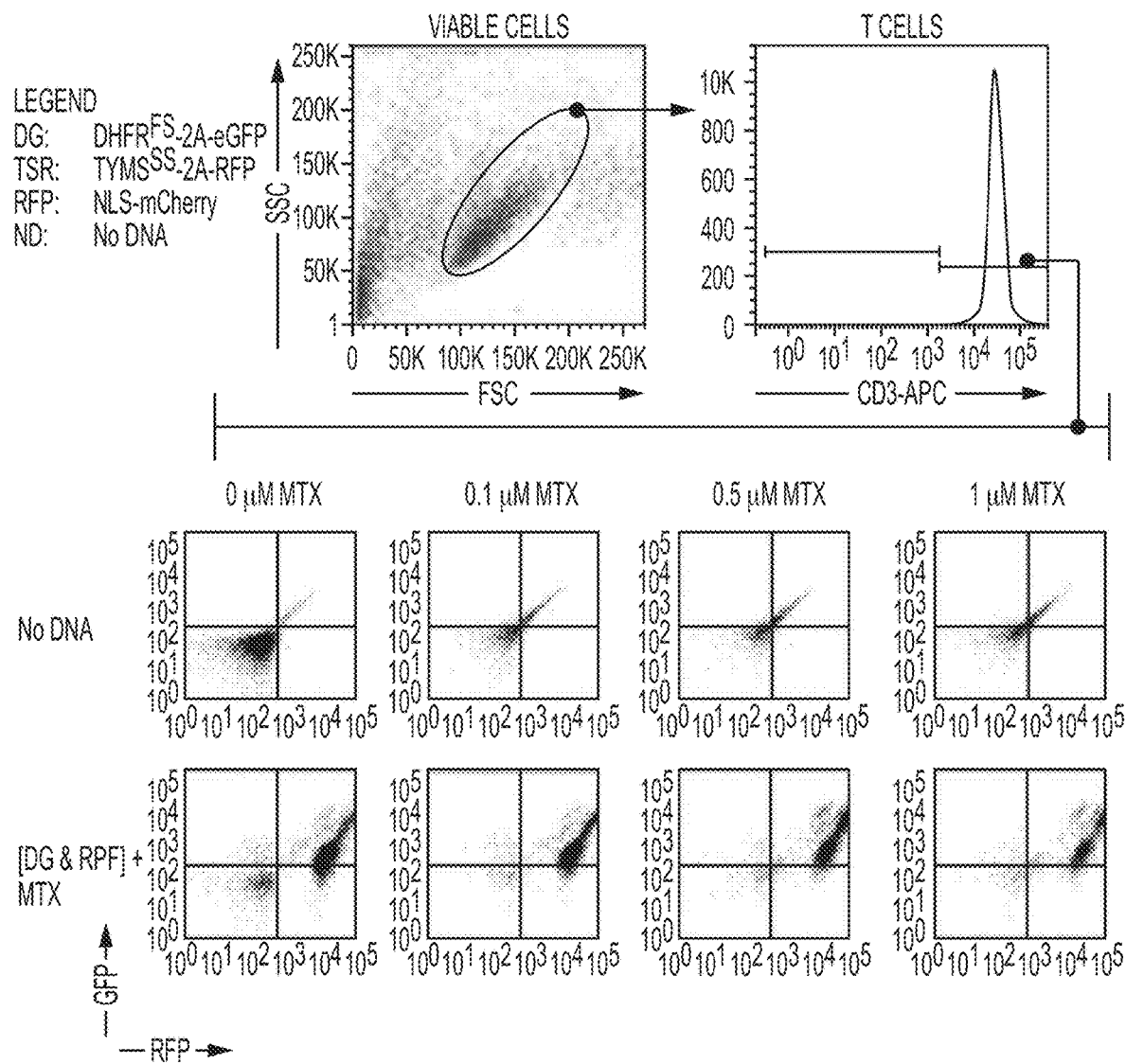
FIG. 7A shows the gating strategy and representative flow plots.
Figure 7A:
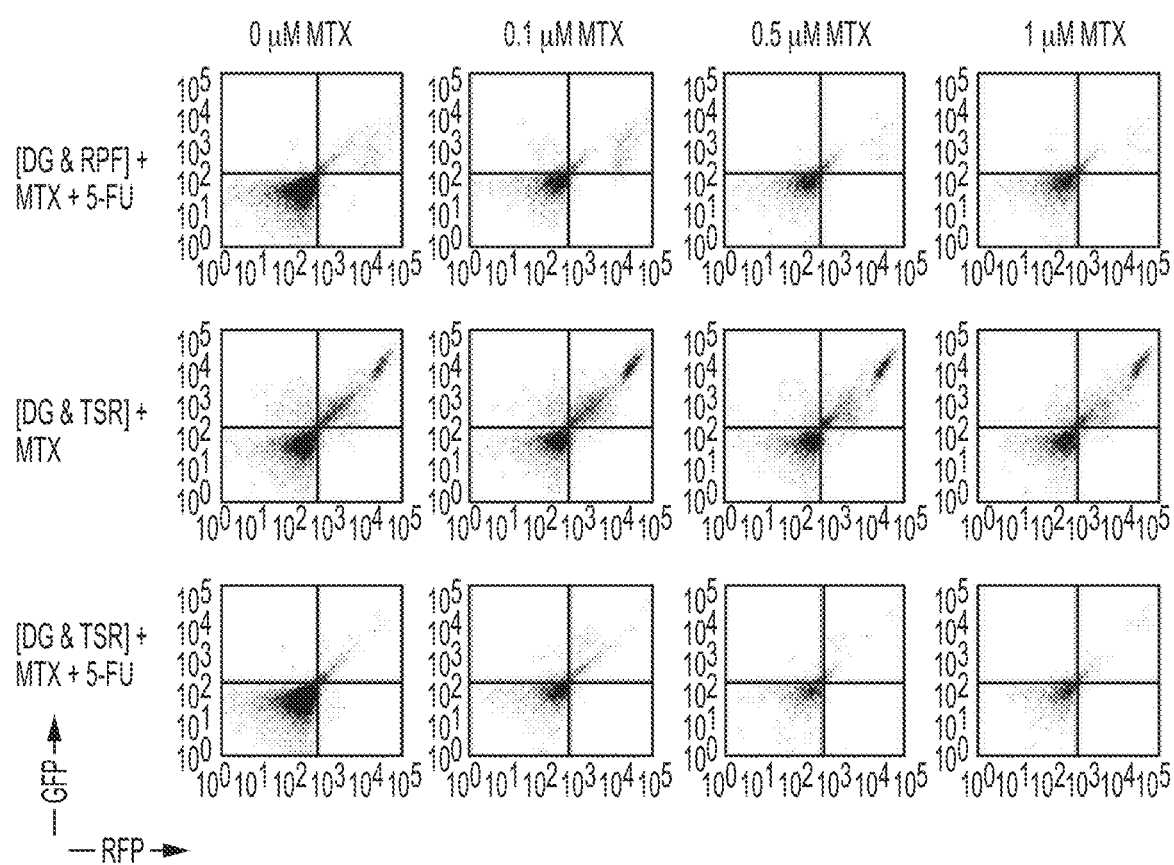
Figure 7B:
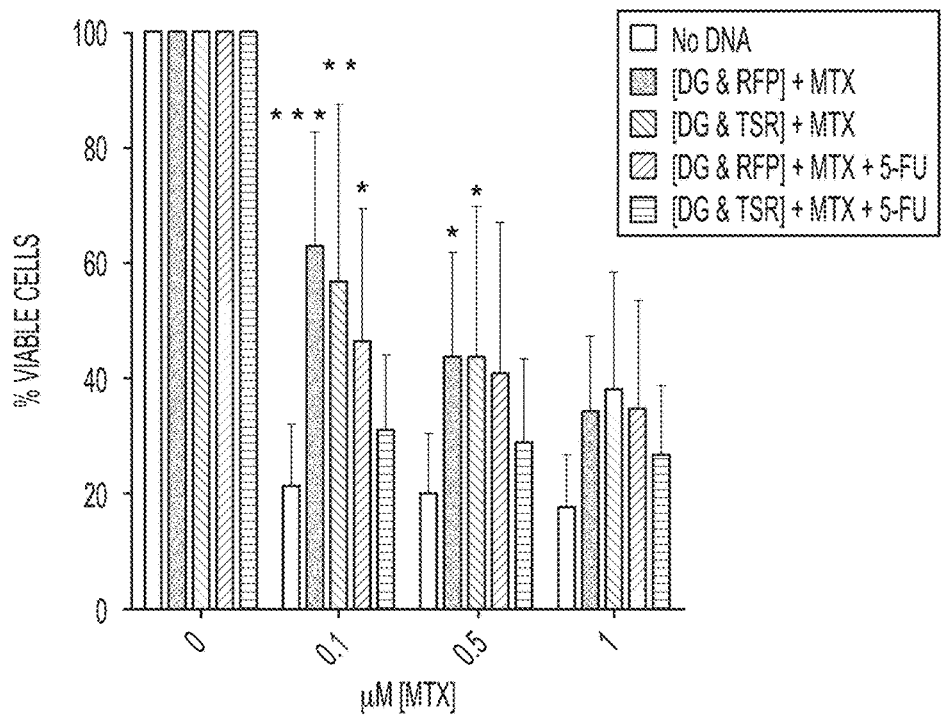
FIG. 7B shows enhanced viability of AThyR+ T cell cultures.
Figure 7C:
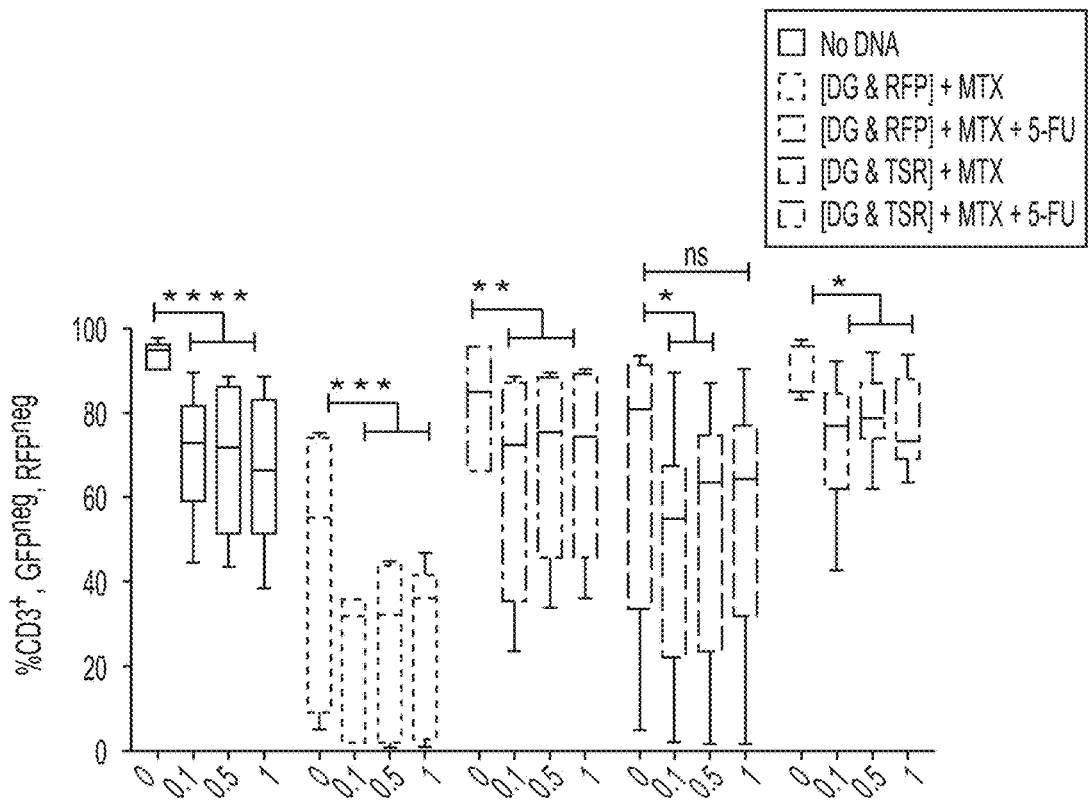
FIG. 7C shows assessment of Viable, CD3$^+$, GFPneg, RFP$^{neg}$ T cells (AThyR$^{neg}$) for survival. Each experiment was independently repeated at least twice with 6 biologic replicates total. Representative flow plots from one are depicted; ns=no significance; *=p<0.05, =p<0.01, *=p<0.001; ****=p<0.0001.

T cells from the experiment shown in FIG. 3D were also subjected to varying concentrations of MTX. On day 35, T cells received anti-CD3/CD28 stimulation and were subjected to a range of MTX from 0 to 1 µM for 72 hours. On day 35, no T cell group significantly expressed DHFR$^{FS}$, as indicated by co-expressed eGFP, above background (FIG. 3D-I). However, DHFR$^{FS}$+ T cells selected with MTX alone persisted enough to significantly improve survival when MTX was re-introduced at concentrations up to 0.5 µM MTX (FIG. 7B). Flow plots in FIG. 7A demonstrate MTX-dependent increases in transgene expression and improved survival for transgene expressing T cells for one donor. It should be noted that the addition of TYMS$^{SS}$ in [DHFR$^{FS}$+ & TYMS$^{SS}$]+ T cells permitted the survival of transgene negative cells at 1 µM MTX, which was not seen in TYMS$^{SS\ neg}$ T cells subjected to MTX (FIG. 7C).

D. AThyR Permits Independent Selection for Transgenes of Interest

AThyRs are human proteins and therefore have lower immunogenicity in humans than NeoR or similar drug resistance transgenes, typically originating from bacteria. Thus, using AThyRs to select transgenes of interest is desirable due to lower immunogenicity, and ease of use in vitro. As a demonstration, the suicide gene inducible caspase 9 (iC9) was selected by co-expressing iC9 with DHFR$^{FS}$ in a construct designated D$^{FS}$iC9 (FIG. 8A). Current methods to select iC9 utilize surface-expressed antigen and isolation by magnetic beads. However, this method of selection is more labor intensive than adding drug and does not add the functionality of AThy resistance. The D$^{FS}$iC9 plasmid significantly selected for survival in T cells after 7 days of AaPC based stimulation including days 2-7 days in 0.1 µM MTX (FIG. 8B). Next, D$^{FS}$iC9 was co-electroporated with CAR to express in T cells. The CAR was specifically selected by a CAR exodomain binding ligand (CARL)+ K562 AaPC (Rushworth et al., supra) while D$^{FS}$iC9 was selected using 0.1 µM MTX. After days 2-14 in 0.1 µM MTX, CAR+ D$^{FS}$iC9+ T cells were rested from MTX or selected for another 7 days in 0.1 µM MTX. T cells selected in 0.1 µM MTX from day 2-21 are shown in FIG. 8C compared to mock-electroporated T cells. As before, there is no selection towards CD4+ T cell predominance following MTX selection by day 21.

These cells also demonstrated cytotoxicity at the levels expected for the given 5:1 target to effector ratio (FIG. 8D). Co-expressing DHFR$^{FS}$ with iC9 rather than CAR added the potential to ablate T cells through the addition of iC9 chemical inducer of dimerization AP20187 (FIG. 8E). The addition of AP20187 significantly depleted resting CAR+ T cells independent of MTX. This demonstrates that $D^{FS}iC9$ can effectively select for iC9 expression and deplete genetically-modified T cells as necessary. The use of $DHFR^{FS}$ has the advantage of selecting transgene expression in T cells independent of antigen-specificity and antigen expression.

Example 2

Materials and Methods

Healthy donor derived peripheral blood from MDACC Blood Bank, Houston, Tex., was subjected to density gradient centrifugation to isolate mononuclear cells which were either rested in complete media (CM) or frozen as previously outlined. The use of rested or frozen peripheral blood derived mononuclear cells (PBMC) is outlined in each experiment. T cells from PBMC were stimulated using thawed OKT3 antibody-loaded K562 clone #4, an activating and propagating cell (AaPC). See Singh H, et al, *PloS one* 2013, 8(5). The presence of mycoplasma was tested in AaPC before stimulation of T cells. Cell counting was accomplished by 0.1% Trypan Blue (Sigma-Aldrich, T8154) exclusion using automated cell counting (Nexcelcom, Lawrence, Mass.). Cell Isolation was accomplished using magnetic bead based sorting with the CD4+, CD25+ Regulatory T Cell Isolation Kit following the manufacturer's instructions (Miltenyi Biotec, San Diego, Calif., 130-091-301). Briefly, CD4+ T cells were negatively selected before sorting one time with anti-CD25 beads was used to differentiate between effector T cells ($CD25^{neg}$) and $T^{reg}$ ($CD25^{pos}$).

Culture Conditions: Acellular stimulation was accomplished as previously described using soluble anti-CD3—30 ng/mL, anti-CD28—100 ng/mL, and human IL-2—50 IU/mL, as previously described. When indicated, the following drugs were used: 5-FU, MTX, cisplatin (CDDP), pemetrexed, raltitrexed, G418, hygromycin B, zeocin, rapamycin, metformin, AICARtf/inosine monophosphate (IMP) cyclohydrolase (ATIC) dimerization inhibitor (iATIC) (Table 5). Acellular stimulation experiments received addition of toxic drug or treatment on the same day as stimulation.

TABLE 5

Chemical Agents

| Agent | Manufacturer | ID No. |
|---|---|---|
| 5-fluorouracil | APP Pharmaceuticals, Schaumburg, IL | NDC 63323-117-10 |
| Methotrexate | Hospira, Lake Forest, IL | NDC 61703-350-38 |
| CDDP | Pfizer, New York, NY | NDC 0069-0084-07 |
| Pemetrexed | Lilly, Indianapolis, IN | NDC 0002-7640-01 |
| Raltitrexed | Abcam Biochemicals, Cambridge, MA | Ab142974 |
| iATIC | EMD Millipore | 118490 |
| G418 | Invivogen, San Diego, CA | Ant-gn-1 |
| Hygromycin | Invivogen | Ant-hg-1 |
| Zeocin | Invivogen | Anti-zn-1 |
| Rapamycin | Wyeth, Philadelphia, PA | NDC 0008-1030-04 |

DNA Expression Plasmids:

Selection vectors: FLAG-$DHFR^{FS}$-2A-eGFP pSBSO (noted as $DHFR^{FS}$-GFP (DG)), FLAG-$TYMS^{SS}$-2A-eGFP pSBSO (noted as $TYMS^{SS}$-GFP (TSG)), NLS-mCherry pSBSO (RFP), FLAG-$TYMS^{SS}$-2A-NLS-mCherry pSBSO (noted as $TYMS^{SS}$-RFP (TRG)), Neomycin Resistance (NeoR)-2A-eGFP pSBSO (noted as NeoR-GFP (NRG)), and Myc-ffLuc-NeoR pSBSO (NRF), were designed constructed and utilized as previously described. Sleeping Beauty (SB) Indirect/Direct Repeat (IR/DR) Sites were Present in Each construct to induce genomic integration with SB transposase Each transgene was expressed by elongation factor 1 alpha (EF1α) promoter.

Genetic Transformation and Propagation of Cells:

The Amaxa Nucleofector® II was utilized to transform human PBMC, where $1\text{-}2*10^7$ thawed PBMC were electroporated in Amaxa T cell Nucleofector solution using program U14, as previously described. The next day, PBMC were stimulated with CM with AaPC at a ratio of 1:1 including 50 IU/mL IL-2. The co-culture of T cells and AaPC was maintained at $1*10^6$ cells/mL with each subsequent stimulation. Outgrowth of T cells was promoted by re-stimulated of co-cultures every 7 days with IL-2 and AaPC at the concentrations noted. Fresh IL-2 was added when media was changed between stimulations. During transgenic experiments, drugs were added 48 hours after co-culture initiation and maintained at the given concentration until day 14. After day 14, no drugs were added to T cell cultures.

Western Blot:

When noted, T cells were removed from cultures for western blot by centrifugation of $1*10^6$ T cells, and rapid freezing of the cell pellet in liquid nitrogen. T cell pellets were lysed and prepared with 50 mM Tris, 150 mM NaCl, 1 mM EDTA, 1% NP-40, 0.5% deoxycholate, 1 mM phenylmethylsulfonyl fluoride, 150 mM p-nitrophenyl phosphate and 0.3 µM Aprotinin, pH 7.4. SDS-PAGE separated proteins and primary antibodies noted in Table 6 were used to detect the presence of protein via chemiluminescence.

TABLE 6

Western Blot Antibodies

| Antibody | Manufacturer | Cat. No. | Dilution |
|---|---|---|---|
| AMPKα | Cell Signaling Technology (CST), Danvers, MA | 2603S | 1:1000 |
| p-AMPKα (T172) | CST | 2535S | 1:1000 |
| S6 | CST | 2317S | 1:1000 |
| p-S6 (S235/236) | CST | 3945S | 1:1500 |
| Actin | Sigma | A2228 | 1:10000 |
| Hsp-70 | Santa Cruz Biotechnology, Dallas, TX | SC-24 | 1:5000 |
| eEF2 | LifeSpan Biosciences, Seattle, WA | LS-B8940 | |
| p-eEF2 (T56) | LifeSpan Biosciences | LS-C198899 | |

Flow Cytometry:

Cultured T cells were washed in FACS staining solution [95] before surface antibody staining was performed in FACS staining solution with fluorochrome-conjugated antibodies at 4° C. for at least 30 minutes. Intracellular transcription factor and cytokine staining utilized the FoxP3/transcription factor staining buffer set manufacturer's protocol (eBioscience, 00-5523-00), and was performed following surface staining. The BD FACSCalibur (BD Biosciences) analyzed most samples expressing FoxP3. Antibody targets, concentrations, and manufacturers are listed in Table 7. Flow cytometry data analysis utilized FlowJo v 10.0.5 (Tree Star Inc., Ashland, Oreg.). Flow cytometric imaging of cells stained for phosphorylated antigens was accomplished using the ImageStreamX Mark II (Amnis, Seattle, Wash.) with the following protocol; after surface staining, samples were fixed in 100% methanol (Sigma) for 1 hour at 4° C. before washing and staining in FoxP3/transcription factor staining buffer set wash buffer as outlined by the manufacturer's protocol. Analysis of image cytometry data utilized Amnis IDEAS v 6.0.

TABLE 7

Flow Cytometry Antibodies

| Antibody | Manufacturer | Cat. No. | Dilution |
|---|---|---|---|
| CD3-APC | BD Pharmingen | 340661 | 1:33 |
| CD3-PerCP-Cy5.5 | BD Pharmingen | 340949 | 1:33 |
| CD4 FITC | BD Pharmingen | 340133 | 1:33 |
| CD4-PE | BD Pharmingen | 347327 | 1:33 |
| CD4-PerCP-Cy5.5 | BD Pharmingen | 341645 | 1:33 |
| CD8-APC | BD Pharmingen | 340659 | 1:33 |
| CD25-APC | BD Pharmingen | 555434 | 1:33 |
| CD39-APC | BD Pharmingen | 560239 | 1:33 |
| CD45RO-APC | BD Pharmingen | 559865 | 1:33 |
| CD152-APC | BD Pharmingen | 555855 | 1:33 |
| KI-67-AF647 | BD Pharmingen | 561126 | 1:50 |
| Annexin V | BD Pharmingen | 556422 | 1:20 |
| 7-AAD | BD Pharmingen | 559925 | 1:20 |
| Propidium Iodide | BD Pharmingen | 556463 | |
| FoxP3-PE | eBiosciences | 12-4777-42 | 1:20 |
| Helios-APC | Biolegend | 137222 | 1:05 |
| LAP-APC | Biolegend | 349608 | 1:20 |
| IFN-g-APC | Biolegend | 502516 | 1:20 |
| IL-2-APC | Biolegend | 500315 | 1:20 |
| p-eEF2 (T56) | LifeSpan Biosciences | LS-C198899 | 1:20 |
| p-AMPKα (T172) | AbCam | Ab133448 | 1:20 |
| CD4-Pacific Blue | BD Pharmingen | 558116 | 1:33 |
| p-S6 (S244) - AF647 | BD Pharmingen | 560465 | 1:20 |
| Goat anti-Rabbit - AF488 | Life Technologies | A-11034 | 1:100 |

Thymidine Incorporation Assay:

A thymidine incorporation assay was performed with anti-CD3/CD28 and IL-2 used to stimulate each well containing $2*10^5$ viable cells. Varying ratios of effector T cells ($T_{eff}$) to $T_{reg}$ were combined in each well and all wells were run in triplicate in U-bottom 96 well plates. At 48 hours 1 μCi [$^3$H] Thymidine (Perkin-Elmer, Waltham, Mass.) was added to each well, and 24 hours later the cells were assessed for radioactivity on a Top Count NXT (Perkin-Elmer). $T_{reg}$ mediated suppression of growth was determined by the following equation: (No Treatment $T_{eff}$ [cpm]–($T_{reg}$ & No Treatment $T_{eff}$ [cpm]))/No Treatment $T_{eff}$ [cpm].

Statistical Analysis:

Graphical representation and statistical analysis of data was performed with Prism v6.0 (Graph Pad Software Inc., La Jolla, Ca). One-Way ANOVA was used when appropriate with Tukey's or Dunnett's multiple comparison tests as applicable, non-Gaussian distributions were assessed by the Kruskall-Wallis test followed by Dunn's multiple comparison test. Total cell counts and expression data involving $T_{CD4, FoxP3}$ tended to be non-Gaussian in distribution. Single variable tests (experimental vs. control) were made using the Mann-Whitney test. Statistical significance was designated as α<0.05.

Results

Drug Selection of TCD4, FoxP3 by MTX Occurs in Part Through Toxicity. In order to determine how MTX contributes to the selection of $T_{CD4, FoxP3}$, freshly derived PBMC were stimulated with anti-CD3/CD28 antibodies and IL-2 in the presence of cytotoxic drugs or lethal γ-irradiation. After 7 days there was a significant difference in survival markers Annexin V and 7-AAD in stimulated T cells receiving any cytotoxic insult with stimulation (FIG. 1B-I). The selection of $T_{CD4, FoxP3}$ was not as consistent as cytotoxicity. Following 7 days of stimulation, 2 Grey γ-irradiation significantly increased the amount of $T_{CD4, FoxP3}$ in the surviving population (FIG. 1B-II). This lethal treatment did not target a common pathway being considered, nor did cisplatin, yet both increased $T_{CD4, FoxP3}$. However, the $T_{CD4, FoxP3}$ increase induced by cisplatin is insignificant. Significant increases were derived from 5-FU and MTX. With the exception of ribosomal elongation inhibitor G418, each cytotoxic treatment appeared to increase the percentage of surviving $T_{CD4, FoxP3}$. See Bar-Nun S. et al., Biochimica et biophysica acta 1983, 741(1):123-127. This pattern of increasing $T_{CD4, FoxP3}$ percentage in the face of varied cytotoxic insult suggests a common pathway that can be enhanced by certain drugs. Without wishing to be bound by theory, this pathway is likely related to the reduced proliferation rate of $T_{reg}$, and appears to be ribosomally mediated as G418 can inhibit this general trend of increasing $T_{CD4, FoxP3}$ percentage. See Cao M. et al., International journal of radiation biology 2011, 87(1):71-80.

The findings of $T_{reg}$ depletion with G418 and $T_{reg}$ selection by MTX were further evaluated for dose dependence by stimulating thawed PBMC with anti-CD3/CD28+IL-2 for 7 days, as before. G418 was significantly cytotoxic at all doses tested, but significantly depleted $T_{CD4, FoxP3}$ at two moderate drug doses (FIG. 10C). MTX was also cytotoxic at all doses tested, but had significant elevation of $T_{CD4, FoxP3}$, at lower doses (FIG. 10D). Rapamycin (Rapa) was used as a $T_{reg}$ selection control[138] and showed similar $T_{CD4, FoxP3}$ selection at a moderate drug concentration independent of cytotoxicity, which only occurred at the highest doses (FIG. 10F). The selection for or against $T_{reg}$ at moderate drug doses rather than higher doses suggests that $T_{reg}$ have a narrow therapeutic window for drug induced selection or depletion. A specific inhibitor of ATIC[142] was used to test whether MTX mediates selection of $T_{CD4, FoxP3}$ through inhibition of ATIC. Without wishing to be bound by theory, inhibition of AICARtf or the heterodimeric complex ATIC, in which AICARtf is found, increases AICAR. FIG. 10E demonstrates that ATIC inhibition alone was neither cytotoxic nor selective for $T_{CD4, FoxP3}$. Further analysis of flow plots represented by the same donor in FIG. 10G show expression of CD4 and FoxP3 for several of the drugs used. Use of iATIC characteristically mediated increased expression of FoxP3 in $CD4_+$ T cells similar to that of Rapa, but did not inhibit proliferation of $FoxP3_{neg}$ T cells as MTX, G418, or Rapa. Thus, iATIC enhanced FoxP3 expression in $CD4_+$ T cells but diluted these cells by permitting proliferation of $FoxP3_{neg}$ T cells. It appears that MTX mediated selection of $T_{CD4, FoxP3}$ occurs by depletion of rapidly proliferating effector T cells and enhancement of FoxP3 expression via a pathway similar to Rapa that includes ribosomal inhibition. The increased susceptibility of $T_{regs}$ to ribosomal inhibitor G418 solidifies this relationship between enhanced FoxP3 expression and increased susceptibility to ribosomal inhibition.

Figures 12A, 12B:
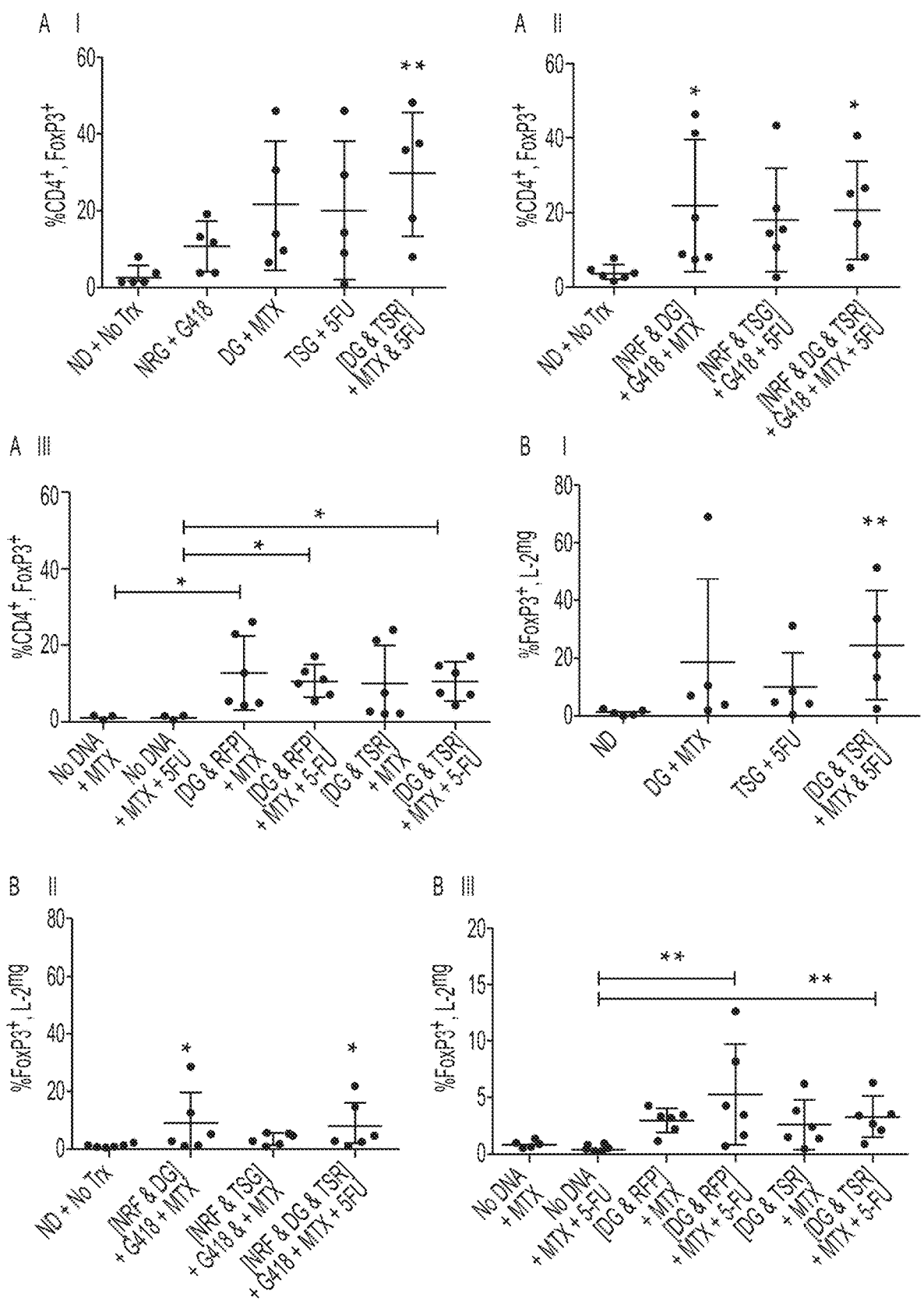
Figures 12C, 12D:
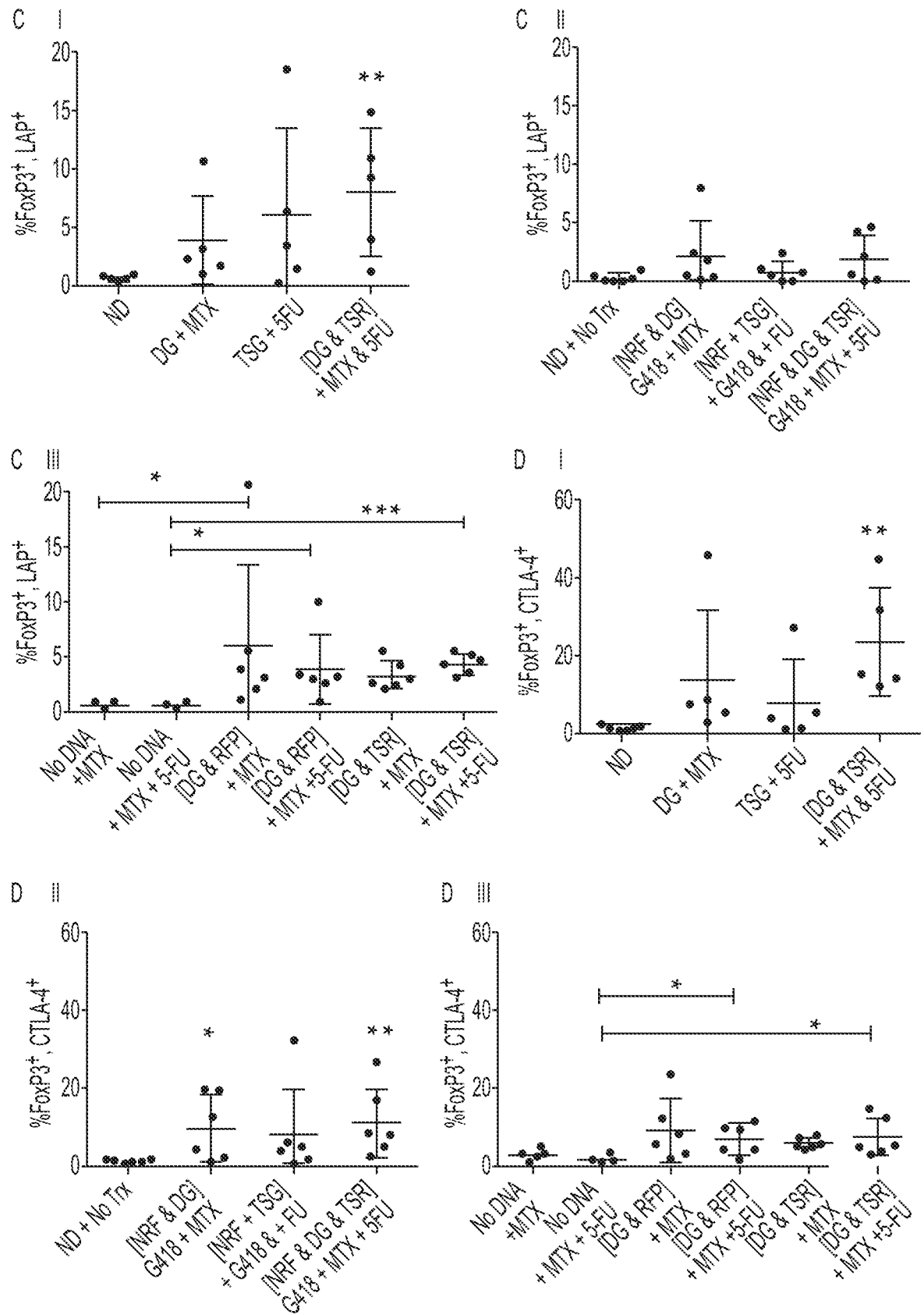

$T_{regs}$ are Preferentially Expanded in Primary T Cells Resistant to the Anti-Folate and Anti-Thymidine Actions of MTX. It was hypothesized that regulatory T cells were inhibiting $CD8_+$ T cells proliferation following drug selection. To test this hypothesis, drug resistant T cells were derived by transformation with $DHFR_{FS}$, $TYMS_{SS}$, NeoR, or a combination, and numerically expanded as previously described. Briefly, transformed T cells were selected in the presence of 0.1 μM MTX, 5 μM 5-FU, or 1.6 mM G418 as designated from day 2 to 14 while stimulation with OKT3-loaded AaPC and 50 IU/mL IL-2 occurred every 7 days until day 35. See Singh H. et al., PloS one 2013, 8(5). Initial testing for $T_{regs}$ by elevated expression of FoxP3 in the $CD4^+$ T cell population demonstrated there was a significant $T_{CD4, FoxP3}$ percentage increase in DHFR$^{FS}$ expressing T cells. Selection using MTX in comparison to mock-electroporated (No DNA) T cells on Day 21 showed this increase (FIG. 11), and this increase persisted to Day 35 when 5-FU was combined with MTX during selection (FIG. 12A). The transgenic T cells were almost entirely CD4$^+$ in each experimental population after selection, but the predominance of $T_{regs}$ appeared to often exceed the 5-10% typically found in the un-manipulated CD4$^+$ T cell compartment. Markers of $T_{reg}$ function were also assessed. Low IL-2 expression$_{[\ ]}$ is a known trait of $T_{regs}$ and is assessed with FoxP3 expression. The percentage of the T cell population with a FoxP3$_{pos}$, IL-2$_{neg}$ expression pattern is shown in FIG. 12B. Expression of latency associated peptide (LAP)—a part of the TGF-β complex and strongly associated with activated $T_{reg}$ and is seen in FIG. 12C.

The transgenes DHFR$^{FS}$ and TYMS$^{SS}$ were compared individually and in combination to the control selection vector NeoR and un-treated No DNA T cells. Selection towards $T_{reg}$ in this experiment may be noted in FIG. 12A, B, C-I. This experiment demonstrated that [DHFR$^{FS}$-GFP (DG) & TYMS$^{SS}$-RFP (TSR)]$^+$ T cells selected in MTX+ 5-FU had an increased population of cells characteristic of $T_{reg}$ when compared to mock-transformed T cells. To further elucidate the contribution of DHFR$^{FS}$ and TYMS$^{SS}$ to $T_{reg}$ selection, NeoR was co-electroporated with DHFR$^{FS}$, TYMS$^{SS}$, or the combination. The addition of NeoR permitted equivalent selection of DHFR$^{FS}$, TYMS$^{SS}$, and the combination in all T cell populations. With un-transformed T cells removed, it became clear that DHFR$_{FS}$ alone, but not TYMS$^{SS}$ alone could select for cells characteristic of $T_{regs}$ (FIGS. 12A, B, and C-II). [DG & TSR]$^+$ T cells continued to select for cells with $T_{reg}$ features. Finally, the contribution of TYMS$^{SS}$ to the selection of $T_{reg}$ by DHFR$^{FS}$ was assessed by co-electroporation of TSR or a control vector—RFP. The characteristics of $T_{regs}$ from this experiment are shown in FIGS. 12A, B, and C-III. This experiment demonstrates that selection of DHFR$^{FS}$ with MTX can enhance outgrowth of $T_{reg}$ and that 5-FU enhances this selection independent of TYMS$^{SS}$. Selection of $T_{reg}$ benefits from folate rescue by DHFR$^{FS}$. This is expected as folate is known to play a role in $T_{reg}$ survival. See Kunisawa J. et al., *PloS one* 2012, 7(2):e32094. Surprisingly, selection of $T_{reg}$ did not require de novo thymidine synthesis as TYMS$^{SS}$, which alleviates MTX and 5-FU inhibition of TYMS, was dispensable.

Previous findings showed survival and toxicity of 5-FU in PBMC is mediated by TYMS and an alternative mechanism. See Eisenthal A et al., *Anticancer research* 2009, 29(10): 3925-3930. Combining the known mechanisms of $T_{reg}$ selecting drugs MTX, 5-FU, and rapamycin yielded the diagram in FIG. 13, which details how each drug interacts with ribosomal function. It was noted in an experiment depicted in Supplemental FIG. 1A that Neomycin resistance gene rescued $T_{CD4, FoxP3}$ from the treatment of G418. This finding suggests that a specific action of G418 is responsible for $T_{CD4, FoxP3}$ depletion, and this phenomenon was further explored.

Ribosomal Inhibition by Aminoglycoside G418 Selectively Depletes Replicating $T_{CD4, FoxP3}$. Thawed PBMC were activated with anti-CD3/CD28+IL-2 for 7 days in the presence of alternative doses of G418, Hygromycin B—a different aminoglycoside, Zeocin—a DNA targeting antibiotic, and Rapa to assess the dose dependent selection or depletion of $T_{CD4, FoxP3}$ by aminoglycosides (FIG. 14A). Depletion of $T_{CD4, FoxP3}$ is again noted in the presence of aminoglycoside G418. The alternative aminoglycoside—hygromycin—developed an insignificant increase in $T_{CD4, FoxP3}$ at 0.2 mM hygromycin. This increase significantly decreased with higher doses of hygromycin—1.5 and 2.3 mM. Hygromycin showed no significant depletion of $T_{CD4, FoxP3}$ from untreated control.

Ribosomal Inhibition by aminoglycoside G418 selectively depletes replicating $T_{CD4, FoxP3}$. Thawed PBMC were activated with anti-CD3/CD28+IL-2 for 7 days in the presence of alternative doses of G418, Hygromycin B—a different aminoglycoside,$_{[146]}$ Zeocin—a DNA targeting antibiotic, and Rapa to assess the dose dependent selection or depletion of $T_{CD4, FoxP3}$ by aminoglycosides (FIG. 14A). Depletion of $T_{CD4, FoxP3}$ is again noted in the presence of aminoglycoside G418. The alternative aminoglycoside-hygromycin—developed an insignificant increase in $T_{CD4, FoxP3}$ at 0.2 mM hygromycin. This increase significantly decreased with higher doses of hygromycin—1.5 and 2.3 mM. Hygromycin showed no significant depletion of $T_{CD4, FoxP3}$ from untreated control.

This dose dependent depletion of $T_{CD4, FoxP3}$ is consistent with that seen for G418, and was not noted with increasing doses Zeocin or Rapa. An increase of $T_{CD4, FoxP3}$ was noted with increasing doses of Zeocin, yet this was insignificant, similar to that seen for other cytotoxic drugs in FIG. 10B-II. A representative flow plot of CD4 and FoxP3 expression from the same donor can be seen in FIG. 14B. Here, the trends can be visualized.

It was considered that polyclonal stimulation may play some part in the G418 depletion of $T_{CD4, FoxP3}$. To test this, PBMC were rested in CM for 9 days after thawing +/−G418 and tested for the presence of $T_{CD4, FoxP3}$. Significant depletion of $T_{CD4, FoxP3}$ by G418 persisted under resting conditions (FIG. 14C—left panel). This was replication dependent as CD4$_+$, FoxP3$_+$, Ki-67$_+$ cells showed significant G418 mediated depletion while CD4$_+$, FoxP3$_+$, Ki-67$_{neg}$ cells were not significantly depleted by the same post-Hoc measure (FIG. 14C—right panel). Representative flow diagrams of resting PBMC in FIG. 14D—upper panel show the loss in expression of FoxP3 for CD4$_+$ T cells after treatment with G418. An alternative view of Ki-67 and FoxP3 expression in FIG. 14D—lower panel demonstrates that FoxP3$_{neg}$ T cells continue to proliferate in the presence of G418, further supporting the selective targeting of G418 to $T_{CD4, FoxP3}$ at this concentration. Thus, proliferating $T_{CD4, FoxP3}$ are depleted following treatment with aminoglycoside G418.

As G418 and hygromycin are considered toxic to live animals, gentamicin, an aminoglycoside well known for its use in humans and animal models, was tested for selective TCD4, FoxP3 depletion. See Lopez-Novoa J M. et al., *Kidney international* 2011, 79(1):33-45. FIG. 3E depicts this depletion of $T_{CD4, FoxP3}$ in resting PBMC after 7 days and demonstrates the consistent action of aminoglycosides in depleting TCD4, FoxP3. It was next tested whether depletion of $T_{CD4, FoxP3}$ corresponded with a loss of $T_{reg}$ marker expression or selective $T_{reg}$ toxicity.

Sorted Treg Differentiate the Effects of MTX, 5-FU, and G418 on Selection in Bulk PBMC. Magnetic sorting for CD4 and CD25 expressing PBMC yielded a CD4$_+$ CD25$_+$ population that is widely considered to contain $T_{reg}$, and a CD25$_{neg}$ population of effector T cells ($T_{eff}$). See Miyara M. et al., *Immunity* 2009, 30(6):899-911. These populations were treated with the same concentrations of MTX, 5-FU, G418, or no treatment, as above, for the first 7 days of co-culture with AaPC. After this period of time, co-culture continued without drug by stimulating with AaPC every 7 days until Day 21. Cells were assayed at this time for expression of CD25, CTLA-4, LAP, and IL-2, as before. The experimental outline can be seen in FIG. 15A. A [$^3$H] thymidine incorporation assay was also performed to determine the effect of each drug on the functionality of propagated $T_{reg}$.

When the surviving CD4$^+$ cells were assayed on day 21 it was found that no drug significantly selected for $T_{CD4, FoxP3}$ in the $T_{eff}$ compartment, nor did MTX and 5-FU improve selection for $T_{CD4, FoxP3}$ in the $T_{reg}$ compartment (FIG. 15B). The most consistent finding was that G418 persistently decreased surviving $T_{reg}$ following drug treatment. This was demonstrated by loss of surviving $T_{CD4, FoxP3}$ (FIG. 15B). $T_{reg}$ markers such as CD25 (FIG. 15C-I), CTLA-4 (FIG. 15C-II), decreased IL-2 expression (FIG. 4C-III), or LAP (FIG. 15C-IV), in combination with FoxP3 expression was also decreased following stimulation on day 21. Thus, $T_{reg}$ are lost, likely due to toxicity of G418, rather than inhibited as 2 weeks of growth promoting co-culture conditions could not sufficiently restore $T_{regs}$ following G418 treatment.

The $T_{reg}$ promoting properties of MTX and 5-FU appeared to depend in part upon the presence of $T_{eff}$, as the enhanced selection of $T_{CD4, FoxP3}$ was no longer noticeable after $T_{eff}$ were removed from the culture system (FIG. 15B). The improved selection towards $T_{reg}$ phenotypes may have been accomplished by depletion of $T_{eff}$ which are known to contaminate $T_{reg}$ sorting.[113] It is likely that the ability of $T_{reg}$ to survive the cytotoxic insult of MTX or 5-FU in comparison to $T_{eff}$ was a primary component of the enhanced selection. Although there was a trend towards improved selection of $T_{reg}$ phenotypes (FIG. 15C-I, II, III) when MTX or 5-FU was used, there was no significant difference for expression of CD25, CTLA-4, or loss of IL-2. However, the $T_{reg}$-specific marker LAP was significantly increased by early treatment with MTX or 5-FU (FIG. 15C-IV). As LAP was the only increased marker of those assayed, it is likely that LAP and the associated expression of TGF-$\beta$[143] was the probable cause for improved suppression of MTX and 5-FU treated $T_{reg}$ above untreated $T_{reg}$ (FIG. 15D). Thus, MTX and 5-FU appear to have two components in enhancing selection of $T_{reg}$: 1) $T_{eff}$ are selectively depleted by MTX and 5-FU, and 2) MTX and 5-FU increase the expression of LAP weeks after treatment.

Stimulation of $T_{CD4, FoxP3}$ Enhances AMPK Activation and Leads to Inhibition of eEF2—a Factor that Plays a Role in Translational Elongation. AMPK is hypothesized to play a role in selection of $T_{CD4, FoxP3}$, as noted above (FIG. 13). Furthermore, enhanced activation of AMPK may lead to inhibition of eEF2 in $T_{CD4, FoxP3}$. See Browne G J. et al., *The Journal of biological chemistry* 2004, 279(13): 12220-12231. Preferential inhibition of translational elongation could explain selection for $T_{CD4, FoxP3}$ in the presence of many cytotoxic drugs and depletion of $T_{CD4, FoxP3}$ in the presence of inhibitors of translational elongation. This was tested by assessing phosphorylation of AMPK 24 hours after activation of PBMC using flow cytometry (FIGS. 16A & B) and imaging cytometry (FIG. 16C). The phosphorylation of AMPK on T172 indicates activation and was enhanced in stimulated over unstimulated $T_{CD4, FoxP3}$ See Hardie D G et al., *Diabetes* 2013, 62(7):2164-2172. This enhanced activation of AMPK was increased in CD4$^+$, FoxP3$_{neg}$ T cells (FIG. 16A—upper panel) as well, but the significant increase (p=0.03 by t-test) did not persist following post-hoc analysis. Likewise, flow plots of activated AMPK with FoxP3 show this enhancement of AMPK activation is much more noticeable in the FoxP3-expressing subset (FIG. 16B—upper panel). See MacIver N J et al., *Journal of immunology* 2011, 187(8):4187-4198. A marker of translational initiation—S6—is susceptible to mTOR regulation, and is phosphorylated when active. See Mahoney S J et al., *Progress in molecular biology and translational science* 2009, 90:53-107. Phosphorylation of 56 (p-S6) was significantly enhanced in $T_{CD4, FoxP3}$ following stimulation (FIG. 16A—lower panel), which was previously shown by Cabone et al. See Carbone F. et al., *Nature medicine* 2014, 20(1):69-74. While p-S6 increased in the FoxP3$_{neg}$ T cells (p=0.01 by t-test), this increase was not significant following post-hoc analysis. The enhancement of p-S6 is observable in the representative flow plot for FIG. 16B—lower panel. The activation of metabolic regulators AMPK and S6 was enhanced in both FoxP3$^+$ and FoxP3$^{neg}$ CD4$^+$ T cells following activation, but the increase was only significant in $T_{CD4, FoxP3}$ in a Two-Way ANOVA with post-hoc Sidak's test. The increased activation of AMPK and S6 following activation of $T_{CD4, FoxP3}$ can be seen with image cytometry profiles shown in FIG. 16D before—top panel—and after stimulation with anti-CD3/CD28 and IL-2—bottom panel. The same compensation and visualization were applied to each panel making the top and bottom panels comparable.

Without wishing to be bound by theory, enhanced activation of AMPK in $T_{CD4, FoxP3}$ suggests translational elongation may be inhibited by phosphorylation of eEF2 and could account for the increased survival of $T_{CD4, FoxP3}$ in the presence of cytotoxic drugs and susceptibility to inhibitors of translational elongation, like aminoglycosides. The same experiment as in FIG. 16 A-C was performed to assess the inactivation of eEF2 by phosphorylation at T56.[135] Image cytometry was used to quantify and visualize all events. FIG. 16D demonstrates a significant increase in phosphorylation of eEF2 in the same subset of T cells—$T_{CD4, FoxP3}$—following stimulation. Also, inhibitory phosphorylation of eEF2 was significantly increased above stimulated FoxP3$_{neg}$ T cells, which was not noted with AMPK or S6 phosphorylation. The increased phosphorylation of eEF2 only in stimulated $T_{CD4, FoxP3}$ suggests that $T_{CD4, FoxP3}$ would have decreased replicative capacity upon stimulation, as shown by Cao et al. Decreased levels of active eEF2, which inhibit progression through the cell cycle, suggest that increased phosphorylation of eEF2 may account for the survival of $T_{CD4, FoxP3}$ in cytotoxic environments, which was noted in FIG. 10. Similarly, decreased translational capacity would make $T_{CD4, FoxP3}$ increasingly susceptible to inhibitors of translational elongation, as was shown with aminoglycosides in FIG. 14. Therefore, the activity of eEF2 may be the primary factor influencing both selection and depletion of $T_{reg}$ in these studies.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All cited patents and publications referred to in this application are herein incorporated by reference in their entirety.

What is claimed is:

1. An isolated engineered mammalian T cell comprising a protein comprising the amino acid sequence of SEQ ID NO:12 (dihydrofolate reductase$^{FS}$; DHFR$^{FS}$) and a protein comprising the amino acid sequence of SEQ ID NO: 11 (thymidylate synthase$^{SS}$; TYMS$^{SS}$).

2. The isolated engineered mammalian T cell of claim 1, wherein the isolated transgenic mammalian T cell is a T helper cell (TH cell), cytotoxic T cell (Tc cell or CTL), memory T cell (TCM cell), effector T cell (TEM cell), regulatory T cell (Treg cell; also known as suppressor T cell), natural killer T cell (NKT cell), mucosal associated invariant T cell, alpha-beta T cell (Tαβ eels cell), or gamma-delta T cell (Tγδ cell).

3. An isolated engineered mammalian T cell comprising a nucleotide sequence comprising a transgene of interest and a nucleotide sequence encoding a protein comprising the amino acid sequence of SEQ ID NO: 12 (dihydrofolate reductase$^{FS}$; DHFR$^{FS}$) and a nucleotide sequence encoding a protein comprising the amino acid sequence of SEQ ID NO: 11 (thymidylate synthase$^{SS}$; TYMS$^{SS}$).

4. A method for providing controlled expression of a first transgene comprising providing an engineered mammalian cell comprising a nucleic acid comprising the first transgene operably linked to a nucleotide sequence encoding a protein comprising the amino acid sequence of SEQ ID NO: 11 (thymidylate synthase$^{SS}$; TYMS$^{SS}$), said cell further comprising a nucleotide sequence encoding a protein comprising the amino acid sequence of SEQ ID NO: 12 (dihydrofolate reductase$^{FS}$; DHFR$^{FS}$).

5. The method of claim 4, wherein the first transgene and nucleotide sequence encoding the protein comprising the amino acid sequence of SEQ ID NO: 11 upon expression are encoded on the same mRNA.

6. The method of claim 4, wherein the sequence encoding the first transgene and the nucleotide sequence encoding the protein comprising the amino acid sequence of SEQ ID NO: 11 are separated by an internal ribosomal entry site (IRES) or a ribosomal slip sequence.

7. The method of claim 4, wherein the first transgene of interest is a chimeric antigen receptor (CAR) construct.

8. The method of claim 4, wherein the first transgene of interest is a polypeptide hormone, chemokine or cytokine.

9. The method of claim 8, wherein the cytokine is IL-12.

10. The method of claim 8, wherein the cytokine is IL-15.

11. The method of claim 4, wherein the nucleotide sequence encoding the protein comprising the amino acid sequence of SEQ ID NO: 12 is operably linked to a second transgene.

12. The method of claim 11, wherein the second transgene and the nucleotide sequence encoding the protein comprising the amino acid sequence of SEQ ID NO: 12 upon expression are encoded on the same mRNA.

13. The method of claim 12, wherein the sequence encoding the second transgene of interest and nucleotide sequence encoding the protein comprising the amino acid sequence of SEQ ID NO: 12 are separated by an internal ribosomal entry site (IRES) or a ribosomal slip sequence.

14. The method of claim 12, wherein the second transgene is a suicide gene, CAR, TCR, polypeptide hormone, cytokine, chemokine or transcription factor.

15. The method of claim 14, wherein the suicide gene is an inducible suicide gene.

16. The method of claim 15, wherein the suicide gene is an inducible Caspase 9.

17. The isolated engineered mammalian T cell of claim 1, further comprising a transgene.

18. The isolated engineered mammalian T cell of claim 3, wherein the nucleotide sequence encoding the protein comprising the amino acid sequence of SEQ ID NO: 12 is codon optimized.

19. The isolated engineered mammalian T cell of claim 3, wherein the nucleotide sequence encoding the protein comprising the amino acid sequence of SEQ ID NO: 11 is codon optimized.

* * * * *

UNITED STATES PATENT AND TRADEMARK OFFICE
CERTIFICATE OF CORRECTION

PATENT NO. : 10,808,230 B2
APPLICATION NO. : 15/552821
DATED : October 20, 2020
INVENTOR(S) : Rushworth et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*